US012606604B2

(12) United States Patent (10) Patent No.: US 12,606,604 B2
Vallera et al. (45) Date of Patent: *Apr. 21, 2026

(54) THERAPEUTIC COMPOUNDS AND METHODS

(71) Applicant: Regents of the University of Minnesota, Minneapolis, MN (US)

(72) Inventors: Daniel Attilio Vallera, Richfield, MN (US); Jeffrey S. Miller, Little Canada, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 1294 days.

This patent is subject to a terminal disclaimer.

(21) Appl. No.: 17/396,127

(22) Filed: Aug. 6, 2021

(65) Prior Publication Data

US 2021/0395326 A1 Dec. 23, 2021

Related U.S. Application Data

(63) Continuation of application No. 15/766,067, filed as application No. PCT/US2016/055722 on Oct. 6, 2016, now Pat. No. 11,098,100.

(60) Provisional application No. 62/237,835, filed on Oct. 6, 2015.

(51) Int. Cl.

| | |
|---|---|
| *A61K 39/395* | (2006.01) |
| *A61P 35/00* | (2006.01) |
| *A61P 35/02* | (2006.01) |
| *C07K 14/54* | (2006.01) |
| *C07K 14/55* | (2006.01) |
| *C07K 16/10* | (2006.01) |
| *C07K 16/24* | (2006.01) |
| *C07K 16/28* | (2006.01) |
| *C07K 16/30* | (2006.01) |
| *C12N 5/0783* | (2010.01) |
| *A61K 38/00* | (2006.01) |

(52) U.S. Cl.
CPC .............. *C07K 14/55* (2013.01); *A61P 35/00* (2018.01); *A61P 35/02* (2018.01); *C07K 14/5443* (2013.01); *C07K 16/1045* (2013.01); *C07K 16/244* (2013.01); *C07K 16/2803* (2013.01); *C07K 16/2809* (2013.01); *C07K 16/283* (2013.01); *C07K 16/30* (2013.01); *C12N 5/0646* (2013.01); *A61K 38/00* (2013.01); *C07K 2317/22* (2013.01); *C07K 2317/54* (2013.01); *C07K 2317/55* (2013.01); *C07K 2317/622* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 9,090,876 | B2 | 7/2015 | Velardi et al. |
| 9,155,798 | B2 | 10/2015 | Vallera |
| 10,358,492 | B2 | 7/2019 | Bakker et al. |
| 11,098,100 | B2 | 8/2021 | Vallera et al. |
| 11,098,101 | B2 | 8/2021 | Vallera et al. |
| 2006/0104971 | A1 | 5/2006 | Garber et al. |
| 2006/0134102 | A1 | 6/2006 | Lepage et al. |
| 2009/0215119 | A1 | 8/2009 | Ladner |
| 2014/0072581 | A1 | 3/2014 | Dixit et al. |
| 2014/0242025 | A1 | 8/2014 | Wong et al. |
| 2014/0378664 | A1 | 12/2014 | Suh et al. |
| 2015/0374790 | A1 | 12/2015 | Liu et al. |
| 2017/0368169 | A1 | 12/2017 | Loew et al. |
| 2018/0282386 | A1 | 10/2018 | Vallera et al. |
| 2020/0087369 | A1 | 3/2020 | Vallera et al. |
| 2020/0148737 | A1 | 5/2020 | Vallera et al. |

FOREIGN PATENT DOCUMENTS

| | | |
|---|---|---|
| EP | 2332994 | 6/2011 |
| EP | 3457139 | 3/2019 |
| JP | 2010-500967 | 1/2010 |
| JP | 2010-517048 | 5/2010 |
| JP | 2012-100677 | 5/2012 |
| JP | 2013-513370 | 4/2013 |
| JP | 2013-535187 | 9/2013 |
| JP | 2014-507150 | 3/2014 |
| JP | 2014-518064 | 7/2014 |
| KR | 10-2005-0085775 A | 8/2005 |
| RU | 2014100350 | 7/2015 |
| WO | WO 2004/055056 A1 | 7/2004 |
| WO | WO 2005/061547 A2 | 7/2005 |
| WO | 2005/089788 | 9/2005 |
| WO | 2006/099141 | 9/2006 |
| WO | 2008/011157 | 1/2008 |
| WO | 2008/092164 | 7/2008 |

(Continued)

OTHER PUBLICATIONS

Heiss, "The trifunctional antibody catumaxomab for the treatment of malignant ascites due to epithelial cancer: Results of a prospective randomized phase II/III trial" 2010 Int J Cancer, 127(9):2209-21.

(Continued)

*Primary Examiner* — Meera Natarajan
(74) *Attorney, Agent, or Firm* — Mueting Raasch Group

(57) ABSTRACT

This disclosure describes engineered compounds that engage NK cells and methods of using the compounds. Generally, the compound includes an NK engaging domain, a targeting domain that selectively binds to a target cell, and an NK activating domain operably linking the NK engaging domain and the targeting domain.

18 Claims, 24 Drawing Sheets
Specification includes a Sequence Listing.

(56)                    References Cited

FOREIGN PATENT DOCUMENTS

WO      2009/029601      3/2009
WO      2009/051974      4/2009
WO      2011/070109      6/2011
WO      2012/006490      1/2012
WO      2012/040323      3/2012
WO      2012/113266      8/2012
WO      2012/167143      12/2012
WO      2012/175222      12/2012
WO      2013/039883      3/2013
WO      2013/163427      10/2013
WO      2014/138306      9/2014
WO      2015/090229      6/2015
WO      2017/062604      4/2017
WO      2019/035938      2/2019
WO      2019/139888      7/2019

OTHER PUBLICATIONS

Hodge, "Interleukin-15 enhances proteasomal degradation of bid in normal lymphocytes: implications for large granular lymphocyte leukemias" 2009 Cancer Res., 69(9):3986-94.

Huntington, "IL-15 trans-presentation promotes human NK cell development and differentiation in vivo" 2009 J Exp Med., 206(1):25-34.

Imai, "Chimeric receptors with 4-1BB signaling capacity provoke potent cytotoxicity against acute lymphoblastic leukemia" 2004 Leukemia, 18(4):676-84.

Jakobisiak, "Interleukin 15 as a promising candidate for tumor immunotherapy" 2011 Cytokine Growth Factor Rev., 22: 99-108.

Khawam, "Human renal cancer cells express a novel membrane-bound interleukin-15 that induces, in response to the soluble interleukin-15 receptor alpha chain, epithelial-to-mesenchymal transition" 2009 Cancer Res., 69(4):1561-9.

King, "Phase I clinical trial of the immunocytokine EMD 273063 in melanoma patients" 2004 J Clin Oncol., 22(22):4463-73.

Klein, "Surface IgM-kappa specificity on a Burkitt lymphoma cell in vivo and in derived culture lines" 1968 Cancer Res., 28(7):1300-10.

Ko, "Safety, pharmacokinetics, and biological pharmacodynamics of the immunocytokine EMD 273066 (huKS-IL2): results of a phase I trial in patients with prostate cancer" 2004 J Immunother., 27(3):232-9.

Kuniyasu, "Production of interleukin 15 by human colon cancer cells is associated with induction of mucosal hyperplasia, angiogenesis, and metastasis" 2003 Clin Cancer Res., 9(13):4802-10.

Kuniyasu, "Interleukin-15 expression is associated with malignant potential in colon cancer cells" 2001 Pathobiology, (69):86-95.

Lanier, "The relationship of CD16 (Leu-11) and Leu-19 (NKH-1) antigen expression on human peripheral blood NK cells and cytotoxic T lymphocytes" 1986 J Immunol., 136(12):4480-6.

Lanier, "Functional and biochemical analysis of CD16 antigen on natural killer cells and granulocytes" 1988 J Immunol., 141: 3478-85.

Lanier, "Natural killer cell receptor signaling" 2003 Curr Opin Immunol., (3):308-14.

Lin, "The role of shared receptor motifs and common Stat proteins in the generation of cytokine pleiotropy and redundancy by IL-2, IL-4, IL-7, IL-13, and IL-15" 1995 Immunity, 2: 331-9.

Ma, "Myelodysplastic syndromes: incidence and survival in the United States" 2007 Cancer, (8): 1536-1542.

Maretzky, "A transforming Src mutant increases the bioavailability of EGFR ligands via stimulation of the cell-surface metalloproteinase ADAM17" 2011 Oncogene, (5): 611-8.

Mccall, "Isolation and characterization of an anti-CD16 single-chain Fv fragment and construction of an anti-HER2/neu/anti-CD16 bispecific scFv that triggers CD16-dependent tumor cytolysis" 1999 Mol Immunol., (7): 433-445.

Miller, "Successful adoptive transfer and in vivo expansion of human haploidentical NK cells in patients with cancer" 2005 Blood, 105:3051-7.

Miller, "Expansion and homing of adoptively transferred human natural killer cells in immunodeficient mice varies with product preparation and in vivo cytokine administration: implications for clinical therapy" 2014 Biol Blood Marrow Transplant, 20:1252-7.

Miller, "Trispecific Killer Engagers (TrikEs) that contain IL-15 to make NK cells antigen specific and to sustain their persistence and expansion" Dec. 2015 Blood, pp. 1-4.

Mishra, "Molecular pathways: Interleukin-15 signaling in health and cancer" 2014 Clin Cancer Res., 20: 2044-50.

Munger, "Studies evaluating the antitumor activity and toxicity of interleukin-15, a new T cell growth factor: comparison with interleukin-2" 1995 Cell Immunol., 165(2):289-93.

Munz, "The emerging role of EpCAM in cancer and stem cell signaling" 2009 Cancer Res., 69(14):5627-9.

Munz, "The carcinoma-associated antigen EpCAM upregulates c-myc and induces cell proliferation" 2004 Oncogene, 23(34):5748-58.

National Center for Biotechnology Information, National Library of Medicine, National Institutes of Health, Accession No. EF5612921, " Lama glama clone C21 immunoglobulin heavy chain variable region mRNA, partial cds," [online]. Bethesda, MD [retrieved on Apr. 4, 2019]. Retrieved from the Internet: https://www.ncbi.nlm.nih.gov/nuccore/EF561291.1; 3 pgs.

NCCN. "NCCN Clinical Practice Guidelines in Oncology (NCCN Guidelines) Myelodysplastic Syndromes Version 2. 2014" 2013.

Ochoa, "Interleukin-15 in gene therapy of cancer" 2013 Curr Gene Ther., 13: 15-30.

Osenga, "A phase I clinical trial of the hu14.18-IL2 (EMD 273063) as a treatment for children with refractory or recurrent neuroblastoma and melanoma: a study of the Children's Oncology Group" 2006 Clin Cancer Res., 12(6):1750-9.

Papadakis, "TL1A synergizes with IL-12 and IL-18 to enhance IFN-gamma production in human T cells and NK cells" 2004 J Immunol., 172(11):7002-7.

Petrelli, "Regression of liver metastases after treatment with intraperitoneal catumaxomab for malignant ascites due to breast cancer" 2013 Target Oncol., 8(4):291-4. doi:10.1007/s11523-012-0240-y.

Pinz, "Preclinical targeting of human T cell malignancies using CD4-specific chimeric antigen receptor (CAR)-engineered T cells" 2015 Leukemia, 30(3):701-7. doi: 10.1038/leu.2015.311, Epub Nov. 3, 2015.

Ranson, "IL-15 is an essential mediator of peripheral NK-cell homeostasis" 2003 Blood, 101(12):4887-93.

Richards, "Anti-tumour effects of a specific anti-ADAM17 antibody in an ovarian cancer model in vivo" 2012 PLoS One, (7):e40597.

Schmohl, "Improvement in ADCC and NK cell activation of an anti-carcinoma bispecific antibody by genetic insertion of a modified IL-15 cross-linker" 2016 Oncol. Res. Treatm., 39:280-280.

Schmohl, "Heterodimeric bispecific single chain variable fragments (scFv) killer engagers (BiKEs) enhance NK-cell activity against CD133+ colorectal cancer cells" Jun. 2016 Target Oncol., 11(3):353-361.

Seimetz, "Development and approval of the trifunctional antibody catumaxomab (anti-EpCAM x anti-CD3) as a targeted cancer immunotherapy" 2010 Cancer Treat Rev., 36(6):458-67. doi:10.1016/j.ctrv.2010.03.001.

Shanmugham, "IL-15 an immunoregulatory and anti-cancer cytokine. Recent advances" 2006 J Exp Clin Cancer Res., 25:529-36.

Singer, "Effective elimination of acute myeloid leukemic cells by recombinant bispecific antibody derivatives directed against CD33 and CD16" Jul.-Aug. 2010 J Immunother., 33:599-610 (2010).

Spizzo, "High Ep-CAM expression is associated with poor prognosis in node-positive breast cancer" 2004 Breast Cancer Res Treat., 86(3):207-13.

Steel, "Interleukin-15 biology and its therapeutic implications in cancer" 2012 Trends Pharmacol Sci., 33: 35-41.

Stein, "Novel conjugates of single-chain Fv antibody fragments specific for stem cell antigen CD123 mediate potent death of acute myeloid leukaemia cells" 2010 Br J Haematol., 148;879-885.

(56)          References Cited

OTHER PUBLICATIONS

Strohlein, "Immunotherapy of peritoneal carcinomatosis with the antibody catumaxomab in colon, gastric, or pancreatic cancer: an open-label, multicenter, phase I/II trial" 2011 Onkologie., 34(3):101-8. doi:10.1159/000324667.

Trentin, "Interleukin-15 promotes the growth of leukemic cells of patients with B-cell chronic lymphoproliferative disorders" 1996 Blood, 87(8):3327-35.

Trzpis, "Epithelial cell adhesion molecule: more than a carcinoma marker and adhesion molecule" 2007 Am J Pathol., 171(2):386-95.

Vallera, "Heterodimeric bispecific single-chain variable-fragment antibodies against EpCAM and CD16 induce effective antibody-dependent cellular cytotoxicity against human carcinoma cells" 2013 Cancer Biother Radiopharm., (4):274-82.

Vallera, "Genetic alteration of a bispecific ligand-directed toxin targeting human CD19 and CD22 receptors resulting in improved efficacy against systemic B cell malignancy" 2009 Leuk Res., 33:1233-42.

Vallera, "Molecular modification of a recombinant, bivalent anti-human CD3 immunotoxin (Bic3) results in reduced in vivo toxicity in mice" 2005 Leuk Res., 29:331-41.

Vallera, "IL-15 Trispecific Killer Engagers (TrikEs) Make Natural Killer Cells Specific to CD33+ Targets While Also Inducing Persistence, In Vivo Expansion, and Enhanced Function" Feb. 2016 Clin Cancer Res., 22(14):3440-3450.

Verneris, "Mismatch Is Associated with Worse Outcomes after Unrelated Donor Reduced-Intensity Conditioning Hematopoietic Cell Transplantation: An Analysis from the Center for International Blood and Marrow Transplant Research" 2015 Biol Blood Marrow Transplant, 21:1783-9.

Vincke, "General strategy to humanize a camelid single-domain antibody and identification of a universal humanized hanobody scaffold" 2009 J Biol Chem., 284(5):3273-3284.

Waldmann, "Interleukin-15 in the treatment of cancer" 2014 Expert Rev Clin Immunol., 10:1689-701.

Waldron, "Targeting tumor-initiating cancer cells with dCD133KDEL shows impressive tumor reductions in a xenotransplant model of human head and neck cancer" 2011 Mol Cancer Ther., 10:1829-38.

Weskamp, "Pathological neovascularization is reduced by inactivation of ADAM17 in endothelial cells but not in pericytes" Mar. 2010 Circ Res., (5): 932-40.

Wiernik, "Targeting natural killer cells to acute myeloid leukemia in vitro with a CD16 x 33 bispecific killer cell engager and ADAM17 inhibition" 2013 Clin Cancer Res., (14): 3844-55.

Wu, "Expression of interleukin 15 in primary adult acute lymphoblastic leukemia" 2010 Cancer, (116):387-92.

Yamamoto, "Circulating CD4+CD25+ regulatory T cells in patients with pancreatic cancer" 2012 Pancreas, 41(3):409-15. doi:10.1097/MPA.0b013e3182373a66.

Yokoyama, "Immune functions encoded by the natural killer gene complex" 2003 Nat Rev Immunol., (4):304-16.

Zambello, "Interleukin-15 triggers the proliferation and cytotoxicity of granular lymphocytes in patients with lymphoproliferative disease of granular lymphocytes" 1997 Blood, (89): 201-11.

Amet, "Insertion of the Designed Helical Linker Led to Increased Expression of Tf-based fusion proteins" Mar. 2009 Pharm. Res., 26(3):523-528.

Mccormick, "Immunization with an Interferon-g-gp120 Fusion Protein Induces Enhanced Immune Responses to Human Immunodeficiency Virus gp120" Nov. 2001 J. Infectious Dis., 184:1423-30.

Batra et al., "Recombinant anti-erbB2 immunotoxins containing Pseudomonas exotoxin", Proc. Natl. Acad. Sci. USA, vol. 89, Jul. 1992, pp. 5867-5871.

Behar et al., "Isolation and characterization of anti-FcγRIII (CD16) llama single-domain antibodies that activate natural killer cells", Protein Engineering, Design & Selection, vol. 21, No. 1, 2008, pp. 1-10.

Hoseini et al., "Acute myeloid leukemia targets for bispecific antibodies", Blood Cancer Journal, 7, e522, 2017, pp. 1-12.

International Preliminary Report on Patentability from PCT Application No. PCT/US2020/050851, dated Mar. 31, 2022, 7 pages.

International Preliminary Report on Patentability from PCT Application No. PCT/US2020/055468, dated Apr. 28, 2022, 7 pages.

International Search Report and Written Opinion from PCT Application No. PCT/US2020/050851, dated Jan. 5, 2021, 10 pages.

International Search Report and Written Opinion from PCT Application No. PCT/US2020/055468, dated Mar. 11, 2021, 11 pages.

Liu et al., "Development of Effective Therapeutics Targeting HER3 for Cancer Treatment", Biological Procedures Online, 21, 2019, 10 pages.

Tatusova et al., "Blast 2 Sequences, a new tool for comparing protein and nucleotide sequences", FEMS Microbiology Letters, 174, 1999, pp. 247-250.

Worsham et al., "Fine-mapping loss of gene architecture at the CDKN2B (p15INK4b), CDKN2A (p14ARF, p16INK4a), and MTAP genes in head and neck squamous cell carcinoma", Arch Otolaryngol Head Neck Surg., vol. 132 (4), Apr. 2006, pp. 409-415.

University of Minnesota, Arvindam et al., "CD16-IL15-CLEC12A Trispecific Killer Engager (TrikE) Drives NK Cell Expansion, Activation, and Antigen Specific Killing of Cancer Stem Cells in Acute Myeloid Leukemia" Poster, presented at ASH 2018—60th American Society of Hematology Annual Meeting and Exposition, San Diego, CA; Dec. 1-4, 2018; 1 page.

University of Minnesota, Felices et al. "CD16-IL15-CLEC12A Tri-specific Killer Engager (TriKE) drives NK cell expansion, persistence, and antigen specific killing of Cancer Stem Cells in MDS and AML" Poster, presented at the 17th meeting for the Society for Natural Immunity, San Antonio, TX; May 28-Jun. 1, 2018; 1 page.

Pasche et al., Cloning and characterization of novel tumor-targeting immunocytokines based on murine IL7, J Biotechnol, 2011; 154: 84-92.

Chen et al., "Enhancement and destruction of antibody function by somatic mutation: unequal occurrence is controlled by V gene combinatorial associations," EMBO Journal, 1995, 14(12): 2784-2794.

Colman, "Effects of amino acid sequence changes on antibody-antigen interactions," Research in Immunology, 1994, 145:33-36.

Rudikoff et al. "Single amino acid substitution altering antigen-binding specificity," Proc. Natl. Acad. Sci. USA, 1982, 79(6): 1979-1983.

Russian Office Action, dated Feb. 25, 2021, for Russian patent application No. 2018116565, 5 pages.

Felices et al., "Generation of BiKEs and TriKEs to improve NK cell-mediated targeting of tumor cells," Methods Mol Biol., 2016; 1441:333-346.

Miller, "Therapeutic applications: natural killer cells in the clinic," Hematology Am Soc Hematol Educ Program. 2013; 2013(1):247-253.

Office Action and Search Report, dated Sep. 8, 2020, for Japanese Patent Application No. 2018-517586, translated into English, 5 pages.

Office Action and Search Report, dated Nov. 3, 2020, for Russian Patent Application No. 2018116565, including English translation, 20 pages.

Almagro et al., "Humanization of Antibodies," Frontiers in Bioscience, 2008; 13:1619-1633.

International Patent Application No. PCT/US2016/055722, filed Oct. 6, 2016 International Search Report / Written Opinion issued Feb. 17, 2017; 15 pages.

Schmohl, "Enhanced ADCC and NK Cell Activation of an Anticarcinoma Bispecific Antibody by Genetic Insertion of a Modified IL-15 Cross-linker" Jul. 2016 Molecular Therapy, 24(7):1312-22. doi: 10.1038/mt.2016.88.

International Patent Application No. PCT/US2016/055722, filed Oct. 6, 2016 International Preliminary Report on Patentability issued Apr. 19, 2018; 8 pages.

European Search Report for European Patent Application No. 16854310.6, issued Jul. 5, 2019. 14 pgs.

Alderson, "Clinical cancer therapy by NK cells via antibody-dependent cell-mediated cytotoxicity" 2011 Journal of biomedicine & biotechnology, 2011:379123.

(56) References Cited

OTHER PUBLICATIONS

Artis, "The biology of innate lymphoid cells" 2015 Nature, 517:293-301.

American Type Culture Collection, "HT29, ATCC HTB38," organism: *Homo sapiens*, human; [online] Manassas, VA [retrieved on Apr. 4, 2019] from the Internet: https://www.ncbi.nlm.nih.gov/nuccore/EF561291.1. 3 pgs.

American Type Culture Collection, "ATCC HL-60, CCI-240, a CD33+ human acute promyelocytic leukemia cell line," organism: *Homo sapiens*, human; [online] Manassas, VA [retrieved on Apr. 4, 2019 from the Internet: https://www.atcc.org/~/ps/CCL-240.ashx. 3 pgs.

Bachanova, "Clearance of acute myeloid leukemia by haploidentical natural killer cells is improved using IL-2 diphtheria toxin fusion protein" 2014 Blood, 123:3855-63.

Badolato, "Interleukin-15 (IL-15) induces IL-8 and monocyte chemotactic protein 1 production in human monocytes" 1997 Blood, 90: 2804-9.

Baeuerle, "EpCAM (CD326) finding its role in cancer" 2007 Br J Cancer, 96(3):417-23.

Bargou, "Tumor regression in cancer patients by very low doses of a T cell-engaging antibody" 2008 Science, 321(5891):974-7.

Barrett, "Toxicity management for patients receiving novel T-cell engaging therapies" 2014 Curr Opin Pediatr., 26(1):43-9.

Basak, "Interleukin 15 augments antitumor activity of cytokine gene-modified melanoma cell vaccines in a murine model" 2008 Oncol Rep., 19(5):1173-9.

Becknell, "Interleukin-2, interleukin-15, and their roles in human natural killer cells" 2005 Adv Immunol., 86: 209-39.

Bell, "Sustained in vivo signaling by long-lived IL-2 induces prolonged increases of regulatory T cells" 2015 J Autoimmun., 56:66-80.

Berger, "Safety and immunologic effects of IL-15 administration in nonhuman primates" 2009 Blood, (12):2417-2426.

Bezan, "Systemic effect of catumaxomab in a patient with metastasized colorectal cancer: a case report" 2013 BMC Cancer, 13:618. doi:10.1186/1471-2407-13-618.

Budagian, "Reverse signaling through membrane-bound interleukin-15" 2004 J Biol Chem., 279: 42192-2.

Budagian, "IL-15/IL-15 receptor biology: a guided tour through an expanding universe" 2006 Cytokine Growth Factor Rev., 17: 259-80.

Caligiuri, "Functional consequences of interleukin 2 receptor expression on resting human lymphocytes. Identification of a novel natural killer cell subset with high affinity receptors" 1990 J Exp Med., 171(5):1509-26.

Carson, "Interleukin (IL) 15 is a novel cytokine that activates human natural killer cells via components of the IL-2 receptor" 1994 J Exp Med., 180(4):1395-403.

Conlon, "Redistribution, hyperproliferation, activation of natural killer cells and CD8 T cells, and cytokine production during first-in-human clinical trial of recombinant human interleukin-15 in patients with cancer" 2015 J Clin Oncol., 33(1):74-82.

Connor, "Ex vivo evaluation of anti-EpCAM immunocytokine huKS-IL2 in ovarian cancer" 2004 J Immunother., 27(3):211-9.

Cooper, "Human natural killer cells: a unique innate immunoregulatory role for the CD56(bright) subset" 2001 Blood, 97(10):3146-51.

Ensinger, "EpCAM overexpression in thyroid carcinomas: a histopathological study of 121 cases" 2006 J Immunother., 29(5):569-73.

Fehniger, "Differential cytokine and chemokine gene expression by human NK cells following activation with IL-18 or L-15 in combination with IL-12: implications for the innate immune response" 1999 J Immunol., 162(8):4511-20.

Fehniger, "Fatal leukemia in interleukin 15 transgenic mice follows early expansions in natural killer and memory phenotype CD8+ T cells" 2001 J Exp Med., (193): 219-31.

Felices, "CD16-IL 15-CD33 Trispecific Killer Engager (TriKE) induces NK cell expansion, persistence, and myeloid plast antigen specific killing." May 2016 The Journal of Immunology, 196(1 Supplement):75.8.

Finco, "Cytokine release assays: current practices and future directions" 2014 Cytokine, 66(2):143-55. doi: 10.1016/j.cyto.2013.12.009. Epub Jan. 10, 2014. Review.

Finney, "Activation of resting human primary T cells with chimeric receptors: costimulation from CD28, inducible costimulator, CD134, and CD137 in series with signals from the TCR zeta chain" 2004 J Immunol., 172(1):104-13.

Fogh, "One hundred and twenty-seven cultured human tumor cell lines producing tumors in nude mice" 1977 J Natl Cancer Inst., 59(1):221-6.

Foley, "The biology of NK cells and their receptors affects clinical outcomes after hematopoietic cell transplantation (HCT)" 2014 Immunol Rev., 258:45-63.

Foley, "NK cell education after allogeneic transplantation: dissociation between recovery of cytokine-producing and cytotoxic functions" 2011 Blood, 118:2784-92.

Gastl, "Ep-CAM overexpression in breast cancer as a predictor of survival" 2000 Lancet, 356(9246):1981-2.

Gleason, "Bispecific and Trispecific Killer Cell Engagers Directly Activate Human NK Cells through CD16 Signaling and Induce Cytotoxicity and Cytokine Production" Dec. 2012 Molecular Cancer Therapeutics, 11(12):2674-2684.

Gleason, "The Functional Role of the Activating Receptors Tim-3 and Cd16 in Human Natural Killer (NK) Cell Biology" dissertation University of Minnesota, Sep. 2012. 199 pages.

Gleason, "CD16xCD33 bispecific killer cell engager (BiKE) activates NK cells against primary MDS and MDSC CD33+ targets" 2014 Blood, (19):3016-26.

Grupp, "Chimeric antigen receptor-modified T cells for acute lymphoid leukemia" 2013 N Engl J Med., 368(16):1509-18.

Gutzmer, "A tumor-associated glycoprotein that blocks MHC class II-dependent antigen presentation by dendritic cells" 2004 J Immunol., 173(2):1023-32.

Examination Report issued Aug. 26, 2025, Australian Patent Application No. 2023233318; 5 pages.

Fig. 13

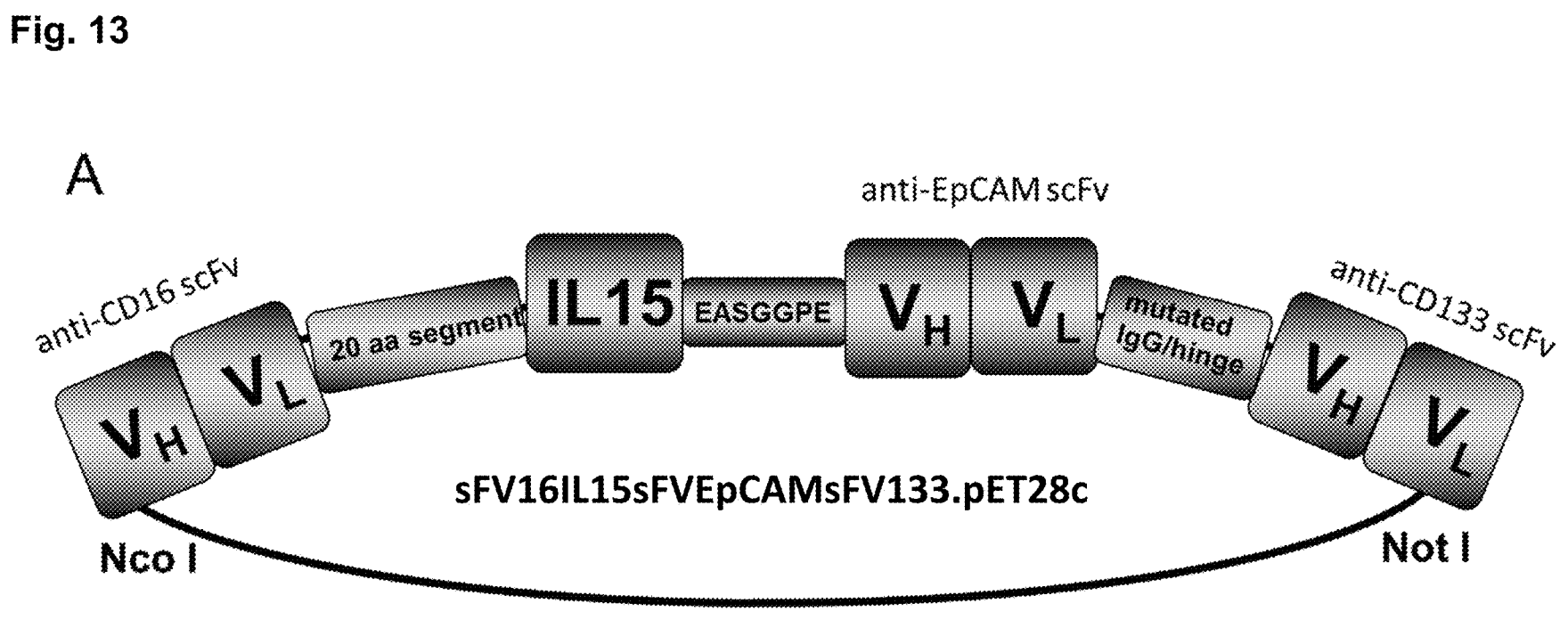

A anti-CD133 scFv anti-EpCAM scFv anti-CD16 scFv $V_L$ $V_H$ mutated IgG/hinge $V_L$ $V_H$

EASGGPE

IL15

20 aa segment $V_L$ $V_H$

Not I

Nco I sFV16IL15sFVEpCAMsFV133.pET28c

Fig. 21

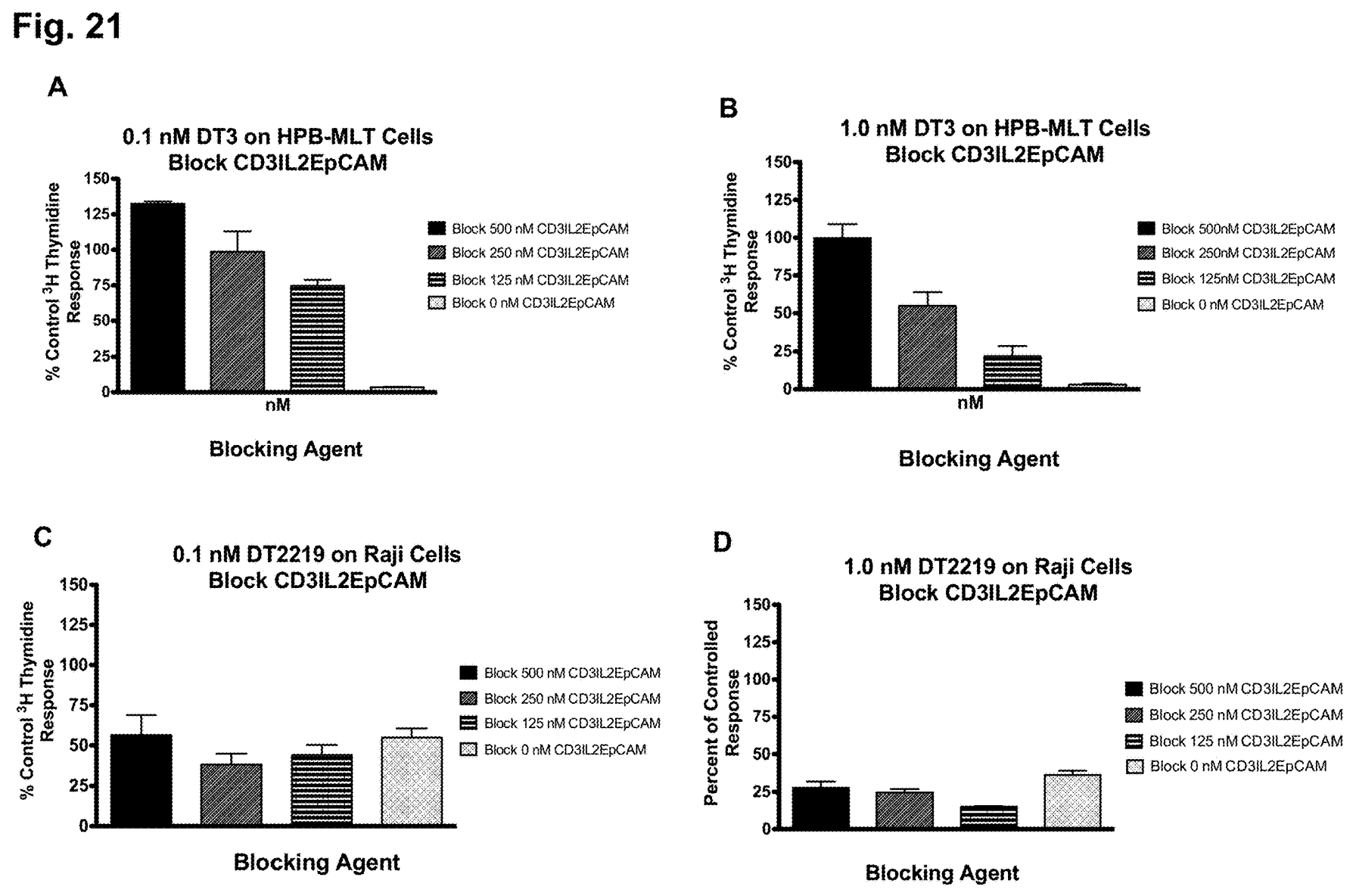

A — 0.1 nM DT3 on HPB-MLT Cells Block CD3iL2EpCAM

■ Block 500 nM CD3iL2EpCAM
▨ Block 250 nM CD3iL2EpCAM
▥ Block 125 nM CD3iL2EpCAM
▨ Block 0 nM CD3iL2EpCAM

B — 1.0 nM DT3 on HPB-MLT Cells Block CD3iL2EpCAM

■ Block 500nM CD3iL2EpCAM
▨ Block 250nM CD3iL2EpCAM
▥ Block 125nM CD3iL2EpCAM
▨ Block 0 nM CD3iL2EpCAM

C — 0.1 nM DT2219 on Raji Cells Block CD3iL2EpCAM

■ Block 500 nM CD3iL2EpCAM
▨ Block 250 nM CD3iL2EpCAM
▥ Block 125 nM CD3iL2EpCAM
▨ Block 0 nM CD3iL2EpCAM

D — 1.0 nM DT2219 on Raji Cells Block CD3iL2EpCAM

■ Block 500 nM CD3iL2EpCAM
▨ Block 250 nM CD3iL2EpCAM
▥ Block 125 nM CD3iL2EpCAM
▨ Block 0 nM CD3iL2EpCAM Fig. 22
A
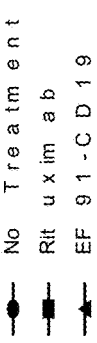
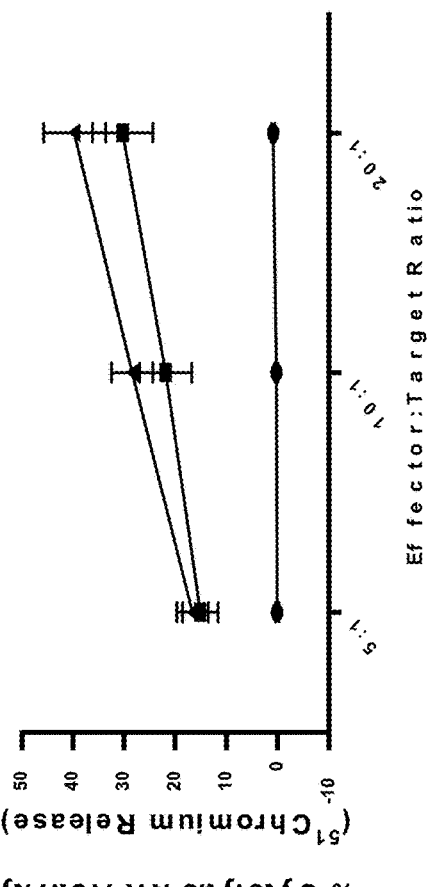
B
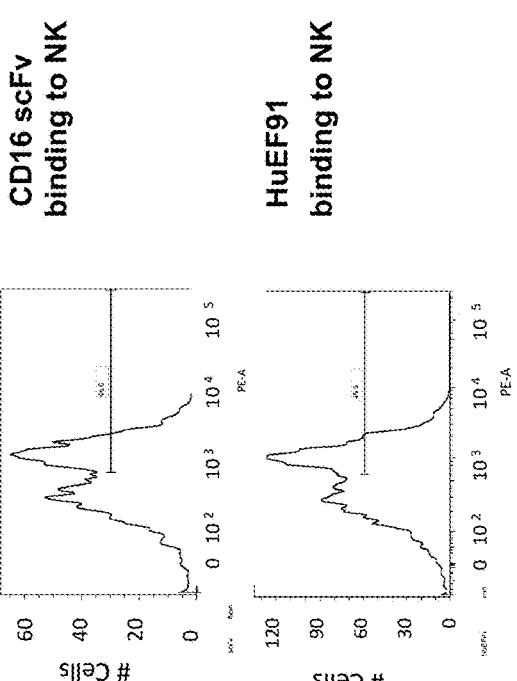

SEQUENCE LISTING

<160> NUMBER OF SEQ ID NOS: 20

<210> SEQ ID NO 1
<211> LENGTH: 623
<212> TYPE: PRT
<213> ORGANISM: Artificial
<220> FEATURE:
<223> OTHER INFORMATION: Polypeptide

<400> SEQUENCE: 1

Met Glu Val Gln Leu Val Glu Ser Gly Gly Gly Val Val Arg Pro Gly
1               5                   10                  15

Gly Ser Leu Arg Leu Ser Cys Ala Ala Ser Gly Phe Thr Phe Asp Asp
                20                  25                  30

Tyr Gly Met Ser Trp Val Arg Gln Ala Pro Gly Lys Gly Leu Glu Trp
            35                  40                  45

Val Ser Gly Ile Asn Trp Asn Gly Gly Ser Thr Gly Tyr Ala Asp Ser
        50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Gly Arg Ser Leu Leu Phe Asp Tyr Trp Gly Gln Gly Thr
            100                 105                 110

Leu Val Thr Val Ser Arg Gly Gly Gly Gly Ser Gly Gly Gly Gly Ser
        115                 120                 125

Gly Gly Gly Gly Ser Ser Glu Leu Thr Gln Asp Pro Ala Val Ser Val
    130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Asp Arg
            180                 185                 190

Phe Ser Gly Ser Ser Ser Gly Asn Thr Ala Ser Leu Thr Ile Thr Gly
            195                 200                 205

Ala Gln Ala Glu Asp Glu Ala Asp Tyr Tyr Cys Asn Ser Arg Asp Ser
    210                 215                 220

Ser Gly Asn His Val Val Phe Gly Gly Gly Thr Lys Leu Thr Val Leu
225                 230                 235                 240

Pro Ser Gly Gln Ala Gly Ala Ala Ala Ser Glu Ser Leu Phe Val Ser
            245                 250                 255

Asn His Ala Tyr Asn Trp Val Asn Val Ile Ser Asp Leu Lys Lys Ile
            260                 265                 270

Glu Asp Leu Ile Gln Ser Met His Ile Asp Ala Thr Leu Tyr Thr Glu
        275                 280                 285

Ser Asp Val His Pro Ser Cys Lys Val Thr Ala Met Lys Cys Phe Leu
    290                 295                 300

Leu Glu Leu Gln Val Ile Ser Leu Glu Ser Gly Asp Ala Ser Ile His
305                 310                 315                 320

Asp Thr Val Glu Asn Leu Ile Ile Leu Ala Asn Asp Ser Leu Ser Ser
            325                 330                 335

Asn Gly Asn Val Thr Glu Ser Gly Cys Lys Glu Cys Glu Glu Leu Glu
            340                 345                 350

Glu Lys Asn Ile Lys Glu Phe Leu Gln Ser Phe Val His Ile Val Gln
        355                 360                 365

Met Phe Ile Asn Thr Ser Glu Ala Ser Gly Gly Pro Glu Gln Val Gln
    370                 375                 380

Leu Val Gln Ser Gly Ala Glu Val Lys Lys Pro Gly Ser Ser Val Lys
385                 390                 395                 400

Val Ser Cys Lys Ala Ser Gly Tyr Thr Phe Thr Asp Tyr Asn Met His

-continued

```
                405                    410                    415
Trp Val Arg Gln Ala Pro Gly Gln Gly Leu Glu Trp Ile Gly Tyr Ile
            420                    425                    430

Tyr Pro Tyr Asn Gly Gly Thr Gly Tyr Asn Gln Lys Phe Lys Ser Lys
            435                    440                    445

Ala Thr Ile Thr Ala Asp Glu Ser Thr Asn Thr Ala Tyr Met Glu Leu
    450                    455                    460

Ser Ser Leu Arg Ser Glu Asp Thr Ala Val Tyr Tyr Cys Ala Arg Gly
465                    470                    475                    480

Arg Pro Ala Met Asp Tyr Trp Gly Gln Gly Thr Leu Val Thr Val Ser
                485                    490                    495

Ser Gly Gly Gly Gly Ser Gly Gly Gly Ser Gly Gly Gly Gly Ser
                500                    505                    510

Asp Ile Gln Met Thr Gln Ser Pro Ser Ser Leu Ser Ala Ser Val Gly
            515                    520                    525

Asp Arg Val Thr Ile Thr Cys Arg Ala Ser Glu Ser Val Asp Asn Tyr
    530                    535                    540

Gly Ile Ser Phe Met Asn Trp Phe Gln Gln Lys Pro Gly Lys Ala Pro
545                    550                    555                    560

Lys Leu Leu Ile Tyr Ala Ala Ser Asn Gln Gly Ser Gly Val Pro Ser
                565                    570                    575

Arg Phe Ser Gly Ser Gly Ser Gly Thr Asp Phe Thr Leu Thr Ile Ser
                580                    585                    590

Ser Leu Gln Pro Asp Asp Phe Ala Thr Tyr Tyr Cys Gln Gln Ser Lys
            595                    600                    605

Glu Val Pro Trp Thr Phe Gly Gln Gly Thr Lys Val Glu Ile Lys
    610                    615                    620
```

<210> SEQ ID NO 2
<211> LENGTH: 502
<212> TYPE: PRT
<213> ORGANISM: Artificial
<220> FEATURE:
<223> OTHER INFORMATION: Polypeptide

<400> SEQUENCE: 2

```
Met Glu Val Gln Leu Val Glu Ser Gly Gly Gly Val Val Arg Pro Gly
1               5                   10                  15

Gly Ser Leu Arg Leu Ser Cys Ala Ala Ser Gly Phe Thr Phe Asp Asp
            20                  25                  30

Tyr Gly Met Ser Trp Val Arg Gln Ala Pro Gly Lys Gly Leu Glu Trp
        35                  40                  45

Val Ser Gly Ile Asn Trp Asn Gly Gly Ser Thr Gly Tyr Ala Asp Ser
    50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Gly Arg Ser Leu Leu Phe Asp Tyr Trp Gly Gln Gly Thr
            100                 105                 110

Leu Val Thr Val Ser Arg Gly Gly Gly Gly Ser Gly Gly Gly Gly Ser
            115                 120                 125

Gly Gly Gly Gly Ser Ser Glu Leu Thr Gln Asp Pro Ala Val Ser Val
    130                 135                 140

Ala Leu Gly Gln Thr Val Arg Ile Thr Cys Gln Gly Asp Ser Leu Arg
```

```
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Asp Arg
                180                 185                 190

Phe Ser Gly Ser Ser Ser Gly Asn Thr Ala Ser Leu Thr Ile Thr Gly
                195                 200                 205

Ala Gln Ala Glu Asp Glu Ala Asp Tyr Tyr Cys Asn Ser Arg Asp Ser
                210                 215                 220

Ser Gly Asn His Val Val Phe Gly Gly Gly Thr Lys Leu Thr Val Leu
225                 230                 235                 240

Pro Ser Gly Gln Ala Gly Ala Ala Ala Ser Glu Ser Leu Phe Val Ser
                245                 250                 255

Asn His Ala Tyr Gln Val Gln Leu Val Gln Ser Gly Ala Glu Val Lys
                260                 265                 270

Lys Pro Gly Ser Ser Val Lys Val Ser Cys Lys Ala Ser Gly Tyr Thr
                275                 280                 285

Phe Thr Asp Tyr Asn Met His Trp Val Arg Gln Ala Pro Gly Gln Gly
                290                 295                 300

Leu Glu Trp Ile Gly Tyr Ile Tyr Pro Tyr Asn Gly Gly Thr Gly Tyr
305                 310                 315                 320

Asn Gln Lys Phe Lys Ser Lys Ala Thr Ile Thr Ala Asp Glu Ser Thr
                325                 330                 335

Asn Thr Ala Tyr Met Glu Leu Ser Ser Leu Arg Ser Glu Asp Thr Ala
                340                 345                 350

Val Tyr Tyr Cys Ala Arg Gly Arg Pro Ala Met Asp Tyr Trp Gly Gln
                355                 360                 365

Gly Thr Leu Val Thr Val Ser Ser Gly Gly Gly Gly Ser Gly Gly Gly
                370                 375                 380

Gly Ser Gly Gly Gly Gly Ser Asp Ile Gln Met Thr Gln Ser Pro Ser
385                 390                 395                 400

Ser Leu Ser Ala Ser Val Gly Asp Arg Val Thr Ile Thr Cys Arg Ala
                405                 410                 415

Ser Glu Ser Val Asp Asn Tyr Gly Ile Ser Phe Met Asn Trp Phe Gln
                420                 425                 430

Gln Lys Pro Gly Lys Ala Pro Lys Leu Leu Ile Tyr Ala Ala Ser Asn
                435                 440                 445

Gln Gly Ser Gly Val Pro Ser Arg Phe Ser Gly Ser Gly Ser Gly Thr
                450                 455                 460

Asp Phe Thr Leu Thr Ile Ser Ser Leu Gln Pro Asp Asp Phe Ala Thr
465                 470                 475                 480

Tyr Tyr Cys Gln Gln Ser Lys Glu Val Pro Trp Thr Phe Gly Gln Gly
                485                 490                 495

Thr Lys Val Glu Ile Lys
                500
```

<210> SEQ ID NO 3
<211> LENGTH: 20
<212> TYPE: PRT
<213> ORGANISM: Artificial
<220> FEATURE:
<223> OTHER INFORMATION: Polypeptide

<400> SEQUENCE: 3

Pro Ser Gly Gln Ala Gly Ala Ala Ala Ser Glu Ser Leu Phe Val Ser

```
1                    5                    10                   15

Asn His Ala Tyr
             20
```

```
<210> SEQ ID NO 4
<211> LENGTH: 7
<212> TYPE: PRT
<213> ORGANISM: Artificial
<220> FEATURE:
<223> OTHER INFORMATION: Polypeptide

<400> SEQUENCE: 4

Glu Ala Ser Gly Gly Pro Glu
1               5
```

```
<210> SEQ ID NO 5
<211> LENGTH: 596
<212> TYPE: PRT
<213> ORGANISM: Artificial
<220> FEATURE:
<223> OTHER INFORMATION: Polypeptide

<400> SEQUENCE: 5

Met Glu Val Gln Leu Val Glu Ser Gly Gly Gly Val Val Arg Pro Gly
1               5                   10                  15

Gly Ser Leu Arg Leu Ser Cys Ala Ala Ser Gly Phe Thr Phe Asp Asp
             20                  25                  30

Tyr Gly Met Ser Trp Val Arg Gln Ala Pro Gly Lys Gly Leu Glu Trp
         35                  40                  45

Val Ser Gly Ile Asn Trp Asn Gly Gly Ser Thr Gly Tyr Ala Asp Ser
    50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Gly Arg Ser Leu Leu Phe Asp Tyr Trp Gly Gln Gly Thr
            100                 105                 110

Leu Val Thr Val Ser Arg Gly Gly Gly Gly Ser Gly Gly Gly Gly Ser
        115                 120                 125

Gly Gly Gly Gly Ser Ser Glu Leu Thr Gln Asp Pro Ala Val Ser Val
    130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Asp Arg
                180                 185                 190

Phe Ser Gly Ser Ser Ser Gly Asn Thr Ala Ser Leu Thr Ile Thr Gly
            195                 200                 205

Ala Gln Ala Glu Asp Glu Ala Asp Tyr Tyr Cys Asn Ser Arg Asp Ser
        210                 215                 220

Ser Gly Asn His Val Val Phe Gly Gly Gly Thr Lys Leu Thr Val Leu
225                 230                 235                 240

Asn Trp Val Asn Val Ile Ser Asp Leu Lys Lys Ile Glu Asp Leu Ile
                245                 250                 255

Gln Ser Met His Ile Asp Ala Thr Leu Tyr Thr Glu Ser Asp Val His
            260                 265                 270
```

-continued

```
Pro Ser Cys Lys Val Thr Ala Met Lys Cys Phe Leu Leu Glu Leu Gln
        275                 280             285

Val Ile Ser Leu Glu Ser Gly Asp Ala Ser Ile His Asp Thr Val Glu
        290                 295             300

Asn Leu Ile Ile Leu Ala Asn Asp Ser Leu Ser Ser Asn Gly Asn Val
305                 310                 315                 320

Thr Glu Ser Gly Cys Lys Glu Cys Glu Glu Leu Glu Glu Lys Asn Ile
                325                 330                 335

Lys Glu Phe Leu Gln Ser Phe Val His Ile Val Gln Met Phe Ile Asn
                340                 345                 350

Thr Ser Gln Val Gln Leu Val Gln Ser Gly Ala Glu Val Lys Lys Pro
                355                 360                 365

Gly Ser Ser Val Lys Val Ser Cys Lys Ala Ser Gly Tyr Thr Phe Thr
        370                 375                 380

Asp Tyr Asn Met His Trp Val Arg Gln Ala Pro Gly Gln Gly Leu Glu
385                 390                 395                 400

Trp Ile Gly Tyr Ile Tyr Pro Tyr Asn Gly Gly Thr Gly Tyr Asn Gln
                405                 410                 415

Lys Phe Lys Ser Lys Ala Thr Ile Thr Ala Asp Glu Ser Thr Asn Thr
                420                 425                 430

Ala Tyr Met Glu Leu Ser Ser Leu Arg Ser Glu Asp Thr Ala Val Tyr
                435                 440                 445

Tyr Cys Ala Arg Gly Arg Pro Ala Met Asp Tyr Trp Gly Gln Gly Thr
        450                 455                 460

Leu Val Thr Val Ser Ser Gly Gly Gly Gly Ser Gly Gly Gly Gly Ser
465                 470                 475                 480

Gly Gly Gly Gly Ser Asp Ile Gln Met Thr Gln Ser Pro Ser Ser Leu
                485                 490                 495

Ser Ala Ser Val Gly Asp Arg Val Thr Ile Thr Cys Arg Ala Ser Glu
                500                 505                 510

Ser Val Asp Asn Tyr Gly Ile Ser Phe Met Asn Trp Phe Gln Gln Lys
                515                 520                 525

Pro Gly Lys Ala Pro Lys Leu Leu Ile Tyr Ala Ala Ser Asn Gln Gly
        530                 535                 540

Ser Gly Val Pro Ser Arg Phe Ser Gly Ser Gly Ser Gly Thr Asp Phe
545                 550                 555                 560

Thr Leu Thr Ile Ser Ser Leu Gln Pro Asp Asp Phe Ala Thr Tyr Tyr
                565                 570                 575

Cys Gln Gln Ser Lys Glu Val Pro Trp Thr Phe Gly Gln Gly Thr Lys
                580                 585                 590

Val Glu Ile Lys
        595
```

<210> SEQ ID NO 6
<211> LENGTH: 624
<212> TYPE: PRT
<213> ORGANISM: Artificial
<220> FEATURE:
<223> OTHER INFORMATION: Polypeptide

<400> SEQUENCE: 6

```
Met Glu Asn Trp Val Asn Val Ile Ser Asp Leu Lys Lys Ile Glu Asp
1               5                   10                  15

Leu Ile Gln Ser Met His Ile Asp Ala Thr Leu Tyr Thr Glu Ser Asp
                20                  25                  30
```

-continued

```
Val His Pro Ser Cys Lys Val Thr Ala Met Lys Cys Phe Leu Leu Glu
        35              40              45

Leu Gln Val Ile Ser Leu Glu Ser Gly Asp Ala Ser Ile His Asp Thr
    50              55              60

Val Glu Asn Leu Ile Ile Leu Ala Asn Asp Ser Leu Ser Ser Asn Gly
65              70              75              80

Asn Val Thr Glu Ser Gly Cys Lys Glu Cys Glu Glu Leu Glu Glu Lys
            85              90              95

Asn Ile Lys Glu Phe Leu Gln Ser Phe Val His Ile Val Gln Met Phe
            100             105             110

Ile Asn Thr Ser Pro Ser Gly Gln Ala Gly Ala Ala Ala Ser Glu Ser
            115             120             125

Leu Phe Val Ser Asn His Ala Tyr Glu Val Gln Leu Val Glu Ser Gly
    130             135             140

Gly Gly Val Val Arg Pro Gly Gly Ser Leu Arg Leu Ser Cys Ala Ala
145             150             155             160

Ser Gly Phe Thr Phe Asp Asp Tyr Gly Met Ser Trp Val Arg Gln Ala
            165             170             175

Pro Gly Lys Gly Leu Glu Trp Val Ser Gly Ile Asn Trp Asn Gly Gly
            180             185             190

Ser Thr Gly Tyr Ala Asp Ser Val Lys Gly Arg Phe Thr Ile Ser Arg
            195             200             205

Asp Asn Ala Lys Asn Ser Leu Tyr Leu Gln Met Asn Ser Leu Arg Ala
    210             215             220

Glu Asp Thr Ala Val Tyr Tyr Cys Ala Arg Gly Arg Ser Leu Leu Phe
225             230             235             240

Asp Tyr Trp Gly Gln Gly Thr Leu Val Thr Val Ser Arg Gly Gly Gly
            245             250             255

Gly Ser Gly Gly Gly Gly Ser Gly Gly Gly Gly Ser Ser Glu Leu Thr
            260             265             270

Gln Asp Pro Ala Val Ser Val Ala Leu Gly Gln Thr Val Arg Ile Thr
            275             280             285

Cys Gln Gly Asp Ser Leu Arg Ser Tyr Tyr Ala Ser Trp Tyr Gln Gln
    290             295             300

Lys Pro Gly Gln Ala Pro Val Leu Val Ile Tyr Gly Lys Asn Asn Arg
305             310             315             320

Pro Ser Gly Ile Pro Asp Arg Phe Ser Gly Ser Ser Ser Gly Asn Thr
            325             330             335

Ala Ser Leu Thr Ile Thr Gly Ala Gln Ala Glu Asp Glu Ala Asp Tyr
            340             345             350

Tyr Cys Asn Ser Arg Asp Ser Ser Gly Asn His Val Val Phe Gly Gly
            355             360             365

Gly Thr Lys Leu Thr Val Leu Glu Ala Ser Gly Gly Pro Glu Gln Val
    370             375             380

Gln Leu Val Gln Ser Gly Ala Glu Val Lys Lys Pro Gly Ser Ser Val
385             390             395             400

Lys Val Ser Cys Lys Ala Ser Gly Tyr Thr Phe Thr Asp Tyr Asn Met
            405             410             415

His Trp Val Arg Gln Ala Pro Gly Gln Gly Leu Glu Trp Ile Gly Tyr
            420             425             430

Ile Tyr Pro Tyr Asn Gly Gly Thr Gly Tyr Asn Gln Lys Phe Lys Ser
            435             440             445

Lys Ala Thr Ile Thr Ala Asp Glu Ser Thr Asn Thr Ala Tyr Met Glu
```

-continued

```
        450              455              460

Leu Ser Ser Leu Arg Ser Glu Asp Thr Ala Val Tyr Tyr Cys Ala Arg
465              470              475              480

Gly Arg Pro Ala Met Asp Tyr Trp Gly Gln Gly Thr Leu Val Thr Val
                485              490              495

Ser Ser Gly Gly Gly Gly Ser Gly Gly Gly Ser Gly Gly Gly Gly
            500              505              510

Ser Asp Ile Gln Met Thr Gln Ser Pro Ser Ser Leu Ser Ala Ser Val
            515              520              525

Gly Asp Arg Val Thr Ile Thr Cys Arg Ala Ser Glu Ser Val Asp Asn
    530              535              540

Tyr Gly Ile Ser Phe Met Asn Trp Phe Gln Gln Lys Pro Gly Lys Ala
545              550              555              560

Pro Lys Leu Leu Ile Tyr Ala Ala Ser Asn Gln Gly Ser Gly Val Pro
                565              570              575

Ser Arg Phe Ser Gly Ser Gly Ser Gly Thr Asp Phe Thr Leu Thr Ile
            580              585              590

Ser Ser Leu Gln Pro Asp Asp Phe Ala Thr Tyr Tyr Cys Gln Gln Ser
            595              600              605

Lys Glu Val Pro Trp Thr Phe Gly Gln Gly Thr Lys Val Glu Ile Lys
        610              615              620

<210> SEQ ID NO 7
<211> LENGTH: 623
<212> TYPE: PRT
<213> ORGANISM: Artificial
<220> FEATURE:
<223> OTHER INFORMATION: Polypeptide

<400> SEQUENCE: 7

Met Glu Val Gln Leu Val Glu Ser Gly Gly Gly Val Val Arg Pro Gly
1               5              10              15

Gly Ser Leu Arg Leu Ser Cys Ala Ala Ser Gly Phe Thr Phe Asp Asp
            20              25              30

Tyr Gly Met Ser Trp Val Arg Gln Ala Pro Gly Lys Gly Leu Glu Trp
            35              40              45

Val Ser Gly Ile Asn Trp Asn Gly Gly Ser Thr Gly Tyr Ala Asp Ser
    50              55              60

Val Lys Gly Arg Phe Thr Ile Ser Arg Asp Asn Ala Lys Asn Ser Leu
65              70              75              80

Tyr Leu Gln Met Asn Ser Leu Arg Ala Glu Asp Thr Ala Val Tyr Tyr
                85              90              95

Cys Ala Arg Gly Arg Ser Leu Leu Phe Asp Tyr Trp Gly Gln Gly Thr
            100              105              110

Leu Val Thr Val Ser Arg Gly Gly Gly Gly Ser Gly Gly Gly Gly Ser
            115              120              125

Gly Gly Gly Gly Ser Ser Glu Leu Thr Gln Asp Pro Ala Val Ser Val
    130              135              140

Ala Leu Gly Gln Thr Val Arg Ile Thr Cys Gln Gly Asp Ser Leu Arg
145              150              155              160

Ser Tyr Tyr Ala Ser Trp Tyr Gln Gln Lys Pro Gly Gln Ala Pro Val
                165              170              175

Leu Val Ile Tyr Gly Lys Asn Asn Arg Pro Ser Gly Ile Pro Asp Arg
            180              185              190

Phe Ser Gly Ser Ser Ser Gly Asn Thr Ala Ser Leu Thr Ile Thr Gly
```

-continued

```
                195                 200                 205

Ala Gln Ala Glu Asp Glu Ala Asp Tyr Tyr Cys Asn Ser Arg Asp Ser
    210                 215                 220

Ser Gly Asn His Val Val Phe Gly Gly Gly Thr Lys Leu Thr Val Leu
225                 230                 235                 240

Pro Ser Gly Gln Ala Gly Ala Ala Ala Ser Glu Ser Leu Phe Val Ser
                245                 250                 255

Asn His Ala Tyr Gln Val Gln Leu Val Gln Ser Gly Ala Glu Val Lys
                260                 265                 270

Lys Pro Gly Ser Ser Val Lys Val Ser Cys Lys Ala Ser Gly Tyr Thr
                275                 280                 285

Phe Thr Asp Tyr Asn Met His Trp Val Arg Gln Ala Pro Gly Gln Gly
    290                 295                 300

Leu Glu Trp Ile Gly Tyr Ile Tyr Pro Tyr Asn Gly Gly Thr Gly Tyr
305                 310                 315                 320

Asn Gln Lys Phe Lys Ser Lys Ala Thr Ile Thr Ala Asp Glu Ser Thr
                325                 330                 335

Asn Thr Ala Tyr Met Glu Leu Ser Ser Leu Arg Ser Glu Asp Thr Ala
                340                 345                 350

Val Tyr Tyr Cys Ala Arg Gly Arg Pro Ala Met Asp Tyr Trp Gly Gln
                355                 360                 365

Gly Thr Leu Val Thr Val Ser Ser Gly Gly Gly Ser Gly Gly Gly
    370                 375                 380

Gly Ser Gly Gly Gly Gly Ser Asp Ile Gln Met Thr Gln Ser Pro Ser
385                 390                 395                 400

Ser Leu Ser Ala Ser Val Gly Asp Arg Val Thr Ile Thr Cys Arg Ala
                405                 410                 415

Ser Glu Ser Val Asp Asn Tyr Gly Ile Ser Phe Met Asn Trp Phe Gln
                420                 425                 430

Gln Lys Pro Gly Lys Ala Pro Lys Leu Leu Ile Tyr Ala Ala Ser Asn
                435                 440                 445

Gln Gly Ser Gly Val Pro Ser Arg Phe Ser Gly Ser Gly Ser Gly Thr
    450                 455                 460

Asp Phe Thr Leu Thr Ile Ser Ser Leu Gln Pro Asp Asp Phe Ala Thr
465                 470                 475                 480

Tyr Tyr Cys Gln Gln Ser Lys Glu Val Pro Trp Thr Phe Gly Gln Gly
                485                 490                 495

Thr Lys Val Glu Ile Lys Glu Ala Ser Gly Gly Pro Glu Asn Trp Val
                500                 505                 510

Asn Val Ile Ser Asp Leu Lys Lys Ile Glu Asp Leu Ile Gln Ser Met
    515                 520                 525

His Ile Asp Ala Thr Leu Tyr Thr Glu Ser Asp Val His Pro Ser Cys
    530                 535                 540

Lys Val Thr Ala Met Lys Cys Phe Leu Leu Glu Leu Gln Val Ile Ser
545                 550                 555                 560

Leu Glu Ser Gly Asp Ala Ser Ile His Asp Thr Val Glu Asn Leu Ile
                565                 570                 575

Ile Leu Ala Asn Asp Ser Leu Ser Ser Asn Gly Asn Val Thr Glu Ser
                580                 585                 590

Gly Cys Lys Glu Cys Glu Glu Leu Glu Glu Lys Asn Ile Lys Glu Phe
                595                 600                 605

Leu Gln Ser Phe Val His Ile Val Gln Met Phe Ile Asn Thr Ser
    610                 615                 620
```

-continued

```
<210> SEQ ID NO 8
<211> LENGTH: 634
<212> TYPE: PRT
<213> ORGANISM: Artificial
<220> FEATURE:
<223> OTHER INFORMATION: Polypeptide

<400> SEQUENCE: 8

Met Glu Val Gln Leu Val Glu Ser Gly Gly Gly Val Val Arg Pro Gly
1               5                   10                  15

Gly Ser Leu Arg Leu Ser Cys Ala Ala Ser Gly Phe Thr Phe Asp Asp
                20                  25                  30

Tyr Gly Met Ser Trp Val Arg Gln Ala Pro Gly Lys Gly Leu Glu Trp
            35                  40                  45

Val Ser Gly Ile Asn Trp Asn Gly Gly Ser Thr Gly Tyr Ala Asp Ser
        50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Gly Arg Ser Leu Leu Phe Asp Tyr Trp Gly Gln Gly Thr
            100                 105                 110

Leu Val Thr Val Ser Arg Gly Gly Gly Gly Ser Gly Gly Gly Gly Ser
        115                 120                 125

Gly Gly Gly Gly Ser Ser Glu Leu Thr Gln Asp Pro Ala Val Ser Val
    130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Asp Arg
            180                 185                 190

Phe Ser Gly Ser Ser Ser Gly Asn Thr Ala Ser Leu Thr Ile Thr Gly
            195                 200                 205

Ala Gln Ala Glu Asp Glu Ala Asp Tyr Tyr Cys Asn Ser Arg Asp Ser
    210                 215                 220

Ser Gly Asn His Val Val Phe Gly Gly Gly Thr Lys Leu Thr Val Leu
225                 230                 235                 240

Pro Ser Gly Gln Ala Gly Ala Ala Ala Ser Glu Ser Leu Phe Val Ser
            245                 250                 255

Asn His Ala Tyr Asn Trp Val Asn Val Ile Ser Asp Leu Lys Lys Ile
            260                 265                 270

Glu Asp Leu Ile Gln Ser Met His Ile Asp Ala Thr Leu Tyr Thr Glu
            275                 280                 285

Ser Asp Val His Pro Ser Cys Lys Val Thr Ala Met Lys Cys Phe Leu
    290                 295                 300

Leu Glu Leu Gln Val Ile Ser Leu Glu Ser Gly Asp Ala Ser Ile His
305                 310                 315                 320

Asp Thr Val Glu Asn Leu Ile Ile Leu Ala Asn Asp Ser Leu Ser Ser
                325                 330                 335

Asn Gly Asn Val Thr Glu Ser Gly Cys Lys Glu Cys Glu Glu Leu Glu
            340                 345                 350

Glu Lys Asn Ile Lys Glu Phe Leu Gln Ser Phe Val His Ile Val Gln
            355                 360                 365
```

-continued

```
Met Phe Ile Asn Thr Ser Glu Ala Ser Gly Gly Pro Glu Asp Ile Gln
    370             375             380

Met Thr Gln Ser Pro Ser Ser Leu Ser Ala Ser Val Gly Asp Arg Val
385             390             395             400

Thr Ile Thr Cys Arg Ser Thr Lys Ser Leu Leu His Ser Asn Gly Ile
            405             410             415

Thr Tyr Leu Tyr Trp Tyr Gln Gln Lys Pro Gly Lys Ala Pro Lys Leu
        420             425             430

Leu Ile Tyr Gln Met Ser Asn Leu Ala Ser Gly Val Pro Ser Arg Phe
        435             440             445

Ser Ser Ser Gly Ser Gly Thr Asp Phe Thr Leu Thr Ile Ser Ser Leu
    450             455             460

Gln Pro Glu Asp Phe Ala Thr Tyr Tyr Cys Ala Gln Asn Leu Glu Ile
465             470             475             480

Pro Arg Thr Phe Gly Gln Gly Thr Lys Val Glu Leu Lys Arg Ala Thr
                485             490             495

Pro Ser His Asn Ser His Gln Val Pro Ser Ala Gly Gly Pro Thr Ala
            500             505             510

Asn Ser Gly Thr Ser Gly Glu Val Gln Leu Val Gln Ser Gly Pro Gly
        515             520             525

Leu Val Gln Pro Gly Gly Ser Val Arg Ile Ser Cys Ala Ala Ser Gly
    530             535             540

Tyr Thr Phe Thr Asn Tyr Gly Met Asn Trp Val Lys Gln Ala Pro Gly
545             550             555             560

Lys Gly Leu Glu Trp Met Gly Trp Ile Asn Thr Tyr Thr Gly Glu Ser
            565             570             575

Thr Tyr Ala Asp Ser Phe Lys Gly Arg Phe Thr Phe Ser Leu Asp Thr
            580             585             590

Ser Ala Ser Ala Ala Tyr Leu Gln Ile Asn Ser Leu Arg Ala Glu Asp
        595             600             605

Thr Ala Val Tyr Tyr Cys Ala Arg Phe Ala Ile Lys Gly Asp Tyr Trp
    610             615             620

Gly Gln Gly Thr Leu Leu Thr Val Ser Ser
625             630
```

<210> SEQ ID NO 9
<211> LENGTH: 901
<212> TYPE: PRT
<213> ORGANISM: Artificial
<220> FEATURE:
<223> OTHER INFORMATION: Polypeptide

<400> SEQUENCE: 9

```
Met Glu Val Gln Leu Val Glu Ser Gly Gly Gly Val Val Arg Pro Gly
1               5               10              15

Gly Ser Leu Arg Leu Ser Cys Ala Ala Ser Gly Phe Thr Phe Asp Asp
            20              25              30

Tyr Gly Met Ser Trp Val Arg Gln Ala Pro Gly Lys Gly Leu Glu Trp
        35              40              45

Val Ser Gly Ile Asn Trp Asn Gly Gly Ser Thr Gly Tyr Ala Asp Ser
    50              55              60

Val Lys Gly Arg Phe Thr Ile Ser Arg Asp Asn Ala Lys Asn Ser Leu
65              70              75              80

Tyr Leu Gln Met Asn Ser Leu Arg Ala Glu Asp Thr Ala Val Tyr Tyr
            85              90              95
```

```
Cys Ala Arg Gly Arg Ser Leu Leu Phe Asp Tyr Trp Gly Gln Gly Thr
            100                 105                 110

Leu Val Thr Val Ser Arg Gly Gly Gly Ser Gly Gly Gly Gly Ser
            115                 120                 125

Gly Gly Gly Gly Ser Ser Glu Leu Thr Gln Asp Pro Ala Val Ser Val
            130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Asp Arg
                180                 185                 190

Phe Ser Gly Ser Ser Ser Gly Asn Thr Ala Ser Leu Thr Ile Thr Gly
                195                 200                 205

Ala Gln Ala Glu Asp Glu Ala Asp Tyr Tyr Cys Asn Ser Arg Asp Ser
            210                 215                 220

Ser Gly Asn His Val Val Phe Gly Gly Gly Thr Lys Leu Thr Val Leu
225                 230                 235                 240

Pro Ser Gly Gln Ala Gly Ala Ala Ala Ser Glu Ser Leu Phe Val Ser
                245                 250                 255

Asn His Ala Tyr Asn Trp Val Asn Val Ile Ser Asp Leu Lys Lys Ile
                260                 265                 270

Glu Asp Leu Ile Gln Ser Met His Ile Asp Ala Thr Leu Tyr Thr Glu
                275                 280                 285

Ser Asp Val His Pro Ser Cys Lys Val Thr Ala Met Lys Cys Phe Leu
            290                 295                 300

Leu Glu Leu Gln Val Ile Ser Leu Glu Ser Gly Asp Ala Ser Ile His
305                 310                 315                 320

Asp Thr Val Glu Asn Leu Ile Ile Leu Ala Asn Asp Ser Leu Ser Ser
                325                 330                 335

Asn Gly Asn Val Thr Glu Ser Gly Cys Lys Glu Cys Glu Glu Leu Glu
                340                 345                 350

Glu Lys Asn Ile Lys Glu Phe Leu Gln Ser Phe Val His Ile Val Gln
                355                 360                 365

Met Phe Ile Asn Thr Ser Glu Ala Ser Gly Gly Pro Glu Asp Ile Gln
    370                 375                 380

Met Thr Gln Ser Pro Ser Ser Leu Ser Ala Ser Val Gly Asp Arg Val
385                 390                 395                 400

Thr Ile Thr Cys Arg Ser Thr Lys Ser Leu Leu His Ser Asn Gly Ile
                405                 410                 415

Thr Tyr Leu Tyr Trp Tyr Gln Gln Lys Pro Gly Lys Ala Pro Lys Leu
                420                 425                 430

Leu Ile Tyr Gln Met Ser Asn Leu Ala Ser Gly Val Pro Ser Arg Phe
                435                 440                 445

Ser Ser Ser Gly Ser Gly Thr Asp Phe Thr Leu Thr Ile Ser Ser Leu
            450                 455                 460

Gln Pro Glu Asp Phe Ala Thr Tyr Tyr Cys Ala Gln Asn Leu Glu Ile
465                 470                 475                 480

Pro Arg Thr Phe Gly Gln Gly Thr Lys Val Glu Leu Lys Arg Ala Thr
                485                 490                 495

Pro Ser His Asn Ser His Gln Val Pro Ser Ala Gly Gly Pro Thr Ala
            500                 505                 510
```

```
Asn Ser Gly Thr Ser Gly Glu Val Gln Leu Val Gln Ser Gly Pro Gly
        515                 520                 525

Leu Val Gln Pro Gly Gly Ser Val Arg Ile Ser Cys Ala Ala Ser Gly
        530                 535                 540

Tyr Thr Phe Thr Asn Tyr Gly Met Asn Trp Val Lys Gln Ala Pro Gly
545                 550                 555                 560

Lys Gly Leu Glu Trp Met Gly Trp Ile Asn Thr Tyr Thr Gly Glu Ser
                565                 570                 575

Thr Tyr Ala Asp Ser Phe Lys Gly Arg Phe Thr Phe Ser Leu Asp Thr
                580                 585                 590

Ser Ala Ser Ala Ala Tyr Leu Gln Ile Asn Ser Leu Arg Ala Glu Asp
                595                 600                 605

Thr Ala Val Tyr Tyr Cys Ala Arg Phe Ala Ile Lys Gly Asp Tyr Trp
        610                 615                 620

Gly Gln Gly Thr Leu Leu Thr Val Ser Ser Glu Pro Lys Ser Ser Asp
625                 630                 635                 640

Lys Thr His Thr Ser Pro Pro Ser Pro Asp Ile Val Leu Ser Gln Ser
                645                 650                 655

Pro Ala Ile Met Ser Ala Ser Pro Gly Glu Lys Val Thr Ile Ser Cys
                660                 665                 670

Ser Ala Ser Ser Ser Val Ser Tyr Met Tyr Trp Tyr Gln Gln Lys Pro
        675                 680                 685

Gly Ser Ser Pro Lys Pro Trp Ile Tyr Arg Thr Ser Asn Leu Ala Ser
        690                 695                 700

Gly Val Pro Ala Arg Phe Ser Gly Ser Gly Ser Gly Thr Ser Tyr Ser
705                 710                 715                 720

Leu Thr Ile Ser Ser Met Glu Ala Glu Asp Ala Ala Thr Tyr Tyr Cys
                725                 730                 735

Gln Gln Tyr His Ser Tyr Pro Pro Thr Phe Gly Ala Gly Thr Lys Leu
                740                 745                 750

Glu Leu Lys Ser Ser Gly Gly Gly Gly Ser Gly Gly Gly Gly Gly Gly
                755                 760                 765

Ser Ser Arg Ser Ser Leu Glu Val Lys Leu Val Glu Ser Gly Pro Glu
        770                 775                 780

Leu Lys Lys Pro Gly Glu Thr Val Lys Ile Ser Cys Lys Ala Ser Gly
785                 790                 795                 800

Tyr Thr Phe Thr Asp Tyr Ser Met His Trp Val Asn Gln Ala Pro Gly
                805                 810                 815

Lys Gly Leu Lys Trp Met Gly Trp Ile Asn Thr Glu Thr Gly Glu Pro
                820                 825                 830

Ser Tyr Ala Asp Asp Phe Lys Gly Arg Phe Ala Phe Ser Leu Glu Thr
                835                 840                 845

Ser Ala Ser Thr Ala Tyr Leu Gln Ile Asn Asn Leu Lys Asn Glu Asp
        850                 855                 860

Thr Ala Thr Tyr Phe Cys Ala Thr Asp Tyr Gly Asp Tyr Phe Asp Tyr
865                 870                 875                 880

Trp Gly Gln Gly Thr Thr Leu Thr Val Ser Ser Ala Lys Thr Thr Pro
                885                 890                 895

Pro Ser Val Thr Ser
                900
```

<210> SEQ ID NO 10
<211> LENGTH: 623
<212> TYPE: PRT

<213> ORGANISM: Artificial
<220> FEATURE:
<223> OTHER INFORMATION: Polypeptide

<400> SEQUENCE: 10

Met Glu Val Gln Leu Val Glu Ser Gly Gly Gly Val Val Arg Pro Gly
1               5                   10                  15

Gly Ser Leu Arg Leu Ser Cys Ala Ala Ser Gly Phe Thr Phe Asp Asp
                20                  25                  30

Tyr Gly Met Ser Trp Val Arg Gln Ala Pro Gly Lys Gly Leu Glu Trp
            35                  40                  45

Val Ser Gly Ile Asn Trp Asn Gly Gly Ser Thr Gly Tyr Ala Asp Ser
    50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Gly Arg Ser Leu Leu Phe Asp Tyr Trp Gly Gln Gly Thr
            100                 105                 110

Leu Val Thr Val Ser Arg Gly Gly Gly Gly Ser Gly Gly Gly Gly Ser
            115                 120                 125

Gly Gly Gly Gly Ser Ser Glu Leu Thr Gln Asp Pro Ala Val Ser Val
    130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
            165                 170                 175

Leu Val Ile Tyr Gly Lys Asn Asn Arg Pro Ser Gly Ile Pro Asp Arg
            180                 185                 190

Phe Ser Gly Ser Ser Ser Gly Asn Thr Ala Ser Leu Thr Ile Thr Gly
            195                 200                 205

Ala Gln Ala Glu Asp Glu Ala Asp Tyr Tyr Cys Asn Ser Arg Asp Ser
    210                 215                 220

Ser Gly Asn His Val Val Phe Gly Gly Gly Thr Lys Leu Thr Val Leu
225                 230                 235                 240

Pro Ser Gly Gln Ala Gly Ala Ala Ala Ser Glu Ser Leu Phe Val Ser
            245                 250                 255

Asn His Ala Tyr Asn Trp Val Asn Val Ile Ser Asp Leu Lys Lys Ile
            260                 265                 270

Glu Asp Leu Ile Gln Ser Met His Ile Asp Ala Thr Leu Tyr Thr Glu
            275                 280                 285

Ser Asp Val His Pro Ser Cys Lys Val Thr Ala Met Lys Cys Phe Leu
    290                 295                 300

Leu Glu Leu Gln Val Ile Ser Leu Glu Ser Gly Asp Ala Ser Ile His
305                 310                 315                 320

Asp Thr Val Glu Asn Leu Ile Ile Leu Ala Asn Asp Ser Leu Ser Ser
            325                 330                 335

Asn Gly Asn Val Thr Glu Ser Gly Cys Lys Glu Cys Glu Glu Leu Glu
            340                 345                 350

Glu Lys Asn Ile Lys Glu Phe Leu Gln Ser Phe Val His Ile Val Gln
            355                 360                 365

Met Phe Ile Asn Thr Ser Glu Ala Ser Gly Gly Pro Glu Asp Ile Val
    370                 375                 380

Leu Ser Gln Ser Pro Ala Ile Met Ser Ala Ser Pro Gly Glu Lys Val

```
385                 390                 395                 400

Thr Ile Ser Cys Ser Ala Ser Ser Ser Val Ser Tyr Met Tyr Trp Tyr
                405                 410                 415

Gln Gln Lys Pro Gly Ser Ser Pro Lys Pro Trp Ile Tyr Arg Thr Ser
                420                 425                 430

Asn Leu Ala Ser Gly Val Pro Ala Arg Phe Ser Gly Ser Gly Ser Gly
                435                 440                 445

Thr Ser Tyr Ser Leu Thr Ile Ser Ser Met Glu Ala Glu Asp Ala Ala
                450                 455                 460

Thr Tyr Tyr Cys Gln Gln Tyr His Ser Tyr Pro Pro Thr Phe Gly Ala
465                 470                 475                 480

Gly Thr Lys Leu Glu Leu Lys Ser Ser Gly Gly Gly Ser Gly Gly
                485                 490                 495

Gly Gly Gly Gly Ser Ser Arg Ser Ser Leu Glu Val Lys Leu Val Glu
                500                 505                 510

Ser Gly Pro Glu Leu Lys Lys Pro Gly Glu Thr Val Lys Ile Ser Cys
                515                 520                 525

Lys Ala Ser Gly Tyr Thr Phe Thr Asp Tyr Ser Met His Trp Val Asn
                530                 535                 540

Gln Ala Pro Gly Lys Gly Leu Lys Trp Met Gly Trp Ile Asn Thr Glu
545                 550                 555                 560

Thr Gly Glu Pro Ser Tyr Ala Asp Asp Phe Lys Gly Arg Phe Ala Phe
                565                 570                 575

Ser Leu Glu Thr Ser Ala Ser Thr Ala Tyr Leu Gln Ile Asn Asn Leu
                580                 585                 590

Lys Asn Glu Asp Thr Ala Thr Tyr Phe Cys Ala Thr Asp Tyr Gly Asp
                595                 600                 605

Tyr Phe Asp Tyr Trp Gly Gln Gly Thr Thr Leu Thr Val Ser Ser
                610                 615                 620

<210> SEQ ID NO 11
<211> LENGTH: 621
<212> TYPE: PRT
<213> ORGANISM: Artificial
<220> FEATURE:
<223> OTHER INFORMATION: Polypeptide

<400> SEQUENCE: 11

Met Glu Val Gln Leu Val Glu Ser Gly Gly Gly Val Val Arg Pro Gly
1                   5                   10                  15

Gly Ser Leu Arg Leu Ser Cys Ala Ala Ser Gly Phe Thr Phe Asp Asp
                20                  25                  30

Tyr Gly Met Ser Trp Val Arg Gln Ala Pro Gly Lys Gly Leu Glu Trp
                35                  40                  45

Val Ser Gly Ile Asn Trp Asn Gly Gly Ser Thr Gly Tyr Ala Asp Ser
                50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Gly Arg Ser Leu Leu Phe Asp Tyr Trp Gly Gln Gly Thr
                100                 105                 110

Leu Val Thr Val Ser Arg Gly Gly Gly Ser Gly Gly Gly Gly Ser
                115                 120                 125

Gly Gly Gly Gly Ser Ser Glu Leu Thr Gln Asp Pro Ala Val Ser Val
```

-continued

```
             130                 135                 140
Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Asp Arg
                180                 185                 190

Phe Ser Gly Ser Ser Ser Gly Asn Thr Ala Ser Leu Thr Ile Thr Gly
                195                 200                 205

Ala Gln Ala Glu Asp Glu Ala Asp Tyr Tyr Cys Asn Ser Arg Asp Ser
    210                 215                 220

Ser Gly Asn His Val Val Phe Gly Gly Gly Thr Lys Leu Thr Val Leu
225                 230                 235                 240

Pro Ser Gly Gln Ala Gly Ala Ala Ala Ser Glu Ser Leu Phe Val Ser
                245                 250                 255

Asn His Ala Tyr Asn Trp Val Asn Val Ile Ser Asp Leu Lys Lys Ile
                260                 265                 270

Glu Asp Leu Ile Gln Ser Met His Ile Asp Ala Thr Leu Tyr Thr Glu
                275                 280                 285

Ser Asp Val His Pro Ser Cys Lys Val Thr Ala Met Lys Cys Phe Leu
    290                 295                 300

Leu Glu Leu Gln Val Ile Ser Leu Glu Ser Gly Asp Ala Ser Ile His
305                 310                 315                 320

Asp Thr Val Glu Asn Leu Ile Ile Leu Ala Asn Asp Ser Leu Ser Ser
                325                 330                 335

Asn Gly Asn Val Thr Glu Ser Gly Cys Lys Glu Cys Glu Glu Leu Glu
                340                 345                 350

Glu Lys Asn Ile Lys Glu Phe Leu Gln Ser Phe Val His Ile Val Gln
                355                 360                 365

Met Phe Ile Asn Thr Ser Glu Ala Ser Gly Gly Pro Glu Gln Val Gln
    370                 375                 380

Leu Val Gln Ser Gly Ala Glu Val Lys Lys Pro Gly Ala Ser Val Lys
385                 390                 395                 400

Val Ser Cys Lys Ala Ser Gly Tyr Ser Phe Thr Gly Tyr Thr Met Asn
                405                 410                 415

Trp Val Arg Gln Ala Pro Gly Gln Gly Leu Glu Trp Met Gly Leu Ile
                420                 425                 430

Thr Pro Tyr Asn Gly Ala Ser Ser Tyr Asn Gln Lys Phe Arg Gly Lys
                435                 440                 445

Ala Thr Met Thr Val Asp Thr Ser Thr Ser Thr Val Tyr Met Glu Leu
    450                 455                 460

Ser Ser Leu Arg Ser Glu Asp Thr Ala Val Tyr Tyr Cys Ala Arg Gly
465                 470                 475                 480

Gly Tyr Asp Gly Arg Gly Phe Asp Tyr Trp Gly Gln Gly Thr Leu Val
                485                 490                 495

Thr Val Ser Ser Gly Gly Gly Gly Ser Gly Gly Gly Gly Ser Ser Gly
                500                 505                 510

Gly Gly Ser Asp Ile Gln Met Thr Gln Ser Pro Ser Ser Leu Ser Ala
                515                 520                 525

Ser Val Gly Asp Arg Val Thr Ile Thr Cys Ser Ala Ser Ser Ser Val
    530                 535                 540

Ser Tyr Met His Trp Tyr Gln Gln Lys Ser Gly Lys Ala Pro Lys Leu
545                 550                 555                 560
```

-continued

```
Leu Ile Tyr Asp Thr Ser Lys Leu Ala Ser Gly Val Pro Ser Arg Phe
            565                 570                 575

Ser Gly Ser Gly Ser Gly Thr Asp Phe Thr Leu Thr Ile Ser Ser Leu
            580                 585                 590

Gln Pro Glu Asp Phe Ala Thr Tyr Tyr Cys Gln Gln Trp Ser Lys His
        595                 600                 605

Pro Leu Thr Phe Gly Gln Gly Thr Lys Leu Glu Ile Lys
    610                 615                 620

<210> SEQ ID NO 12
<211> LENGTH: 1040
<212> TYPE: PRT
<213> ORGANISM: Artificial
<220> FEATURE:
<223> OTHER INFORMATION: Polypeptide

<400> SEQUENCE: 12

Met Glu Val Gln Leu Val Glu Ser Gly Gly Gly Val Val Arg Pro Gly
1               5                   10                  15

Gly Ser Leu Arg Leu Ser Cys Ala Ala Ser Gly Phe Thr Phe Asp Asp
            20                  25                  30

Tyr Gly Met Ser Trp Val Arg Gln Ala Pro Gly Lys Gly Leu Glu Trp
        35                  40                  45

Val Ser Gly Ile Asn Trp Asn Gly Gly Ser Thr Gly Tyr Ala Asp Ser
    50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
            85                  90                  95

Cys Ala Arg Gly Arg Ser Leu Leu Phe Asp Tyr Trp Gly Gln Gly Thr
        100                 105                 110

Leu Val Thr Val Ser Arg Gly Gly Gly Gly Ser Gly Gly Gly Gly Ser
        115                 120                 125

Gly Gly Gly Gly Ser Ser Glu Leu Thr Gln Asp Pro Ala Val Ser Val
        130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
            165                 170                 175

Leu Val Ile Tyr Gly Lys Asn Asn Arg Pro Ser Gly Ile Pro Asp Arg
            180                 185                 190

Phe Ser Gly Ser Ser Ser Gly Asn Thr Ala Ser Leu Thr Ile Thr Gly
        195                 200                 205

Ala Gln Ala Glu Asp Glu Ala Asp Tyr Tyr Cys Asn Ser Arg Asp Ser
        210                 215                 220

Ser Gly Asn His Val Val Phe Gly Gly Gly Thr Lys Leu Thr Val Leu
225                 230                 235                 240

Glu Pro Lys Ser Ser Asp Lys Thr His Thr Ser Pro Pro Ser Pro Asn
            245                 250                 255

Trp Val Asn Val Ile Ser Asp Leu Lys Lys Ile Glu Asp Leu Ile Gln
            260                 265                 270

Ser Met His Ile Asp Ala Thr Leu Tyr Thr Glu Ser Asp Val His Pro
        275                 280                 285

Ser Cys Lys Val Thr Ala Met Lys Cys Phe Leu Leu Glu Leu Gln Val
        290                 295                 300
```

-continued

```
Ile Ser Leu Glu Ser Gly Asp Ala Ser Ile His Asp Thr Val Glu Asn
305             310             315             320

Leu Ile Ile Leu Ala Asn Asp Ser Leu Ser Ser Asn Gly Asn Val Thr
                325             330             335

Glu Ser Gly Cys Lys Glu Cys Glu Glu Leu Glu Glu Lys Asn Ile Lys
            340             345             350

Glu Phe Leu Gln Ser Phe Val His Ile Val Gln Met Phe Ile Asn Thr
            355             360             365

Ser Pro Ser Gly Gln Ala Gly Ala Ala Ala Ser Glu Ser Leu Phe Val
    370             375             380

Ser Asn His Ala Tyr Asp Ile Gln Met Thr Gln Ser Pro Ser Ser Leu
385             390             395             400

Ser Ala Ser Val Gly Asp Arg Val Thr Ile Thr Cys Arg Ser Thr Lys
            405             410             415

Ser Leu Leu His Ser Asn Gly Ile Thr Tyr Leu Tyr Trp Tyr Gln Gln
            420             425             430

Lys Pro Gly Lys Ala Pro Lys Leu Leu Ile Tyr Gln Met Ser Asn Leu
            435             440             445

Ala Ser Gly Val Pro Ser Arg Phe Ser Ser Ser Gly Ser Gly Thr Asp
    450             455             460

Phe Thr Leu Thr Ile Ser Ser Leu Gln Pro Glu Asp Phe Ala Thr Tyr
465             470             475             480

Tyr Cys Ala Gln Asn Leu Glu Ile Pro Arg Thr Phe Gly Gln Gly Thr
            485             490             495

Lys Val Glu Leu Lys Arg Ala Thr Pro Ser His Asn Ser His Gln Val
            500             505             510

Pro Ser Ala Gly Gly Pro Thr Ala Asn Ser Gly Thr Ser Gly Glu Ala
            515             520             525

Ser Gly Gly Pro Glu Asp Ile Gln Met Thr Gln Thr Thr Ser Ser Leu
    530             535             540

Ser Ala Ser Leu Gly Asp Arg Val Thr Ile Ser Cys Arg Ala Ser Gln
545             550             555             560

Asp Ile Ser Asn Tyr Leu Asn Trp Tyr Gln Gln Lys Pro Asp Gly Thr
                565             570             575

Val Lys Leu Leu Ile Tyr Tyr Thr Ser Ile Leu His Ser Gly Val Pro
            580             585             590

Ser Arg Phe Ser Gly Ser Gly Ser Gly Thr Asp Tyr Ser Leu Thr Ile
            595             600             605

Ser Asn Leu Glu Gln Glu Asp Phe Ala Thr Tyr Phe Cys Gln Gln Gly
            610             615             620

Asn Thr Leu Pro Trp Thr Phe Gly Gly Gly Thr Lys Leu Glu Ile Lys
625             630             635             640

Gly Ser Thr Ser Gly Ser Gly Lys Pro Gly Ser Gly Glu Gly Ser Thr
            645             650             655

Lys Gly Glu Val Gln Leu Val Glu Ser Gly Gly Gly Leu Val Lys Pro
            660             665             670

Gly Gly Ser Leu Lys Leu Ser Cys Ala Ala Ser Gly Phe Ala Phe Ser
            675             680             685

Ile Tyr Asp Met Ser Trp Val Arg Gln Thr Pro Glu Lys Arg Leu Glu
            690             695             700

Trp Val Ala Tyr Ile Ser Ser Gly Gly Gly Thr Thr Tyr Tyr Pro Asp
705             710             715             720
```

```
Thr Val Lys Gly Arg Phe Thr Ile Ser Arg Asp Asn Ala Lys Asn Thr
              725                 730                 735

Leu Tyr Leu Gln Met Ser Ser Leu Lys Ser Glu Asp Thr Ala Met Tyr
              740                 745                 750

Tyr Cys Ala Arg His Ser Gly Tyr Gly Thr His Trp Gly Val Leu Phe
              755                 760                 765

Ala Tyr Trp Gly Gln Gly Thr Leu Val Thr Val Ser Ala Gly Gly Gly
              770                 775                 780

Gly Ser Asp Ile Leu Leu Thr Gln Thr Pro Ala Ser Leu Ala Val Ser
785                 790                 795                 800

Leu Gly Gln Arg Ala Thr Ile Ser Cys Lys Ala Ser Gln Ser Val Asp
                  805                 810                 815

Tyr Asp Gly Asp Ser Tyr Leu Asn Trp Tyr Gln Gln Ile Pro Gly Gln
                  820                 825                 830

Pro Pro Lys Leu Leu Ile Tyr Asp Ala Ser Asn Leu Val Ser Gly Ile
                  835                 840                 845

Pro Pro Arg Phe Ser Gly Ser Gly Ser Gly Thr Asp Phe Thr Leu Asn
                  850                 855                 860

Ile His Pro Val Glu Lys Val Asp Ala Ala Thr Tyr His Cys Gln Gln
865                 870                 875                 880

Ser Thr Glu Asp Pro Trp Thr Phe Gly Gly Gly Thr Lys Leu Glu Ile
                  885                 890                 895

Lys Arg Gly Ser Thr Ser Gly Ser Gly Lys Pro Gly Ser Gly Glu Gly
                  900                 905                 910

Ser Thr Lys Gly Gln Val Gln Leu Gln Gln Ser Gly Ala Glu Leu Val
                  915                 920                 925

Arg Pro Gly Ser Ser Val Lys Ile Ser Cys Lys Ala Ser Gly Tyr Ala
              930                 935                 940

Phe Ser Ser Tyr Trp Met Asn Trp Val Lys Gln Arg Pro Gly Gln Gly
945                 950                 955                 960

Leu Glu Trp Ile Gly Gln Ile Trp Pro Gly Asp Gly Asp Thr Asn Tyr
                  965                 970                 975

Asn Gly Lys Phe Lys Gly Lys Ala Thr Leu Thr Ala Asp Glu Ser Ser
                  980                 985                 990

Ser Thr Ala Tyr Met Gln Leu Ser  Ser Leu Ala Ser Glu  Asp Ser Ala
                  995                 1000                1005

Val Tyr  Phe Cys Ala Arg Arg  Glu Thr Thr Thr Val  Gly Arg Tyr
    1010                1015                1020

Tyr Tyr  Ala Met Asp Tyr Trp  Gly Gln Gly Thr Ser  Val Thr Val
    1025                1030                1035

Ser Ser
    1040
```

<210> SEQ ID NO 13
<211> LENGTH: 661
<212> TYPE: PRT
<213> ORGANISM: Artificial
<220> FEATURE:
<223> OTHER INFORMATION: Polypeptide

<400> SEQUENCE: 13

```
Met Asp Ile Gln Met Thr Gln Ser Pro Ser Ser Leu Ser Ala Ser Val
1                 5                   10                  15

Gly Asp Arg Val Thr Ile Thr Cys Arg Ala Ser Gln Asp Ile Arg Asn
              20                  25                  30
```

-continued

```
Tyr Leu Asn Trp Tyr Gln Gln Lys Pro Asp Gly Thr Val Lys Leu Leu
    35                  40                  45

Ile Tyr Tyr Thr Ser Arg Leu His Ser Gly Val Pro Ser Lys Phe Ser
    50                  55                  60

Gly Ser Gly Ser Gly Thr Asp Tyr Thr Leu Thr Ile Ser Asn Leu Glu
65                  70                  75                  80

Gln Glu Asp Ile Ala Thr Tyr Phe Cys Gln Gln Gly Asn Thr Leu Pro
                85                  90                  95

Trp Thr Phe Ala Gly Gly Thr Lys Leu Glu Ile Lys Arg Gly Gly Gly
                100                 105                 110

Gly Ser Gly Gly Gly Gly Ser Gly Gly Gly Gly Ser Gly Gly Arg Glu
                115                 120                 125

Val Gln Leu Val Gln Ser Gly Ala Glu Leu Val Lys Pro Gly Ala Thr
    130                 135                 140

Met Lys Ile Ser Cys Lys Ala Ser Gly Tyr Ser Phe Thr Gly Tyr Thr
145                 150                 155                 160

Met Asn Trp Val Lys Gln Ser His Gly Lys Asn Leu Glu Trp Met Gly
                165                 170                 175

Leu Ile Asn Pro Tyr Lys Gly Val Ser Thr Tyr Asn Gln Lys Phe Lys
                180                 185                 190

Asp Lys Ala Thr Leu Thr Val Asp Thr Ser Thr Asp Thr Ala Tyr Met
                195                 200                 205

Glu Leu Leu Ser Leu Thr Ser Glu Asp Ser Ala Val Tyr Tyr Cys Ala
    210                 215                 220

Arg Ser Gly Tyr Tyr Gly Asp Ser Asp Trp Tyr Phe Asp Val Trp Gly
225                 230                 235                 240

Ala Gly Thr Thr Val Thr Val Ser Ser Pro Ser Gly Gln Ala Gly Ala
                245                 250                 255

Ala Ala Ser Glu Ser Leu Phe Val Ser Asn His Ala Tyr Pro Thr Ser
                260                 265                 270

Ser Ser Thr Lys Lys Thr Gln Leu Gln Leu Glu His Leu Leu Leu Asp
    275                 280                 285

Leu Gln Met Ile Leu Asn Gly Ile Asn Asn Tyr Lys Asn Pro Lys Leu
    290                 295                 300

Thr Arg Met Leu Thr Phe Lys Phe Tyr Met Pro Lys Lys Ala Thr Glu
305                 310                 315                 320

Leu Lys His Leu Gln Cys Leu Glu Glu Glu Leu Lys Pro Leu Glu Glu
                325                 330                 335

Val Leu Asn Leu Ala Gln Ser Lys Asn Phe His Leu Arg Pro Arg Asp
    340                 345                 350

Leu Ile Ser Asn Ile Asn Val Ile Val Leu Glu Leu Lys Gly Ser Glu
    355                 360                 365

Thr Thr Phe Met Cys Glu Tyr Ala Asp Glu Thr Ala Thr Ile Val Glu
    370                 375                 380

Phe Leu Asn Arg Trp Ile Thr Phe Cys Gln Ser Ile Ile Ser Thr Leu
385                 390                 395                 400

Thr Glu Ala Ser Gly Gly Pro Glu Asp Ile Gln Met Thr Gln Ser Pro
                405                 410                 415

Ser Ser Leu Ser Ala Ser Val Gly Asp Arg Val Thr Ile Thr Cys Arg
                420                 425                 430

Ser Thr Lys Ser Leu Leu His Ser Asn Gly Ile Thr Tyr Leu Tyr Trp
    435                 440                 445

Tyr Gln Gln Lys Pro Gly Lys Ala Pro Lys Leu Leu Ile Tyr Gln Met
```

-continued

```
              450                    455                    460

Ser Asn Leu Ala Ser Gly Val Pro Ser Arg Phe Ser Ser Ser Gly Ser
465                 470                    475                    480

Gly Thr Asp Phe Thr Leu Thr Ile Ser Ser Leu Gln Pro Glu Asp Phe
                    485                    490                    495

Ala Thr Tyr Tyr Cys Ala Gln Asn Leu Glu Ile Pro Arg Thr Phe Gly
                    500                    505                    510

Gln Gly Thr Lys Val Glu Leu Lys Arg Ala Thr Pro Ser His Asn Ser
            515                    520                    525

His Gln Val Pro Ser Ala Gly Gly Pro Thr Ala Asn Ser Gly Thr Ser
        530                    535                    540

Gly Glu Val Gln Leu Val Gln Ser Gly Pro Gly Leu Val Gln Pro Gly
545                 550                    555                    560

Gly Ser Val Arg Ile Ser Cys Ala Ala Ser Gly Tyr Thr Phe Thr Asn
                    565                    570                    575

Tyr Gly Met Asn Trp Val Lys Gln Ala Pro Gly Lys Gly Leu Glu Trp
                580                    585                    590

Met Gly Trp Ile Asn Thr Tyr Thr Gly Glu Ser Thr Tyr Ala Asp Ser
            595                    600                    605

Phe Lys Gly Arg Phe Thr Phe Ser Leu Asp Thr Ser Ala Ser Ala Ala
        610                    615                    620

Tyr Leu Gln Ile Asn Ser Leu Arg Ala Glu Asp Thr Ala Val Tyr Tyr
625                 630                    635                    640

Cys Ala Arg Phe Ala Ile Lys Gly Asp Tyr Trp Gly Gln Gly Thr Leu
                    645                    650                    655

Leu Thr Val Ser Ser
                660

<210> SEQ ID NO 14
<211> LENGTH: 539
<212> TYPE: PRT
<213> ORGANISM: Artificial
<220> FEATURE:
<223> OTHER INFORMATION: Polypeptide

<400> SEQUENCE: 14

Met Lys Trp Val Thr Phe Ile Ser Leu Leu Phe Leu Phe Ser Ser Ala
1               5                    10                    15

Tyr Ser Gln Val Gln Leu Val Glu Ser Gly Gly Gly Leu Val Gln Pro
                20                    25                    30

Gly Gly Ser Leu Arg Leu Ser Cys Ala Ala Ser Gly Leu Thr Phe Ser
            35                    40                    45

Ser Tyr Asn Met Gly Trp Phe Arg Gln Ala Pro Gly Gln Gly Leu Glu
        50                    55                    60

Ala Val Ala Ser Ile Thr Trp Ser Gly Arg Asp Thr Phe Tyr Ala Asp
65                  70                    75                    80

Ser Val Lys Gly Arg Phe Thr Ile Ser Arg Asp Asn Ser Lys Asn Thr
                85                    90                    95

Leu Tyr Leu Gln Met Asn Ser Leu Arg Ala Glu Asp Thr Ala Val Tyr
                100                    105                    110

Tyr Cys Ala Ala Asn Pro Trp Pro Val Ala Ala Pro Arg Ser Gly Thr
            115                    120                    125

Tyr Trp Gly Gln Gly Thr Leu Val Thr Val Ser Ser Ser Gly Gly Gly
        130                    135                    140

Gly Ser Gly Gly Gly Gly Ser Gly Gly Gly Gly Ser Gly Gly Gly Gly
```

-continued

```
145              150              155              160

Ser Gly Asn Trp Val Asn Val Ile Ser Asp Leu Lys Lys Ile Glu Asp
             165              170              175

Leu Ile Gln Ser Met His Ile Asp Ala Thr Leu Tyr Thr Glu Ser Asp
             180              185              190

Val His Pro Ser Cys Lys Val Thr Ala Met Lys Cys Phe Leu Leu Glu
             195              200              205

Leu Gln Val Ile Ser Leu Glu Ser Gly Asp Ala Ser Ile His Asp Thr
             210              215              220

Val Glu Asn Leu Ile Ile Leu Ala Asn Asn Ser Leu Ser Ser Asn Gly
225              230              235              240

Asn Val Thr Glu Ser Gly Cys Lys Glu Cys Glu Glu Leu Glu Glu Lys
             245              250              255

Asn Ile Lys Glu Phe Leu Gln Ser Phe Val His Ile Val Gln Met Phe
             260              265              270

Ile Asn Thr Ser Gly Ser Thr Ser Gly Ser Gly Lys Pro Gly Ser Gly
             275              280              285

Glu Gly Ser Thr Lys Gly Gln Val Gln Leu Val Gln Ser Gly Ala Glu
             290              295              300

Val Lys Lys Pro Gly Ser Ser Val Lys Val Ser Cys Lys Ala Ser Gly
305              310              315              320

Tyr Thr Phe Thr Asp Tyr Asn Met His Trp Val Arg Gln Ala Pro Gly
             325              330              335

Gln Gly Leu Glu Trp Ile Gly Tyr Ile Tyr Pro Tyr Asn Gly Gly Thr
             340              345              350

Gly Tyr Asn Gln Lys Phe Lys Ser Lys Ala Thr Ile Thr Ala Asp Glu
             355              360              365

Ser Thr Asn Thr Ala Tyr Met Glu Leu Ser Ser Leu Arg Ser Glu Asp
             370              375              380

Thr Ala Val Tyr Tyr Cys Ala Arg Gly Arg Pro Ala Met Asp Tyr Trp
385              390              395              400

Gly Gln Gly Thr Leu Val Thr Val Ser Ser Gly Gly Gly Ser Gly
             405              410              415

Gly Gly Gly Ser Gly Gly Gly Ser Asp Ile Gln Met Thr Gln Ser
             420              425              430

Pro Ser Ser Leu Ser Ala Ser Val Gly Asp Arg Val Thr Ile Thr Cys
             435              440              445

Arg Ala Ser Glu Ser Val Asp Asn Tyr Gly Ile Ser Phe Met Asn Trp
             450              455              460

Phe Gln Gln Lys Pro Gly Lys Ala Pro Lys Leu Leu Ile Tyr Ala Ala
465              470              475              480

Ser Asn Gln Gly Ser Gly Val Pro Ser Arg Phe Ser Gly Ser Gly Ser
             485              490              495

Gly Thr Asp Phe Thr Leu Thr Ile Ser Ser Leu Gln Pro Asp Asp Phe
             500              505              510

Ala Thr Tyr Tyr Cys Gln Gln Ser Lys Glu Val Pro Trp Thr Phe Gly
             515              520              525

Gln Gly Thr Lys Val Glu Ile Lys Val Asp Glu
             530              535
```

<210> SEQ ID NO 15
<211> LENGTH: 114
<212> TYPE: PRT
<213> ORGANISM: Artificial

-continued

```
<220> FEATURE:
<223> OTHER INFORMATION: Polypeptide

<400> SEQUENCE: 15

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 16
<211> LENGTH: 623
<212> TYPE: PRT
<213> ORGANISM: Artificial
<220> FEATURE:
<223> OTHER INFORMATION: Polypeptide

<400> SEQUENCE: 16

Met Glu Val Gln Leu Val Glu Ser Gly Gly Gly Val Val Arg Pro Gly
1               5                   10                  15

Gly Ser Leu Arg Leu Ser Cys Ala Ala Ser Gly Phe Thr Phe Asp Asp
            20                  25                  30

Tyr Gly Met Ser Trp Val Arg Gln Ala Pro Gly Lys Gly Leu Glu Trp
        35                  40                  45

Val Ser Gly Ile Asn Trp Asn Gly Gly Ser Thr Gly Tyr Ala Asp Ser
    50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Gly Arg Ser Leu Leu Phe Asp Tyr Trp Gly Gln Gly Thr
            100                 105                 110

Leu Val Thr Val Ser Arg Gly Gly Gly Gly Ser Gly Gly Gly Gly Ser
        115                 120                 125

Gly Gly Gly Gly Ser Ser Glu Leu Thr Gln Asp Pro Ala Val Ser Val
    130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Asp Arg
            180                 185                 190

Phe Ser Gly Ser Ser Ser Gly Asn Thr Ala Ser Leu Thr Ile Thr Gly
        195                 200                 205

Ala Gln Ala Glu Asp Glu Ala Asp Tyr Tyr Cys Asn Ser Arg Asp Ser
    210                 215                 220
```

```
Ser Gly Asn His Val Val Phe Gly Gly Gly Thr Lys Leu Thr Val Leu
225             230             235             240

Pro Ser Gly Gln Ala Gly Ala Ala Ala Ser Glu Ser Leu Phe Val Ser
            245             250             255

Asn His Ala Tyr Asn Trp Val Asn Val Ile Ser Asp Leu Lys Lys Ile
            260             265             270

Glu Asp Leu Ile Gln Ser Met His Ile Asp Ala Thr Leu Tyr Thr Glu
            275             280             285

Ser Asp Val His Pro Ser Cys Lys Val Thr Ala Met Lys Cys Phe Leu
            290             295             300

Leu Glu Leu Gln Val Ile Ser Leu Glu Ser Gly Asp Ala Ser Ile His
305             310             315             320

Asp Thr Val Glu Asn Leu Ile Ile Leu Ala Asn Asp Ser Leu Ser Ser
            325             330             335

Asn Gly Asn Val Thr Glu Ser Gly Cys Lys Glu Cys Glu Glu Leu Glu
            340             345             350

Glu Lys Asn Ile Lys Glu Phe Leu Gln Ser Phe Val His Ile Val Gln
            355             360             365

Met Phe Ile Asn Thr Ser Glu Ala Ser Gly Gly Pro Glu Ala Lys Val
            370             375             380

Gln Leu Gln Glu Ser Gly Pro Ser Leu Val Gln Pro Ser Gln Arg Leu
385             390             395             400

Ser Ile Thr Cys Thr Val Ser Gly Phe Ser Leu Ile Ser Tyr Gly Val
            405             410             415

His Trp Val Arg Gln Ser Pro Gly Lys Gly Leu Glu Trp Leu Gly Val
            420             425             430

Ile Trp Arg Gly Gly Ser Thr Asp Tyr Asn Ala Ala Phe Met Ser Arg
            435             440             445

Leu Ser Ile Thr Lys Asp Asn Ser Lys Ser Gln Val Phe Phe Lys Met
            450             455             460

Asn Ser Leu Gln Ala Asp Asp Thr Ala Ile Tyr Phe Cys Ala Lys Thr
465             470             475             480

Leu Ile Thr Thr Gly Tyr Ala Met Asp Tyr Trp Gly Gln Gly Thr Thr
            485             490             495

Val Thr Val Ser Ser Gly Gly Gly Gly Ser Gly Gly Gly Gly Ser Gly
            500             505             510

Gly Gly Gly Ser Asp Ile Glu Leu Thr Gln Ser Pro Ser Ser Phe Ser
            515             520             525

Val Ser Leu Gly Asp Arg Val Thr Ile Thr Cys Lys Ala Ser Glu Asp
            530             535             540

Ile Tyr Asn Arg Leu Ala Trp Tyr Gln Gln Lys Pro Gly Asn Ala Pro
545             550             555             560

Arg Leu Leu Ile Ser Gly Ala Thr Ser Leu Glu Thr Gly Val Pro Ser
            565             570             575

Arg Phe Ser Gly Ser Gly Ser Gly Lys Asp Tyr Thr Leu Ser Ile Thr
            580             585             590

Ser Leu Gln Thr Glu Asp Val Ala Thr Tyr Tyr Cys Gln Gln Tyr Trp
            595             600             605

Ser Thr Pro Thr Phe Gly Gly Gly Thr Lys Leu Glu Ile Lys Arg
            610             615             620
```

<210> SEQ ID NO 17
<211> LENGTH: 243

-continued

<212> TYPE: PRT
<213> ORGANISM: Artificial
<220> FEATURE:
<223> OTHER INFORMATION: Polypeptide
<400> SEQUENCE: 17

```
Met Asp Ile Val Leu Ser Gln Ser Pro Ala Ile Met Ser Ala Ser Pro
1               5                   10                  15

Gly Glu Lys Val Thr Ile Ser Cys Ser Ala Ser Ser Ser Val Ser Tyr
                20                  25                  30

Met Tyr Trp Tyr Gln Gln Lys Pro Gly Ser Ser Pro Lys Pro Trp Ile
            35                  40                  45

Tyr Arg Thr Ser Asn Leu Ala Ser Gly Val Pro Ala Arg Phe Ser Gly
        50                  55                  60

Ser Gly Ser Gly Thr Ser Tyr Ser Leu Thr Ile Ser Ser Met Glu Ala
65                  70                  75                  80

Glu Asp Ala Ala Thr Tyr Tyr Cys Gln Gln Tyr His Ser Tyr Pro Pro
                85                  90                  95

Thr Phe Gly Ala Gly Thr Lys Leu Glu Leu Lys Ser Ser Gly Gly Gly
            100                 105                 110

Gly Ser Gly Gly Gly Gly Gly Gly Ser Ser Arg Ser Ser Leu Glu Val
        115                 120                 125

Lys Leu Val Glu Ser Gly Pro Glu Leu Lys Lys Pro Gly Glu Thr Val
    130                 135                 140

Lys Ile Ser Cys Lys Ala Ser Gly Tyr Thr Phe Thr Asp Tyr Ser Met
145                 150                 155                 160

His Trp Val Asn Gln Ala Pro Gly Lys Gly Leu Lys Trp Met Gly Trp
                165                 170                 175

Ile Asn Thr Glu Thr Gly Glu Pro Ser Tyr Ala Asp Asp Phe Lys Gly
            180                 185                 190

Arg Phe Ala Phe Ser Leu Glu Thr Ser Ala Ser Thr Ala Tyr Leu Gln
        195                 200                 205

Ile Asn Asn Leu Lys Asn Glu Asp Thr Ala Thr Tyr Phe Cys Ala Thr
    210                 215                 220

Asp Tyr Gly Asp Tyr Phe Asp Tyr Trp Gly Gln Gly Thr Thr Leu Thr
225                 230                 235                 240

Val Ser Ser
```

<210> SEQ ID NO 18
<211> LENGTH: 132
<212> TYPE: PRT
<213> ORGANISM: Artificial
<220> FEATURE:
<223> OTHER INFORMATION: Polypeptide
<400> SEQUENCE: 18

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Arg
65                  70                  75                  80
```

-continued

```
Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Gln Ser Ile Ile
        115                 120                 125

Ser Thr Leu Thr
    130

<210> SEQ ID NO 19
<211> LENGTH: 630
<212> TYPE: PRT
<213> ORGANISM: Artificial
<220> FEATURE:
<223> OTHER INFORMATION: Polypeptide

<400> SEQUENCE: 19

Met Glu Val Gln Leu Val Glu Ser Gly Gly Gly Val Val Arg Pro Gly
1               5                   10                  15

Gly Ser Leu Arg Leu Ser Cys Ala Ala Ser Gly Phe Thr Phe Asp Asp
            20                  25                  30

Tyr Gly Met Ser Trp Val Arg Gln Ala Pro Gly Lys Gly Leu Glu Trp
        35                  40                  45

Val Ser Gly Ile Asn Trp Asn Gly Gly Ser Thr Gly Tyr Ala Asp Ser
    50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Gly Arg Ser Leu Leu Phe Asp Tyr Trp Gly Gln Gly Thr
            100                 105                 110

Leu Val Thr Val Ser Arg Gly Gly Gly Gly Ser Gly Gly Gly Gly Ser
        115                 120                 125

Gly Gly Gly Gly Ser Ser Glu Leu Thr Gln Asp Pro Ala Val Ser Val
    130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Asp Arg
            180                 185                 190

Phe Ser Gly Ser Ser Ser Gly Asn Thr Ala Ser Leu Thr Ile Thr Gly
        195                 200                 205

Ala Gln Ala Glu Asp Glu Ala Asp Tyr Tyr Cys Asn Ser Arg Asp Ser
    210                 215                 220

Ser Gly Asn His Val Val Phe Gly Gly Gly Thr Lys Leu Thr Val Leu
225                 230                 235                 240

Pro Ser Gly Gln Ala Gly Ala Ala Ala Ser Glu Ser Leu Phe Val Ser
                245                 250                 255

Asn His Ala Tyr Asn Trp Val Asn Val Ile Ser Asp Leu Lys Lys Ile
            260                 265                 270

Glu Asp Leu Ile Gln Ser Met His Ile Asp Ala Thr Leu Tyr Thr Glu
        275                 280                 285

Ser Asp Val His Pro Ser Cys Lys Val Thr Ala Met Lys Cys Phe Leu
    290                 295                 300
```

```
Leu Glu Leu Gln Val Ile Ser Leu Glu Ser Gly Asp Ala Ser Ile His
305                 310                 315                 320

Asp Thr Val Glu Asn Leu Ile Ile Leu Ala Asn Asp Ser Leu Ser Ser
                325                 330                 335

Asn Gly Asn Val Thr Glu Ser Gly Cys Lys Glu Cys Glu Glu Leu Glu
                340                 345                 350

Glu Lys Asn Ile Lys Glu Phe Leu Gln Ser Phe Val His Ile Val Gln
                355                 360                 365

Met Phe Ile Asn Thr Ser Glu Ala Ser Gly Gly Pro Glu Met Gly Trp
370                 375                 380

Ser Cys Ile Ile Leu Phe Leu Val Ala Thr Ala Thr Gly Val His Ser
385                 390                 395                 400

Gln Val Arg Leu Ser Gln Ser Gly Gly Gln Met Lys Lys Pro Gly Asp
                405                 410                 415

Ser Met Arg Ile Ser Cys Arg Ala Ser Gly Tyr Glu Phe Ile Asn Cys
                420                 425                 430

Pro Ile Asn Trp Ile Arg Leu Ala Pro Gly Lys Arg Pro Glu Trp Met
                435                 440                 445

Gly Trp Met Lys Pro Arg His Gly Ala Val Ser Tyr Ala Arg Gln Leu
        450                 455                 460

Gln Gly Arg Val Thr Met Thr Arg Asp Met Tyr Ser Glu Thr Ala Phe
465                 470                 475                 480

Leu Glu Leu Arg Ser Leu Thr Ser Asp Asp Thr Ala Val Tyr Phe Cys
                485                 490                 495

Thr Arg Gly Lys Tyr Cys Thr Ala Arg Asp Tyr Tyr Asn Trp Asp Phe
                500                 505                 510

Glu His Trp Gly Gln Gly Thr Pro Val Thr Val Ser Ser Ala Ser Thr
        515                 520                 525

Lys Gly Pro Ser Val Phe Pro Leu Ala Pro Ser Ser Lys Ser Thr Ser
        530                 535                 540

Gly Gly Thr Ala Ala Leu Gly Cys Leu Val Lys Asp Tyr Phe Pro Glu
545                 550                 555                 560

Pro Val Thr Val Ser Trp Asn Ser Gly Ala Leu Thr Ser Gly Val His
                565                 570                 575

Thr Phe Pro Ala Val Leu Gln Ser Ser Gly Leu Tyr Ser Leu Ser Ser
                580                 585                 590

Val Val Thr Val Pro Ser Ser Ser Leu Gly Thr Gln Thr Tyr Ile Cys
                595                 600                 605

Asn Val Asn His Lys Pro Ser Asn Thr Lys Val Asp Lys Lys Val Glu
        610                 615                 620

Pro Lys Ser Cys Asp Lys
625                 630
```

<210> SEQ ID NO 20
<211> LENGTH: 140
<212> TYPE: PRT
<213> ORGANISM: Artificial
<220> FEATURE:
<223> OTHER INFORMATION: Polypeptide

<400> SEQUENCE: 20

```
Met Lys Trp Val Thr Phe Ile Ser Leu Leu Phe Leu Phe Ser Ser Ala
1                   5                   10                  15

Tyr Ser Gln Val Gln Leu Val Glu Ser Gly Gly Gly Leu Val Gln Pro
                20                  25                  30
```

-continued

```
Gly Gly Ser Leu Arg Leu Ser Cys Ala Ala Ser Gly Leu Thr Phe Ser
        35              40              45

Ser Tyr Asn Met Gly Trp Phe Arg Gln Ala Pro Gly Gln Gly Leu Glu
    50              55              60

Ala Val Ala Ser Ile Thr Trp Ser Gly Arg Asp Thr Phe Tyr Ala Asp
65              70              75              80

Ser Val Lys Gly Arg Phe Thr Ile Ser Arg Asp Asn Ser Lys Asn Thr
            85              90              95

Leu Tyr Leu Gln Met Asn Ser Leu Arg Ala Glu Asp Thr Ala Val Tyr
            100             105             110

Tyr Cys Ala Ala Asn Pro Trp Pro Val Ala Ala Pro Arg Ser Gly Thr
        115             120             125

Tyr Trp Gly Gln Gly Thr Leu Val Thr Val Ser Ser
    130             135             140
```

THERAPEUTIC COMPOUNDS AND METHODS

CROSS-REFERENCE TO RELATED APPLICATION

This application is a continuation of U.S. patent application Ser. No. 15/766,067, filed Apr. 5, 2018, which is the § 371 U.S. National Stage of International Application No. PCT/US2016/055722, filed Oct. 6, 2016, which claims priority to U.S. Provisional Patent Application No. 62/237,835, filed Oct. 6, 2015, each of which is incorporated herein by reference.

GOVERNMENT FUNDING

This invention was made with government support under CA036725, CA065493, CA197292, CA072669, and CA111412, awarded by the National Institutes of Health. The government has certain rights in the invention.

SEQUENCE LISTING

This application contains a Sequence Listing electronically submitted via EFS-Web to the United States Patent and Trademark Office as an ASCII text file entitled "0110-000499US04-SequeneListing_ST25.txt" having a size of 85 kilobytes and created on Jul. 28, 2021. The information contained in the Sequence Listing is incorporated by reference herein.

SUMMARY

This disclosure relates to the design, construction, and use of trispecific killer engager (TriKE) molecules.

This disclosure describes, in one aspect, a molecule engineered to possess an NK engaging domain, an NK activating domain operably linked to the NK engaging domain, and a targeting domain that selectively binds to a target cell and is operably linked to the NK activating domain and the NK engaging domain.

In some embodiments, the NK activating domain can include at least a portion of a cytokine.

In some embodiments, the NK engaging domain can include a moiety that selectively binds to an NK cell. The moiety that selectively binds to the NK cell can activate NK cells and/or block inhibition of NK cells. In some embodiments, the NK engaging domain can include an antibody or a fragment thereof.

In some embodiments, the target cell can be a tumor cell or a cell infected by a virus. In some embodiments, the targeting domain can include an antibody or a fragment thereof. In other embodiments, the targeting domain can include a ligand or small molecule that selectively binds to the target cell.

In some embodiments, the molecule may be designed to include a second targeting domain, a second NK activating domain, or a second NK engaging domain.

In another aspect, this disclosure describes a molecule engineered to include a T cell engaging domain, a T cell activating domain operably linked to the T cell engaging domain, and a targeting domain that selectively binds to a target cell and is operably linked to the T cell activating domain and the T cell engaging domain.

In some embodiments, the T cell activating domain can include at least a portion of a cytokine.

In some embodiments, the T cell engaging domain can include a moiety that selectively binds to a T cell. The moiety that selectively binds to the T cell can activate T cells and/or block inhibition of T cells. In some embodiments, the T engaging domain can include an antibody or a fragment thereof.

In some embodiments, the target cell can be a tumor cell or a cell infected by a virus. In some embodiments, the targeting domain can include an antibody or a fragment thereof. In other embodiments, the targeting domain can include a ligand or small molecule that selectively binds to the target cell.

In some embodiments, the molecule may be designed to include a second targeting domain, a second T cell activating domain, or a second T cell engaging domain.

In some embodiments of either aspect, the molecule can include a flanking sequence between any two of the domains summarized immediately above. In some cases, the molecule can have more than one flanking sequence.

In another aspect, this disclosure describes a method that involves administering any embodiment of the engineered molecule summarized above to a subject in an amount effective to induce NK-mediated killing of the target cell or T-cell-mediated killing of the target cell, as may be appropriate for the particular molecule that is administered.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 13. Schematic of the placement of the polynucleotide encoding 1615EpCAM133 (SEQ ID NO:9) domains in the pET expression vector. Synthesis and assembly of the hybrid polynucleotide encoding 1615EpCAM133 was accomplished using DNA shuffling and DNA ligation techniques. The fully assembled coding region has, from the 5' end to the 3' end, an NcoI restriction site; an ATG initiation codon; coding regions encoding the $V_H$ and $V_L$ regions of human CD16 (NM3E2) derived from a phage display library, a 20 amino acid segment (PSGQAGAAAS-ESLFVSNHAY; SEQ ID NO:3), modified IL-15, a seven amino acid segment (EASGGPE; SEQ ID NO:4), the humanized anti-EPCAM scFv from the antibody MOC-31, a 15 amino acid mutated human IgG1 hinge region, and the anti-CD133 scFv from clone 7; and finally a NotI restriction site. The resultant 2715 bp NcoI/NotI fragment polynucleotide was spliced into the pET28c expression vector under control of an isopropyl-β-D-thiogalactopyranoside (IPTG) (FischerBiotech, Fair Lawn, N.J.) inducible T7promoter. DNA sequencing analysis (Biomedical Genomics Center, University of Minnesota, Minn., USA) was used to verify that the polynucleotide was correct in sequence and had been cloned in frame.

FIG. 21. The CD3 portion of CD3−IL2−EpCAM was tested and intact. (A) and (B): the same anti-CD3 scFv was spliced to diphtheria toxin and incubated with CD3+ HPBMLT target cells. CD3−IL2−EpCAM was added to see if it blocked the ability of the DT3 (CD3 targeted toxin) to kill HPB-MLT cells. Blocking activity of CD3−IL−2−EpCAM was dose dependent in the presence of 0.1 nM DT3 (A) and 1.0 nM DT3 (B), indicating that the CD3 moiety of CD3−IL2−EpCAM was intact. (C) and (D): the ability of CD3−IL−2−EpCAM to block the killing of negative control CD3− Raji cells by DT2219 (anti-CD22 and CD19 targeted toxin).

FIG. 22. CD16 nanobody was derived from a published llama nanobody (GeneBank sequence EF561291). The CD16 nanobody was spliced to CD19 to test the ability of this CD16 engager to drive NK cell killing. (A) The CD16 nanobody showed cytolytic NK activity similar to rituximab-mediated killing in a chromium release assay with CD19+ Raji targets. (B) The CD16 CDRs were cloned into a humanized camelid scaffold in order to generate HuEF91, a humanized CD16 engager. HuEF91 binding was equivalent to CD16scFv binding, indicating that the humanized HuEF91 did not hinder the specificity of the molecule.

DETAILED DESCRIPTION OF ILLUSTRATIVE EMBODIMENTS

Figure 1:
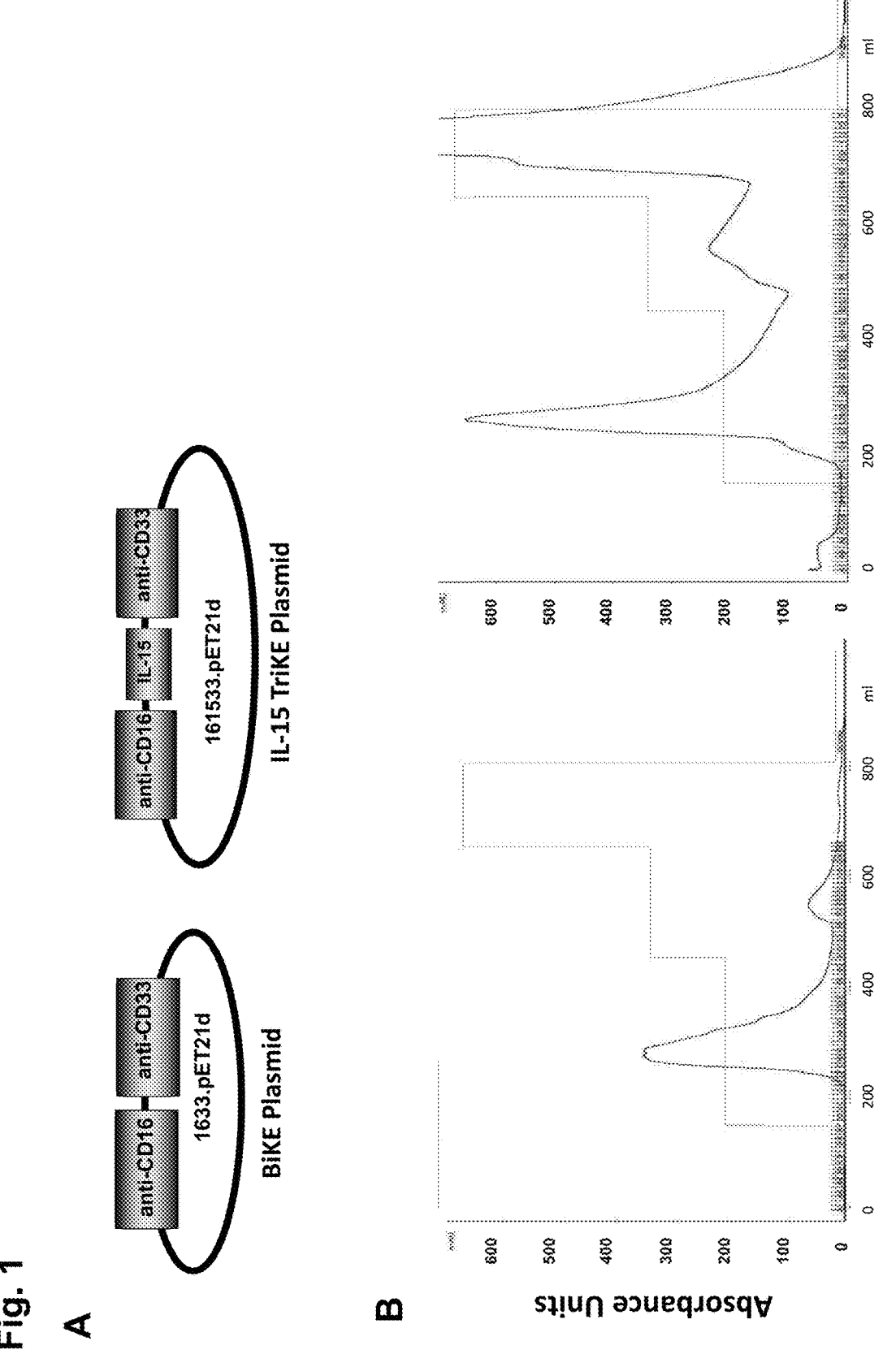
FIG. 1. 161533 trispecific killer engager (TriKE) (SEQ ID NO:1) elicits superior purification properties over 1633 bispecific killer engager (BiKE) (SEQ ID NO:2). (A) Schematic of coding region placement of the BiKE (left) and TriKE (right) domains in the pET expression vector. (B) Absorbance tracing for 1633 BiKE (left) eluted from the ion exchange column as the first phase in drug purification using a three-step elution protocol. The first peak eluted from the column represents the product. In the case of 161533 TriKE (right), the absorbance of peak 1 nearly doubles indicating superior yield. Similar quantity of inclusion bodies were refolded and purified. All protein was removed from the column.

Natural killer (NK) cells are cytotoxic lymphocytes of the innate immune system capable of immune surveillance. Like cytotoxic T cells, NK cells deliver a store of membrane penetrating and apoptosis-inducing granzyme and perforin granules. Unlike T cells, NK cells do not require antigen priming and recognize targets by engaging activating receptors in the absence of MHC recognition.

NK cells express CD16, an activation receptor that binds to the Fc portion of IgG antibodies and is involved in antibody-dependent cell-mediated cytotoxicity (ADCC). NK cells are regulated by IL-15, which can induce increased antigen-dependent cytotoxicity, lymphokine-activated killer activity, and/or mediate interferon (IFN), tumor-necrosis factor (TNF) and/or granulocyte-macrophage colony-stimulating factor (GM-CSF) responses. All of these IL-15-activated functions contribute to improved cancer defense.

Therapeutically, adoptive transfer of NK cells can, for example, induce remission in patients with refractory acute myeloid leukemia (AML) when combined with lymphodepleting chemotherapy and IL-2 to stimulate survival and in vivo expansion of NK cells. This therapy can be limited by lack of antigen specificity and IL-2-mediated induction of regulatory T (Treg) cells that suppress NK cell proliferation and function. Generating a reagent that drives NK cell antigen specificity, expansion, and/or persistence, while bypassing the negative effects of Treg inhibition, can enhance NK-cell-based immunotherapies.

This disclosure describes generating a tri-specific molecule that includes two domains capable of driving NK-cell-mediated killing of tumor cells (e.g., CD33[+] tumor cells and/or EpCAM[+] tumor cells) and an intramolecular NK activating domain capable of generating an NK cell self-sustaining signal. The tri-specific molecule can drive NK cell proliferation and/or enhance NK-cell-driven cytotoxicity against, for example, HL-60 targets, cancer cells, or cancer cell-derived cell lines.

Bi-specific fusions have been made that incorporate an anti-human anti-CD16 scFv derived from a human phage display library technology (McCall et al., 1999. *Mol Immunol.* 36:433-445). NK cells mediate antibody-dependent cell-mediated cytotoxicity (ADCC) through the CD16 (FcγRIII) receptor. Signaling through the CD16 receptor induces calcium fluxes and phosphorylation of ITAMs, triggering the release of lytic granules and cytokines such as interferon (IFNγ) and tumor necrosis factor (TNFα). A bi-specific molecule has been designed to trigger the CD16 receptor in conjunction with other targeting molecules (Gleason et al. Blood. 2014 (19):3016-26), a so-called bispecific killer engager (BiKE). With one scFv recognizing NK cells and a second scFv recognizing a tumor antigen, BiKEs can markedly enhance cytotoxic killing in various human cancers. One exemplary BiKE targeted CD33 and enhanced NK cell responses against acute myeloid leukemia (AML) and myelodysplastic syndrome (MDS). MDS is a clonal heterogeneous stem cell disorder characterized by normal or hypercellular bone marrow (BM) with peripheral blood (PB) cytopenias and an increased risk of progressing to AML.

NK cells are responsive to a variety of cytokines including, for example, IL-15, which is involved in NK cell homeostasis, proliferation, survival, activation, and/or development. IL-15 and IL-2 share several signaling components, including the IL-2/IL-15Rβ (CD122) and the common gamma chain (CD132). Unlike IL-2, IL-15 does not stimulate Tregs, allowing for NK cell activation while bypassing Treg inhibition of the immune response. Besides promoting NK cell homeostasis and proliferation, IL-15 can rescue NK cell functional defects that can occur in the post-transplant setting. IL-15 also can stimulate CD8+ T cell function, further enhancing its immunotherapeutic potential. In addition, based on pre-clinical studies, toxicity profiles of IL-15 may be more favorable than IL-2 at low doses.

IL-15 plays a role in NK cell development homeostasis, proliferation, survival, and activation. IL-15 and IL-2 share several signaling components including the IL-2/IL-15Rβ (CD122) and the common gamma chain (CD132). IL-15 also activates NK cells, and can restore functional defects in engrafting NK cells after hematopoietic stem cell transplantation (HSCT).

This disclosure describes, in one aspect, tri-specific killer engager (TriKE) molecules that generally include one or more NK cell engager domains (e.g., CD16, CD16+CD2, CD16+DNAM, CD16+NKp46), one or more targeting domains (that target, e.g., a tumor cell or virally-infected cell), and one or more cytokine NK activating domains (e.g., IL-15, IL-12, IL-18, IL-21, or other NK cell enhancing cytokine, chemokine, and/or activating molecule), with each domain operably linked to the other domains. As used herein, the term "operably linked" refers to direct or indirect covalent linking. Thus, two domains that are operably linked may be directly covalently coupled to one another. Conversely, the two operably linked domains may be connected by mutual covalent linking to an intervening moiety (e.g., and flanking sequence). Two domains may be considered operably linked if, for example, they are separated by the third domain, with or without one or more intervening flanking sequences.

The NK engaging domain can include any moiety that binds to and/or activates an NK cell and/or any moiety that blocks inhibition of an NK cell. In some embodiments, the NK engaging domain can include an antibody that selectively binds to a component of the surface of an NK cell. In other embodiments, the NK engaging domain can include a ligand or small molecule that selectively binds to a component of the surface of an NK cell. As used herein, the term "selectively binds" refers to the ability to differentiate between two or more alternatives such as, for example, having differential affinity, to any degree, for a particular target. As used herein, "antibody" refers generally an immunoglobulin or a fragment thereof and thus encompasses a monoclonal antibody, a fragment thereof (e.g., scFv, Fab, F(ab')₂, Fv or other modified forms), a combination of monoclonal antibodies and/or fragments thereof, and/or a combination of polyclonal antibodies. Thus, for brevity, reference to an antibody that selectively binds to a component of the surface of an NK cell includes any antibody fragment that exhibits the described binding character. Similarly, reference to a ligand that selectively binds to a component of the surface of an NK cell includes any fragment of the ligand that exhibits the described binding character.

In some embodiments, the NK engaging domain can selectively bind to a receptor at least partially located at the surface of an NK cell. In certain embodiments, the NK engaging domain can serve a function of binding an NK cell and thereby bring the NK into spatial proximity with a target to which the targeting domain—described in more detail below—selectively binds. In certain embodiments, however, the NK engaging domain can selectively bind to a receptor that activates the NK cell and, therefore, also possess an activating function. As described above, activation of the CD16 receptor can elicit antibody-dependent cell-mediated cytotoxicity. Thus, in certain embodiments, the NK engaging domain can include at least a portion of an anti-CD16 receptor antibody effective to selectively bind to the CD16 receptor. In other embodiments, the NK engager cell domain may interrupt mechanisms that inhibit NK cells. In such embodiments, the NK engager domain can include, for example, anti-PD1/PDL1, anti-NKG2A, anti-TIGIT, anti-killer-immunoglobulin receptor (KIR), and/or any other inhibition blocking domain.

One can design the NK engaging domain to possess a desired degree of NK selectivity and, therefore, a desired immune engaging character. For example, CD16 has been identified as Fc receptors FcγRIIIa (CD16a) and FcγRIIIb (CD16b). These receptors bind to the Fc portion of IgG antibodies that then activates the NK cell for antibody-dependent cell-mediated cytotoxicity. Anti-CD16 antibodies selectively bind to NK cells, but also can bind to neutrophils. Anti-CD16a antibodies selectively bind to NK cells, but do not bind to neutrophils. A TriKE embodiment that includes an NK engaging domain that includes an anti-CD16a antibody can bind to NK cells but not bind to neutrophils. Thus, in circumstances where one may want to engage NK cells but not engage neutrophils, one can design the NK engaging domain of the TriKE to include an anti-CD16a antibody.

While described herein in the context of various embodiments in which the NK engaging domain includes an anti-CD16 receptor scFv, the NK engaging domain can include any antibody or other ligand that selectively binds to the CD16 receptor. Moreover, the NK engaging domain can include an antibody or ligand that selectively binds to any NK cell receptor such as, for example, the cell cytotoxicity receptor 2B4, low affinity Fc receptor CD16, killer immunoglobulin like receptors (KIR), CD2, NKG2A, TIGIT, NKG2C, LIR-1, and/or DNAM-1.

The targeting domain can include any moiety that selectively binds to an intended target such as, for example, a tumor cell, a target in the cancer stroma, a target on an inhibitory cell such as myeloid derived suppressor cells that are CD33+, or a target on a virally-infected cell. Thus, a targeting domain can include, for example, an anti-tumor antibody such as rituximab (anti-CD20), afutuzumab (anti-CD20), trastuzumab (anti-HER2/neu), pertuzumab (anti-HER2/neu), labetuzumab (anti-CEA), adecatumumab (anti-EpCAM), citatuzumab bogatox (anti-EpCAM), edrecolomab (anti-EpCAM), arcitumomab (anti-CEA), bevacizumab (anti-VEGF-A), cetuximab (anti-EGFR), nimotuzumab (anti-EGFR), panitumumab (anti-EGFR), zalutumumab (anti-EGFR), gemtuzumab ozogamicin (anti-CD33), lintuzumab (anti-CD33), etaracizumab (anti-integrin $\alpha_v\beta_3$), intetumumab (anti-CD51), ipilimumab (anti-CD152), oregovomab (anti-CA-125), votumumab (anti-tumor antigen CTAA16.88), or pemtumumab (anti-MUC1), anti-CD19, anti-CD22, anti-CD133, anti-CD38 anti-mesothelin, anti-ROR1, CSPG4, SS1, or IGFR1.

In other embodiments, the targeting domain can selectively bind to a target on a cell infected by a virus such as, for example, an adenovirus, HIV, CMV, and/or HPV.

In certain particular embodiments, the targeting domain can include an anti-CD33 antibody. In other particular embodiments, the targeting domain can include an anti-epithelial cell adhesion molecule (EpCAM) antibody.

The NK activating domain can include an amino acid sequence that activates NK cells, promotes sustaining NK cells, or otherwise promotes NK cell activity. The NK activating domain can be, or can be derived from, one or more cytokines that can activate and/or sustain NK cells. As used herein, the term "derived from" refers to an amino acid fragment of a cytokine (e.g., IL-15) that is sufficient to provide NK cell activating and/or sustaining activity. In embodiments that include more than one NK activating domain, the NK activating domains may be provided in series or in any other combination. Additionally, each cytokine-based NK activating domain can include either the full amino acid sequence of the cytokine or may be an amino acid fragment, independent of the nature of other NK activating domains included in the TriKE molecule. Exemplary cytokines on which an NK activating domain may be based include, for example, IL-15, IL-18, IL-12, and IL-21. Thus, while described in detail herein in the context of an exemplary model embodiment in which the NK activating domain is derived from IL-15, a TriKE may be designed using an NK activating domain that is, or is derived from, any suitable cytokine.

For brevity in this description, reference to an NK activating domain by identifying the cytokine on which it is based includes both the full amino acid sequence of the cytokine, any suitable amino acid fragment of the cytokine, and or a modified version of the cytokine that includes one or more amino acid substitutions. Thus, reference to an "IL-15" NK activating domain includes an NK activating domain that includes the full amino acid sequence of IL-15, an NK activating domain that includes a fragment of IL-15, or an NK activating domain such as, for example, IL-15N72D or IL-15N72A, that includes an amino acid substitution compared to the wild-type IL-15 amino acid sequence.

The use of an IL-15 NK activating domain in a TriKE can provide sustained NK cell activity—as evidenced in a mouse model showing human NK cells are dramatically elevated and cancer reduced—even after three weeks. NK cells are activated in mice to produce an array of anti-cancer factors and cytokines. Moreover, FIG. 1 shows that an IL-15 NK activating domain somehow alters the chemistry of these molecules so that they refold more easily and/or are recoverable in greater yield, thus rendering the TriKE molecules more suitable for clinical scale-up.

Figure 7:
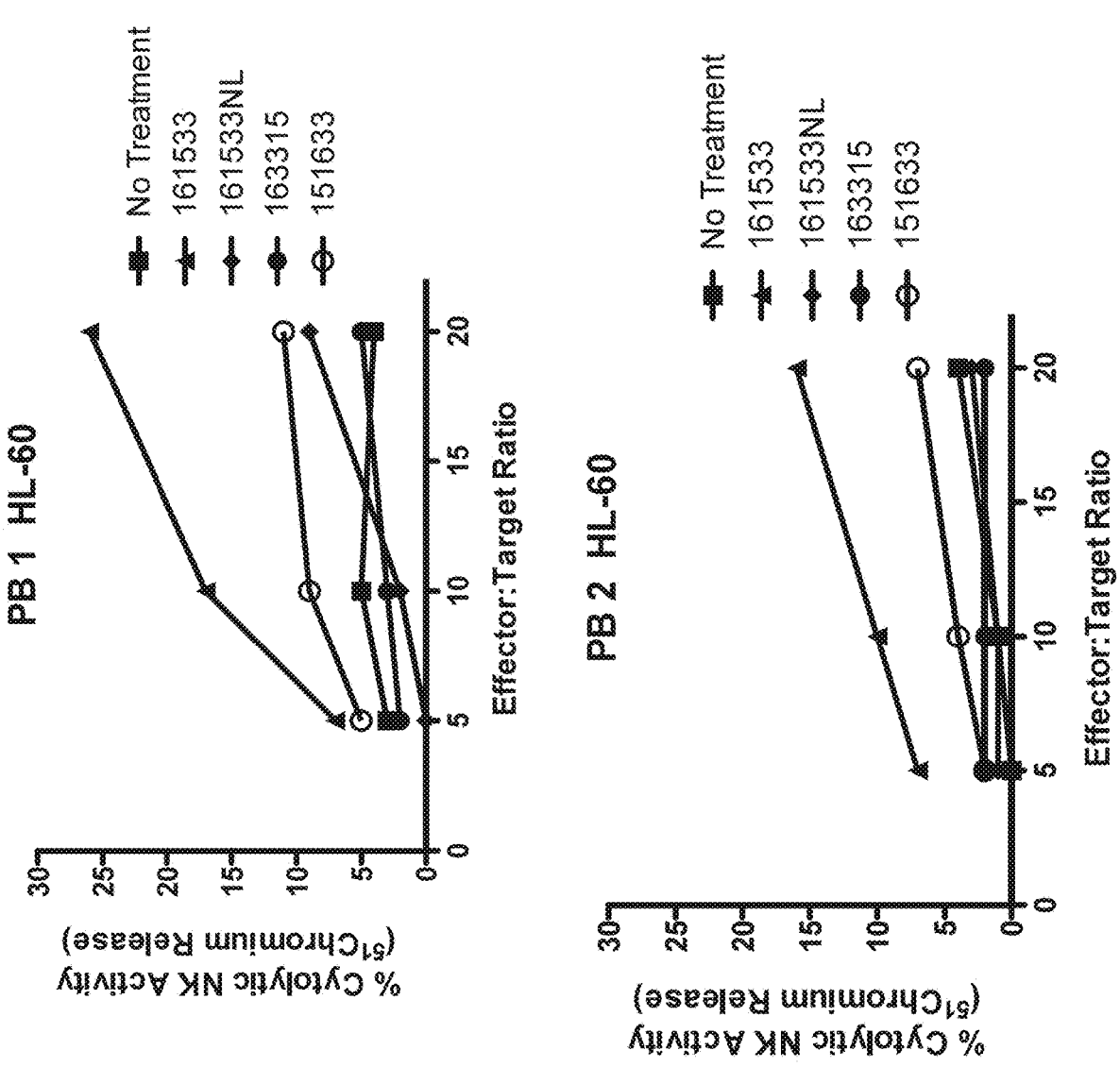
FIG. 7. The flanking sequences and the orientation of the TriKE molecule both influence its function. In order test the influence of the flanking sequences, a variant of 161533 (161533NL, SEQ ID NO:5) was constructed that lacked the flanking sequences (PSGQAGAAASESLFVSNHAY, SEQ ID NO:3; and EASGGPE, SEQ ID NO:4) on either side of the IL-15 domain of the 161533 construct. Freshly isolated PBMCs (containing 3.5% NK cells for this example) from two independent donors (PB1 and PB2) were cultured with chromium loaded HL-60 cells for four hours at an E:T ratio of 20:1. Noted reagents were added at the beginning of co-culture at a 20 nM concentration. Data is displayed as % NK cell cytolytic activity. 161533 reflects the construct that includes the modified IL-15 NK activating domain with the flanking sequences intact. The data indicate that the IL-15 NK activating, domain with flanking sequences enhances TriKE function To examine the effects of orientation, the construct was synthesized with IL-15 on either the N terminus (151633; SEQ ID NO:6) or the C terminus (163315; SEQ ID NO:7) and compared to wildtype 161533 with IL-15 as a cross-linker. The data generated IL-15 in the center of the molecule optimizes NK cytolytic activity.

In some embodiments, the molecule can further include a flanking sequence that can link two of the above-described domains. In some embodiments, the presence of the flanking sequence can further increase NK cell activation. One exemplary flanking sequence includes the 20 amino acids of SEQ ID NO:3. Another exemplary flanking sequence includes the seven amino acids of SEQ ID NO:4. Certain embodiments (e.g., the 161533 TriKE, SEQ ID NO:1) can include more than one flanking sequence. As one example, SEQ ID NO:1 includes the flanking sequence of SEQ ID NO:3 to link the NK engaging domain (e.g., anti-CD16 receptor scFv) with the NK activating domain (e.g., IL-15). SEQ ID NO:1 also includes the flanking sequence of SEQ ID NO:4 to link the NK activating domain with the targeting domain (e.g., anti-CD33 scFv). FIG. 7 shows data demonstrating that constructs that lack a flanking sequence exhibit reduced activity compared to constructs that possess the flanking sequence.

Synthesis and Purity of a 161533 TriKE

Figure 1C:
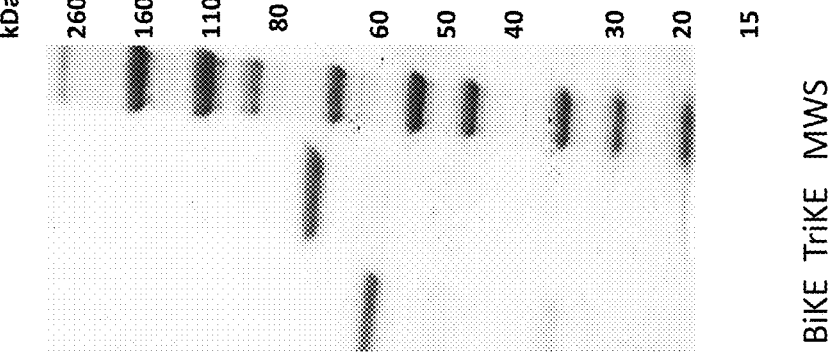
FIG. 1C. SDS-PAGE gel and Coomasie Blue staining after a second step purification over a size exclusion column. Densitometry analysis indicates that the product is over 95% pure.

To create an exemplary model therapeutic TriKE that is antigen specific and self-sustains the NK cell response against leukemia, a human modified IL-15 cross-linker was introduced into the 1633 BiKE creating a 161533 TriKE (FIG. 1A). The FPLC profile of the TriKE indicated a high yield product from a bacterial expression system that required refolding (FIG. 1B). The IL-15 NK activating domain reduced the isoelectric point by two pH units, creating more favorable conditions for purification and enhancing yield. Despite purification beginning with identical amounts of inclusion bodies, the final yield of 161533 TriKE was twice the yield of the comparable BiKE (1633, with no IL-15 NK activating domain), indicating more favorable purification dynamics. Products were >95% pure by SDS-PAGE gel analysis and Coomasie Blue Staining (FIG. 1C). To verify that binding and specificity remained intact in the new TriKE molecule, selectivity was measured by direct binding and blocking flow cytometry assays against CD33[+]EpCAM[31] HL-60 cells and CD33[-]EpCAM[+] HT-29 cells (Table 1 and Table 2).

TABLE 1

| Binding of BiKE and TriKE Measured by Flow Cytometry | | | |
|---|---|---|---|
| Reagent | Cell Line | Drug Amount (μg) | % Positive Cells |
| Unstained | HL-60 | — | 0.1 |
| 161533-FITC | HL-60 | 10 | 63 |
| 161533-FITC | HL-60 | 20 | 75 |
| 161533-FITC | HL-60 | 40 | 78 |
| 161533-FITC | HT-29 | 10 | 4 |
| EpCAM-FITC | HL-60 | 20 | 1.4 |
| EpCAM-FITC | HT-29 | 2 | 100 |
| 1633-FITC | HT-29 | 4 | 1 |
| 1633-FITC | HL-60 | 4 | 62 |
| 1633-FITC | HL-60 | 15 | 74 |
| 16-FITC | HL-60 | 20 | 0.1 |
| 33-FITC | HL-60 | 20 | 98 |

13

TABLE 2

| Specificity Determined by Antigen Blockade | | | |
| --- | --- | --- | --- |
| Reagent | Cell Line | Blocking Agent | % Positive Cells |
| 1633-FITC | HL-60 | None | 52 |
| 1633-FITC | HL-60 | anti-CD33 | 1 |
| 161533-FITC | HL-60 | None | 85 |
| 161533-FITC | HL-60 | anti-CD33 | 4 |
| 161533-FITC | HL-60 | anti-CD45 | 73 |

161533 TriKE Increases NK Cell Function

Figure 2:
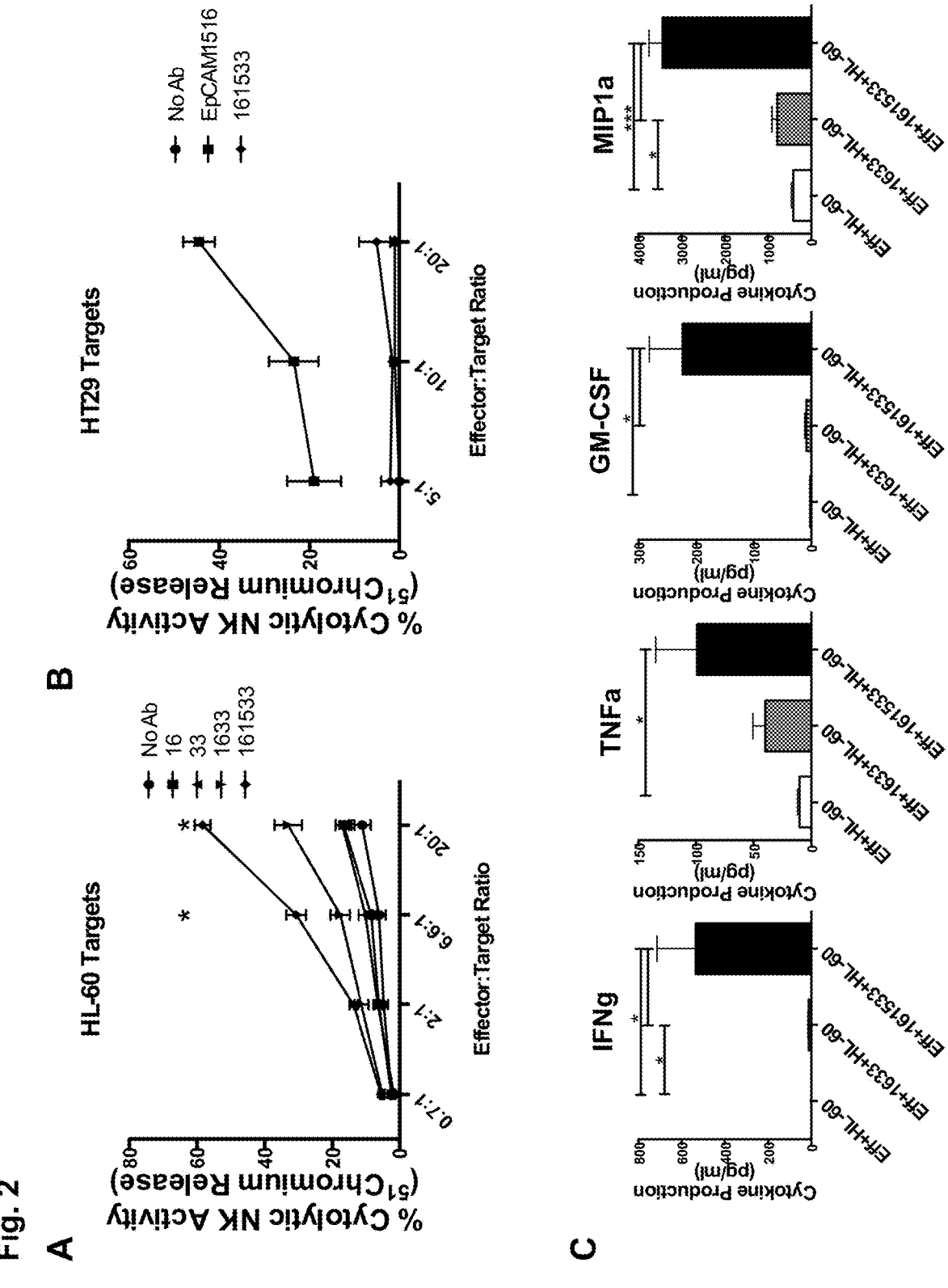
FIG. 2. 161533 TriKE elicits superior NK cell function against targets. The release of the isotope chromium-51 ($^{51}$Cr) is often used to measure NK cell function (killing). (A) Freshly isolated PBMCs were cultured with chromium loaded HL-60 cells for four hours at E:T ratios of 20:1, 6.6:1, and 2:1. Noted reagents were added at the beginning of co-culture at a 20 nM concentration. Data is displayed as % NK cell cytolytic activity. Given the number of conditions, significance only noted between 1633 and 161533 molecules. n=3. (B) To evaluate specificity of 161533 TriKE, $^{51}$Cr release assay was performed against CD33$^-$EpCAM$^+$ HT29 targets. EpCAM1533 TriKE was used as a positive control. n=2. (C) NK cells were enriched from normal donor PBMCs utilizing magnetic beads and placed in culture with HL-60 targets (10:1) alone or in the presence of 1633 BiKE or 161533 TriKE for 24 hours. At the end of the incubation supernatants were taken from each of the cultures and frozen down for later assessment of secreted IFNγ, TNFα, GM-CSF, and MIP1a through Luminex multiplex assay (n=5). Points and Bars represent mean±SEM.

To determine whether inclusion of IL-15 retained the ability of bioengineered 1633 to mediate ADCC, 1633 and 161533 were compared in a 4-hour chromium release assay where PBMCs from healthy donors were tested for their ability to kill CD33$^+$ HL-60 targets (FIG. 2A). The 161533 TriKE induced higher NK cell mediated killing than the BiKE, particularly at the 20:1 ratio (58.3±2.3% vs. 33±4%, P=0.0184). Control samples of anti-CD16 and anti-CD33 did not augment the response compared to the untreated controls showing no activity of these components alone. To test specificity in a cytotoxic assay the 161533 TriKE was incubated with NK cells and CD33$^-$ HT-29 target cells (FIG. 2B). The 161533 TriKE showed no significant increases in killing of HT-29 cells when compared to the no treatment control. To ensure that HT-29 target cells are not merely more resistant as an explanation for specificity, the HT-29 cells were incubated with a novel IL-15 TriKE containing an anti-EpCAM scFv instead of anti-CD33. This TriKE robustly killed EpCAM$^+$ HT-29 cells, highlighting the versatility of the IL-15 NK activating domain TriKE platform against both hematologic malignancy and solid tumor malignancies.

Besides redirected cytotoxicity, another function of NK cells is to produce cytokines and chemokines upon target cell recognition. To test if the TriKE enhances this process NK cells and HL-60 targets were incubated without molecules, with 1633 BiKE, or with 161533 TriKE and supernatants where collected after 24 hours and analyzed for inflammatory cytokines and chemokines (FIG. 2C). When compared to no drug or the BiKE, the TriKE significantly induced IFNγ, TNFα, GM-CSF, and MIP-1a secretion. These data indicate that the IL-15 molecule in the TriKE can induce pro-inflammatory cytokine and chemokine secretion which may increase the anti-tumor activity of NK cells.

161533 TriKE Induces Survival and Expansion of Post-Transplant NK cells

One therapeutic advantage of IL-15 is that it is involved in homeostasis and expansion of NK cells. Thus, the 161533 TriKE was tested to evaluate if these biological functions remain active within the TriKE molecule. To test this in a physiologically relevant context, early post-transplant patient samples were used. These samples provide a setting where NK cell reconstitution is needed to mediate anti-tumor graft versus leukemia (GvL) responses. Evaluation of time points early after transplant are of particular interest because defects in NK-cells mediated target-cell-induced cytokine production at these same time points, which may account for early relapse (Foley et al., 2014. *Immunol Rev* 258(1):45-63). Post-transplant patient PBMCs (either day 100 [n=5] or earlier 20-44 [n=5] after transplant) were labeled with CELLTRACE dye (Thermo Fisher Scientific, Waltham, Mass.) to measure proliferation, incubated with HL-60 targets and either 1633 BiKE or 161533 TriKE for seven days, and then labeled with Live/Dead dye to measure NK cell survival. Within the PBMCs that were incubated with the 1633 BiKE, most of the NK cells incorporated Live/Dead dye, indicating poor survival. In contrast, patient PBMCs incubated with the 161533 TriKE supported excellent NK cell survival (FIGS. 3A and 3B; 96.9±0.5% vs. 21±5.4%; P<0.0001). To understand if the IL-15 moiety in the 161533 TriKE also drove proliferation, CELLTRACE dye dilution in the viable NK cell population was evaluated. Unexpectedly, the 161533 TriKE induced robust and specific NK cell proliferation in the post-transplant patient samples, with minimal proliferation of T cells (FIGS. 3C and 3D) in the same sample (79.1±2.5% of the NK cells divided vs. 2.3±1.1% of the T cells, P<0.0001). The NK cells also had a significantly higher expansion index than total T cells (7.2±0.8% vs. 1.1±0.1%, P<0.0001), which represents total fold expansion. This suggests that the activity of IL-15 in the 161533 TriKE may be more NK cell specific as a result of the flanking scFv molecules in the construct. Moreover, incubating NK cells with the 161533 TriKE resulted in robust proliferation that mirrored expansion mediated by a saturating concentration of IL-15. Thus, an IL-15 NK activating domain in the TriKE is functionally active and capable of delivering a self-sustaining signal to healthy donor NK cells and/or can drive survival and proliferation of post-transplant patient NK cells, a setting where NK cell reconstitution is defective.

161533 TriKE Rescues Defective NK Cell Function Early After Transplantation

Figure 4:
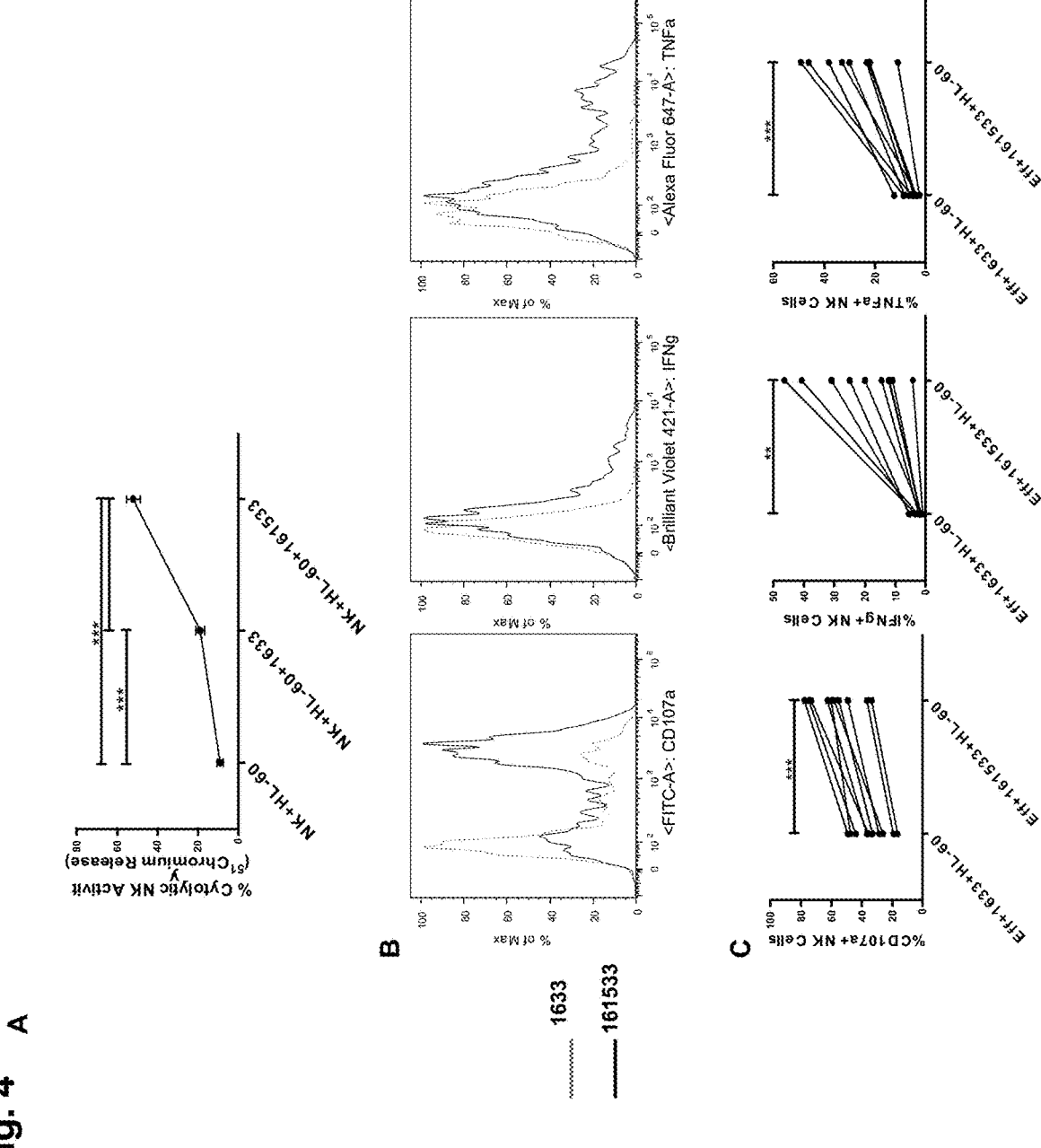
FIG. 4. 161533 TriKE potently rescues NK cell function in post-transplant samples. Post-transplant patient PBMCs were thawed and rested overnight. The next night they were incubated with no drug, 1633 BiKE (50 nM), or 161533 TriKE (50 nM). The next morning they were washed and given same treatment as the night before (to ensure that there are no issues with molecule internalization). (A) PBMCs with noted treatment groups were incubated with chromium loaded HL-60s for four hours and % cytolytic activity was calculated. Dot and bars denote mean±SEM (n=9). (B) Representative histograms and (C) pooled data of CD107a (left panels), IFNγ (center panels), and TNFα (right panels) expression on CD56$^+$CD3$^-$ NK cells after four-hour incubation with HL-60 targets. Dots denote individual patient samples (n=10).

After allogeneic hematopoietic stem cell transplant, NK cells are increased in number and respond to IL-12 and IL-18 stimulation but exhibit hyporesponsiveness for more than six months when exposed to cancer cell line targets. In this setting, short-term exposure to overnight incubation with IL-15 can rescue NK cell function against K562 targets (Foley et al., 2011, *Blood* 118(10):2784-2792). Given the potential clinical development of the exemplary TriKE 161533 molecule as post-transplant immunotherapy, the TriKE and the comparable BiKE (1633) molecules were tested on post-transplant PBMCs from allogeneic sibling hematopoietic stem cell transplant recipients (FIG. 4). 1633 BiKE or 161533 TriKE were incubated with NK cells overnight, to allow for functional recovery, and cells were incubated with HL-60 targets the next morning and analyzed for function. Although incubation with the 1633 BiKE resulted in a doubling of killing of HL-60 targets when compared to just NK cells against HL-60 targets (18.9±2.1% versus 9±1.5%, P<0.0001), incubation with the 161533 TriKE potently rescued NK cell-mediated cytotoxic function to a much great degree (52.1±3.5%) than by the BiKE (FIG. 4A). The increase in cytotoxicity correlated well with increased degranulation measured by CD107a expression (FIGS. 4B and 4C left panel). Compared to the BiKE, the TriKE potently rescued IFNγ (BiKE=2.6±0.5% vs. TriKE=21.7±4.4%, P=0.0012) and TNFα (BiKE=6.1±1% vs. TriKE=29.9±3.8%, P<0.0001) production (FIGS. 4B and 4C center and right panels). In all assays, the TriKE induced increased functionality when compared to the BiKE. The magnitude of these changes clearly illustrate the immunotherapeutic potential of the 161533 TriKE in the early post-transplant setting.

161533 TriKE Increases NK Cell Function Against Primary AML Blasts

Figure 5:
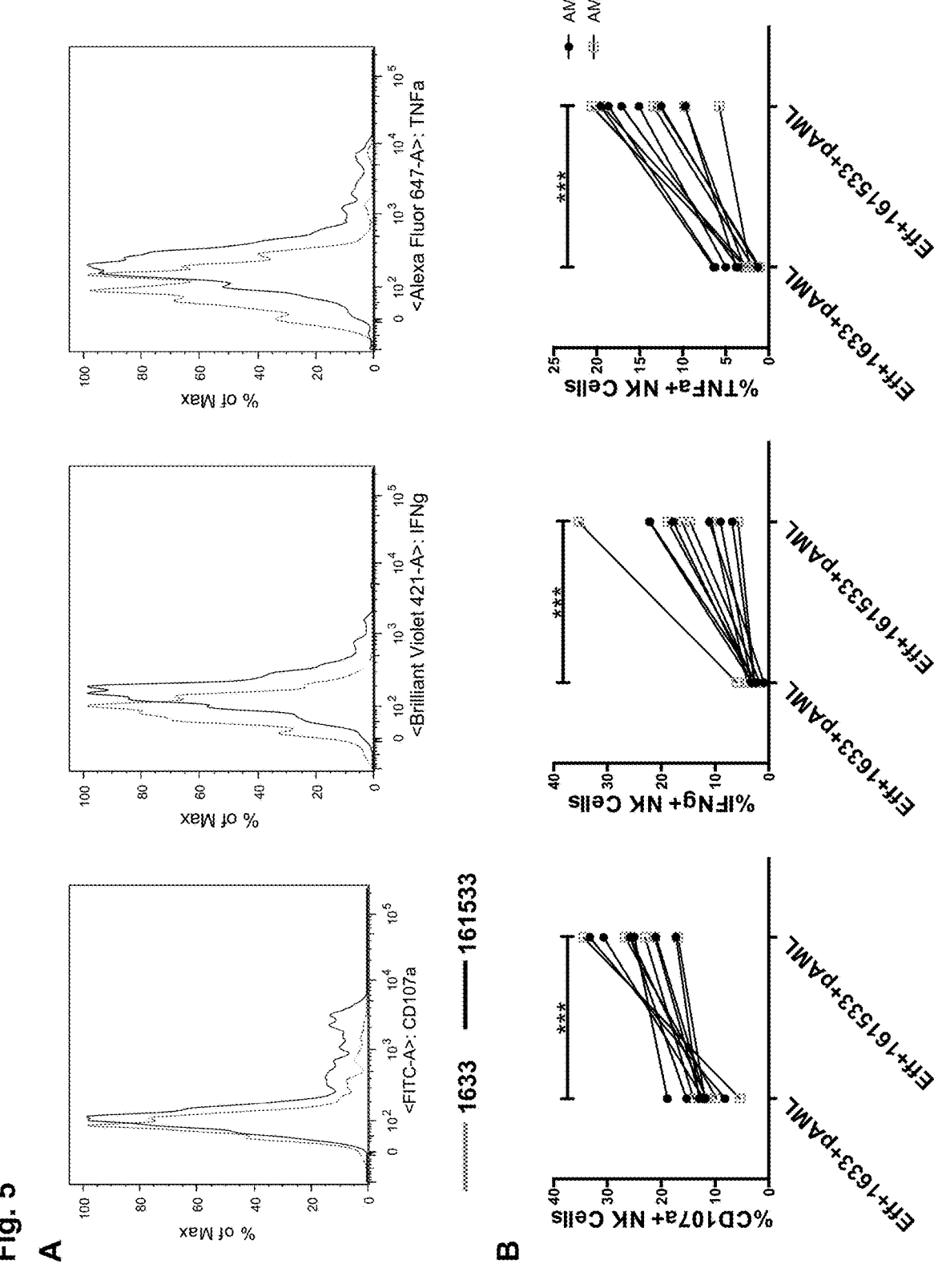
FIG. 5. 161533 TriKE enhances NK cell function against primary AML blasts compared to BiKE. Post-transplant patient PBMCs were thawed and rested overnight. The next night they were incubated with 1633 BiKE (50 nM), or 161533 TriKE (50 nM). The next morning they were washed and given same treatment as the night before (to ensure that there are no issues with molecule internalization). Primary AML blasts from apheresis products of two separate patients were thawed and rested overnight. Treated post-transplant patient PBMCs (n=6) were incubated with the two different primary AML blasts (n=12 total) for four hours and NK cell function was assessed by flow cytometry. NK function can be assessed by measuring lytic degranulation in the form of CD107a. (A) Representative histograms denoting CD107a (left), IFNγ (center), and TNFα (right) expression on post-transplant patient NK cells treated with 1633 BiKE (gray) or 161533 TriKE (black) after four-hour incubation with primary AML blasts. (B) Pooled data for CD107a (left), IFNγ (center), and TNFα (right) expression on post-transplant patient NK cells treated with 1633 BiKE and 161533 TriKE and incubated with primary AML blasts. Each box represents a separate post-transplant patient sample incubated against two separate patient AML blast targets, denoted by filled and open boxes (n=12 total).

To compare the activity of 1633 BiKE and 161533 TriKE against primary AML blasts, PBMCs from post-transplant patients were incubated with primary AML blasts from two different patients (AML1 and AML2). CD107a, IFNγ and TNFα induction was reduced against the primary blasts compared to HL-60 targets (FIG. 5 vs. FIG. 4). The decrease in function could be attributed in part to decreased expression of CD33 on primary blasts, but expression of inhibitory ligands or absence of activating receptor ligands may also contribute to the decreased function. While no significant differences were seen in NK cell activation between AML1 and AML2 under the same conditions, PBMCs from post-transplant patient samples incubated with the 161533 TriKE significantly (p<0.05) induced greater degranulation (CD107a) and cytokine production (IFNγ and TNFα) over the PBMCs incubated with the 1633 BiKE (FIG. 5A and FIG. 5B), suggesting that the combination of activation combined with IL-15 is potent against primary AML targets. Taken together, these in vitro data indicate that the 161533 TriKE can make NK cells antigen specific against primary tumor cells.

161533 TriKE Induces Enhanced In Vivo NK Cell Survival and Function

Figure 6:
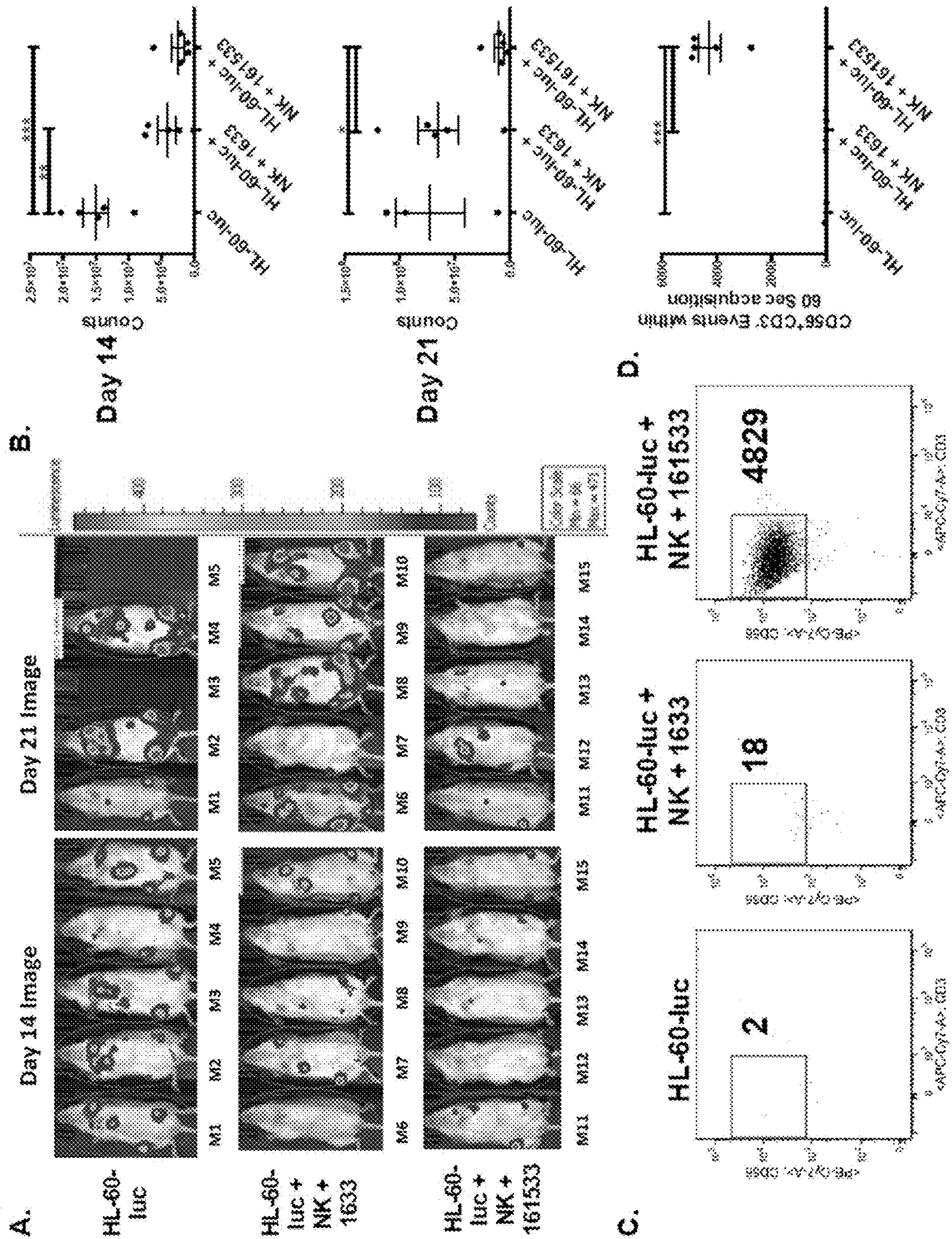
FIG. 6. 161533 TriKE limits HL-60 tumor growth in vivo better than 1633 BiKE. HL-60-luc cells were injected iv (7.5×10$^5$ cells/mouse) into NSG mice and three days later one million human NK cells activated overnight with IL-15 were infused. The 1633 BiKE and 161533 TriKE groups received HL-60-luc and NK cells, while the control group only received HL-60-luc cells. Drug (50 µg/kg) was administered MWF throughout the study. (A) Individual mouse photoluminscence at day 14 (top) and day 21 (bottom) of study in a two-minute exposure (n=5 per treatment (unless mice died), representative of two separate experiments). (B) Quantification of luminescence in mice from the three treatment groups at day 14 (left) and day 21 (right). Each dot represents a different mouse and bars denote mean±SEM (n=5, representative of two separate experiments). (C) Blood was collected on day 20 from the mice in each of the experiential treatment groups. Circulating CD56+CD3– human NK cells were quantified by flow cytometry. Events were collected over 60 seconds and the number of human NK cell events was calculated. Representative dot plots are shown denoting the number of NK (CD56+.CD3–) cell events within the CD45+ gate. (D) Aggregate data demonstrating the number of human NK cell events in each treatment group at day 20. Individual dots represent different mice and bars denote mean SEM (n=3 for HL-60-luc group [two mice died], n=5 for the 1633 BiKE and 161533 TriKE groups).

Comparing the in vivo activity of BiKE and TriKE required the development of a murine xenograft model that simultaneously accommodated the progression of CD33+ leukemia and human NK cells. HL-60 cells containing a luciferase reporter were injected intravenously ($7.5×10^5$ cells/mouse) and then three days later, 1 million human NK cells activated overnight with IL-15 were infused. FIG. 6 shows imaging data depicting HL-60-luc tumor load in each of the treatment groups. While the control group received only HL-60-luc cells, but no drug or NK cells, the 1633 BiKE and 161533 TriKE groups received HL-60-luc cells and NK cells. Drug (50 µg/kg) was administered MTWThF throughout the study. On day 14 (FIG. 6B), BiKE and TriKE groups significantly (p<0.05) differed from the control group but not each other indicating that at early time points both BiKE and TriKE impact tumor progression similarly. On day 21, however, no significant differences could be found between the no drug group and the BiKE group in surviving, although two mice from the no drug group died by this point. The TriKE group on the other hand significantly (p<0.05) differed from the control group, and at this time point also differed from the BiKE group, indicating superior control of the HL-60 tumor burden at later stages with 161533 TriKE therapy.

Figure 3:
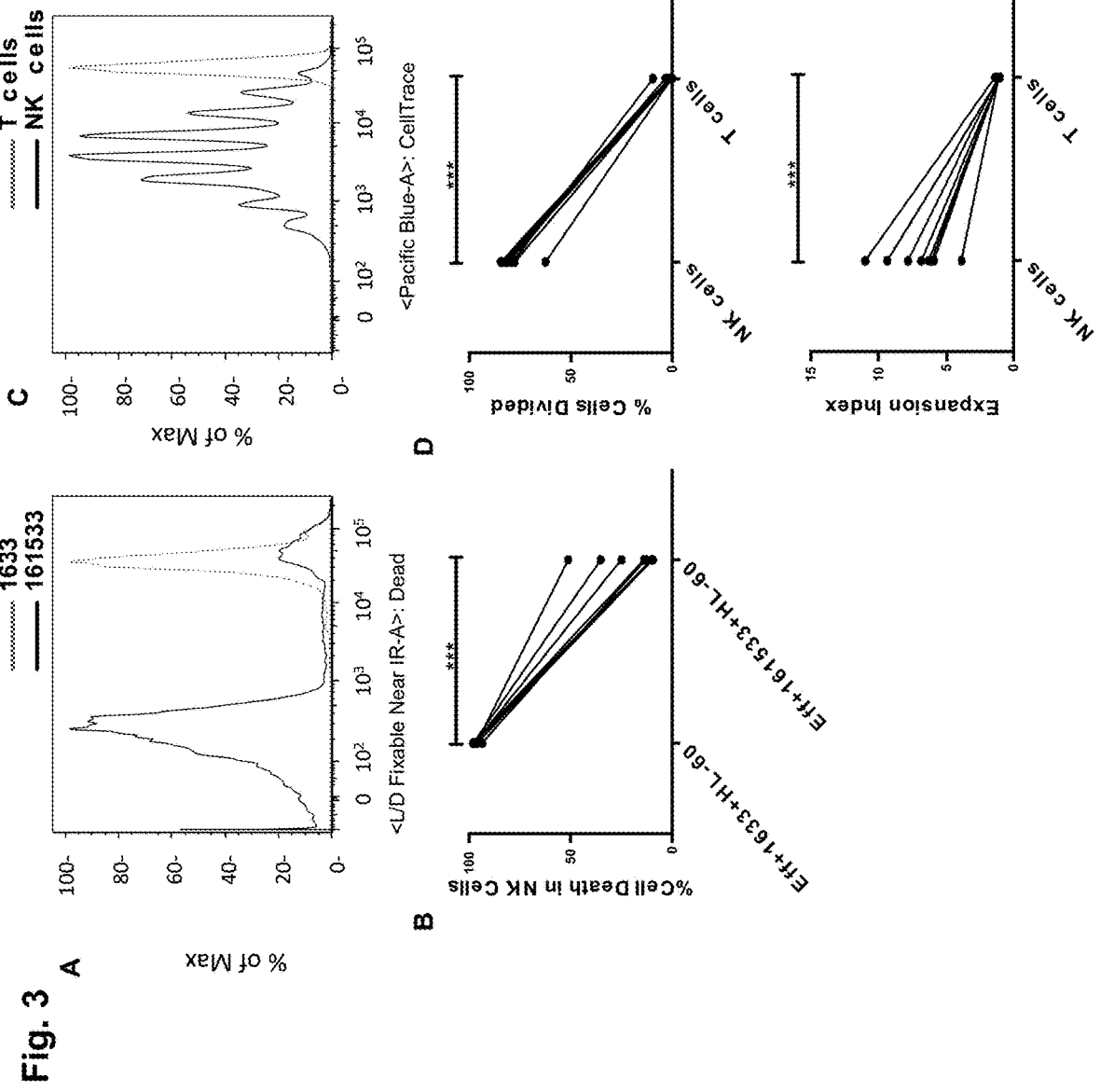
FIG. 3. The 161533 TriKE mediates NK cell proliferation and expansion. Post-transplant patient PBMCs were loaded with CELLTRACE proliferation dye (Thermo Fisher Scientific, Waltham, Mass.) and co-cultured with HL-60 Targets at a 5:1 (E:T) ratio for seven days in the presence of 50 nM 1633 BiKE or 161533 TriKE. At the end of the incubation CD56$^+$CD3$^-$ NK cells were assessed for viability through Live/Dead Near IR staining. (A) Individual histogram and (B) pooled analysis of viability in the NK cell population treated with the 1633 BiKE (gray) or 161533 TriKE (black). (C) Proliferation was then assessed by CELLTRACE dilution in the live CD56$^-$CD3$^+$ T cells (gray) and CD56$^+$CD3$^-$ NK cells (black) within the TriKE group. (D) Pooled analysis demonstrating % cells divided (top) and expansion index (bottom), which is a calculation of the fold expansion within the population given the amount of CELLTRACE dilution. Individual dots represent separate post-transplant samples (n=8).

Given the NK cell survival and proliferation results noted in the in vitro experiments from FIG. 3, the increased control of HL-60-luc tumor generated by the TriKE in vivo might be mediated, at least in part, by increased maintenance and expansion of the transferred NK cell population through IL-15 moiety in the 161533 TriKE molecule. Thus, mice were bled (20 µL) at day 20 and the number of NK cell (CD56+CD3−) events acquired during a fixed acquisition time (60 sec) was evaluated. Neither the control nor the 1633 BiKE treated animals showed significant evidence of circulating CD56+CD3− human NK cells showing poor survival and expansion under these conditions (FIGS. 6C and 6D). In marked contrast, all of the 161533-TriKE-treated animals showed high levels of human NK cells (4261±410.6 events). Mice treated with 161533 TriKE had NK cell levels that were nearly 200-fold greater than BiKE NK levels indicating a robust biological contribution of the IL-15 molecule as an NK activating domain within the TriKE molecule. Thus, use of an IL-15 NK activating domain in the TriKE can reduce the need for therapy to include providing exogenous IL-15 to sustain NK cell numbers.

Flanking Sequences and Orientation Influence TriKE Activity

A variant of the 161533 construct was designed without the flanking sequences on either side of IL-15 in order to test the influence of the flanking sequences on the functionality of the molecule. The new variant, identified herein as 161533NL (SEQ ID NO:5), was compared to the 161533 construct (SEQ ID NO:1) in chromium release killing assays. FIG. 7 shows in two independent donors (PB-1 and PB2) that flanking sequences influence the activity of the TriKE. Orientation variants also were constructed with IL-15 in the N-terminus (151633; SEQ ID NO:6) and C-terminus (163315; SEQ ID NO:7) positions. FIG. 7 also shows that the 161533 construct, which includes IL-15 in the center position as a cross-linker and possesses the flanking sequences, results in greater NK cell cytolytic activity. Without the flanking sequences, 161533NL exhibited cytotoxicity at an E:T ratio of 20:1 of 25% compared to the parental wildtype 161533 (57%), confirming that the flanking sequences generally increase the NK cell cytolytic activity induced of TriKE constructs.

1615EpCAM TriKE

Figure 8:
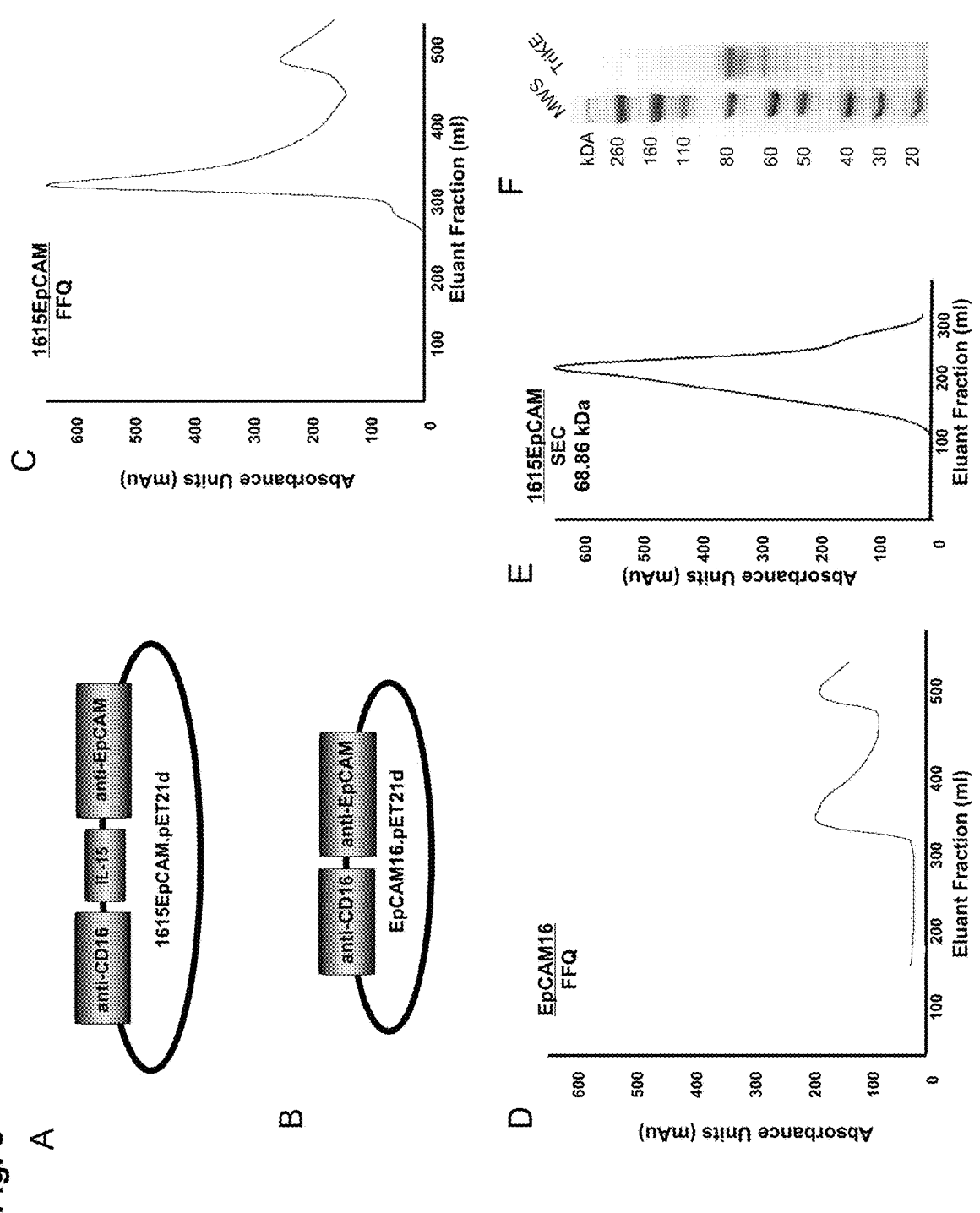
FIG. 8. 1615EpCAM TriKE (SEQ ID NO:8) elicits superior purification properties over EpCAM16 BiKE. (A) Schematic of placement of the coding regions for the TriKE (1615EpCAM) domains in the pET expression vector. (B) Schematic of placement of coding regions for the BiKE (16EpCAM) domains in the pET expression vector. (C) Absorbance tracing of the TriKE (1615EpCAM) eluted from the ion exchange column as the first phase in drug purification using a three-step elution protocol. The first peak eluted from the column represents the product. (D) Absorbance tracing of the BiKE (16EpCAM) eluted from the ion exchange column as the first phase in drug purification using a three-step elution protocol. The first peak eluted from the column represents the product, recovered at a lower yield than the TriKE. (F) SDS-PAGE gel and Coomasie Blue staining after a second step purification (E) over a size exclusion column. Densitometry analysis indicates that the product is over 95% pure.

To construct a self-sustaining hybrid immune engager, a 1615EpCAM TriKE (FIG. 8A, SEQ ID NO:8) was assembled by incorporating human IL-15 into the EpCAM16 BiKE (FIG. 8B). The TriKE construct contains DNA fragments encoding the $V_H$ and $V_L$ regions of an anti-CD16 scFv, spliced to IL-15 and then to the $V_H$ and $V_L$ regions of an anti-EpCAM scFv. The IL-15 DNA fragment is flanked on either side by a 20 amino acid (aa) segment (SEQ ID NO:3) and EASGGPE (SEQ ID NO:4). Absorbance tracing for 1615EpCAM TriKE and EpCAM16 BiKE eluted from the FFQ ion exchange column as the first phase in drug purification using a three-step elution protocol are displayed in FIGS. 8C and 8D, respectively. The first peak eluted from the column represents the product of interest. When a similar quantity of inclusion bodies were refolded and purified, yield was unexpectedly improved with the addition of the IL-15 cross linker. When compared to the EpCAM16 BiKE, absorbance nearly tripled in the 1615EpCAM TriKE indicating superior yield. SDS-PAGE gel and Coomasie Blue staining show purity after both ion exchange and size exclusion column purifications (FIGS. 8E and 8F) resulting in a product that is over 90% pure with a size of about 68860 kDa. Thus, just as observed with the 161533 TriKE (SEQ ID NO:1), incorporating IL-15 directly into a hybrid TriKE confers superior purification properties in comparison to the corresponding BiKE—in this case, EpCAM16—lacking IL-15.

1615EpCAM TriKE Induces Chromium-51 Release

Figure 9:
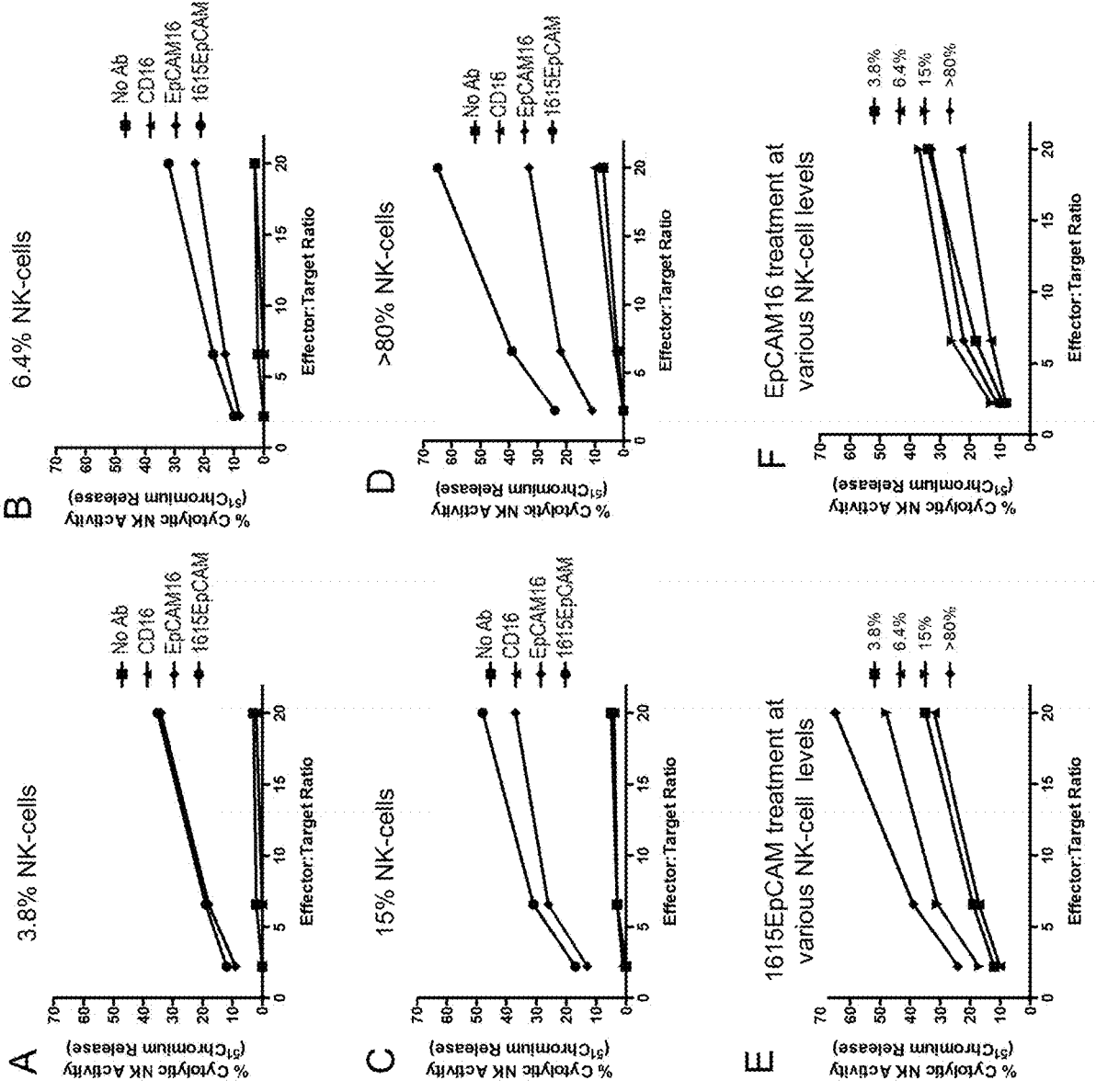
FIG. 9. Evaluation of the activity of the 1615EpCAM TriKE (SEQ ID NO:8) in chromium release assays. Freshly isolated Natural killer (NK)-cells were added to HT-29 cells (human colorectal carcinoma cell line) with the respective effector:target ratios as indicated. Donors were chosen with naturally different levels of circulating NK cells (A) peripheral blood mononuclear cells (PBMC) with 3.8% NK cells, (B) PBMC with 6.4% NK cells, (C) 15% and (D) >80% NK cells enriched from PBMC. (E) Higher levels of kill with 1615EpCAM correlated with donors with naturally higher levels of NK killing. In (E), only the curves for 1615EpCAM were compared for the four donors, emphasizing the direct correlation between NK presence and cytolytic activity induced by the drug. (F) shows that in the case of 16EpCAM, no such correlation exists.

To determine the functional activity of 1615EpCAM, its killing ability was measured in standard [51]chromium release assays (FIG. 9). To determine the effect of incorporating IL-15 into the EpCAM16 scaffold, NK-cell-mediated cytotoxicity was evaluated in a wide range of donors having different NK cell contents. Freshly isolated PBMCs were added to HT-29 cells at Effector (E):Target (T) ratios of 20:1, 6.6:1, and 2.2:1, generating cytolytic curves. The engineered reagents were added at the concentration of 30 nM (maximum effective dose after titration experiments). Donors with 3.8%, 6.4%, 15%, and enriched NK cells >80% (as determined by flow cytometry) showed that the IL-15 component generally improves the killing capabilities of NK cells (FIGS. 9A, 9B, 9C, and 9D, respectively). In FIG. 9E, only the donor curves for 1615EpCAM were graphed, emphasizing a direct correlation between increasing NK presence and cytolytic activity. FIG. 9F shows that for EpCAM16, no such correlation exists. Due to baseline variation, reproducibility was ensured by repetition with different donors. Together, the data indicate that greater the number of NK cells in the assay, the greater the observed NK cytolytic activity.

Figure 10:
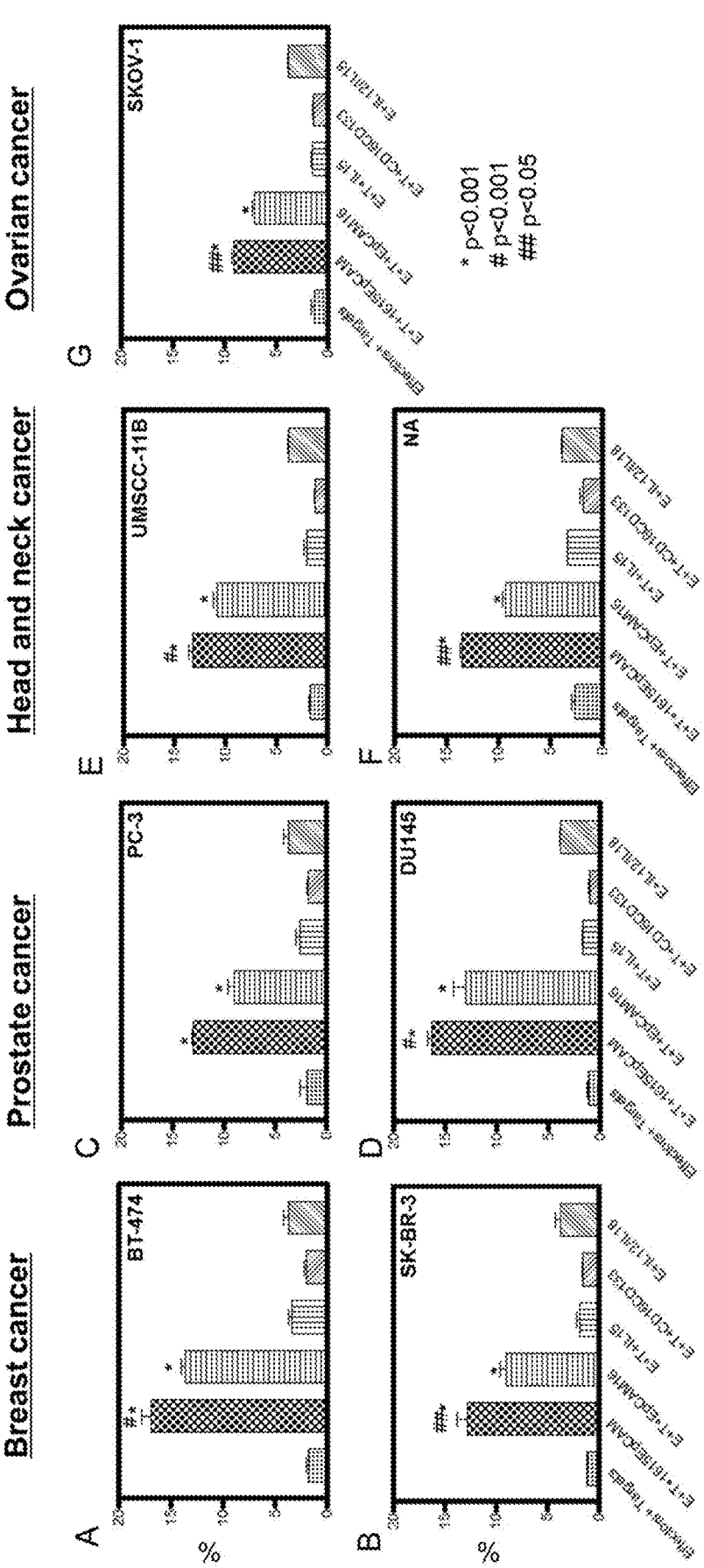
FIG. 10. Lytic degranulation in different EpCAM expressing target cancer cell lines. As mentioned, NK function can be measured by quantitating CD107a expression as a measure of lytic degranulation. CD107a expressing cells were evaluated within the gated $CD56^+CD3^-$ NK cell population. Effector PBMCs were incubated with different EpCAM bearing target cell lines including (A) BT-474, (B) SK-BR-3, (C) PC-3, (D) DU145, (E) UMSCC-11B, (F) NA, and (G) SKOV-1. TriKE added to effector and target cells induced a higher percentages of CD107a-expressing cells compared to controls and also compared to bispecific 16EpCAM. P-values were estimated with one-way-ANOVA and presented with SD. *evaluation against controls; #evaluation 1615EpCAM against EpCAM16.

1615EpCAM TriKE Induces Lytic Degranulation and IFN-γ Expression in Various Cell Lines To determine whether other EpCAM-expressing target cell lines induced similar 1615EpCAM TriKE-mediated NK cell activation as the HT-29 target line, NK cell function was tested on a variety of targets in conjunction with different drug treatments. Breast cancer (FIGS. 10A and 10B), prostate cancer (FIGS. 10C and 10D), head and neck cancer (FIGS. 10E and 10F), and ovarian cancer cell lines (FIG. 10G) were studied. All EpCAM$^+$ carcinoma lines treated with 1615EpCAM (SEQ ID NO:8) induced significantly elevated NK cell degranulation (p<0.001) when compared to various controls including E:T alone, E:T plus IL-15, E:T plus CD16CD133 (an irrelevant BiKE), and E plus IL-12/IL-18. The E:T plus EpCAM16 BiKE also demonstrated marked percentages of cells expressing CD107a and cytotoxic activity since the BiKE possesses cytotoxic activity but lacks the ability to expand. Thus, in all cases, the values observed using the EpCAM16 BiKE were significantly less than values observed for 1615EpCAM (p<0.001).

1615EpCAM TriKE Induces NK Cell Proliferation

Figure 11:
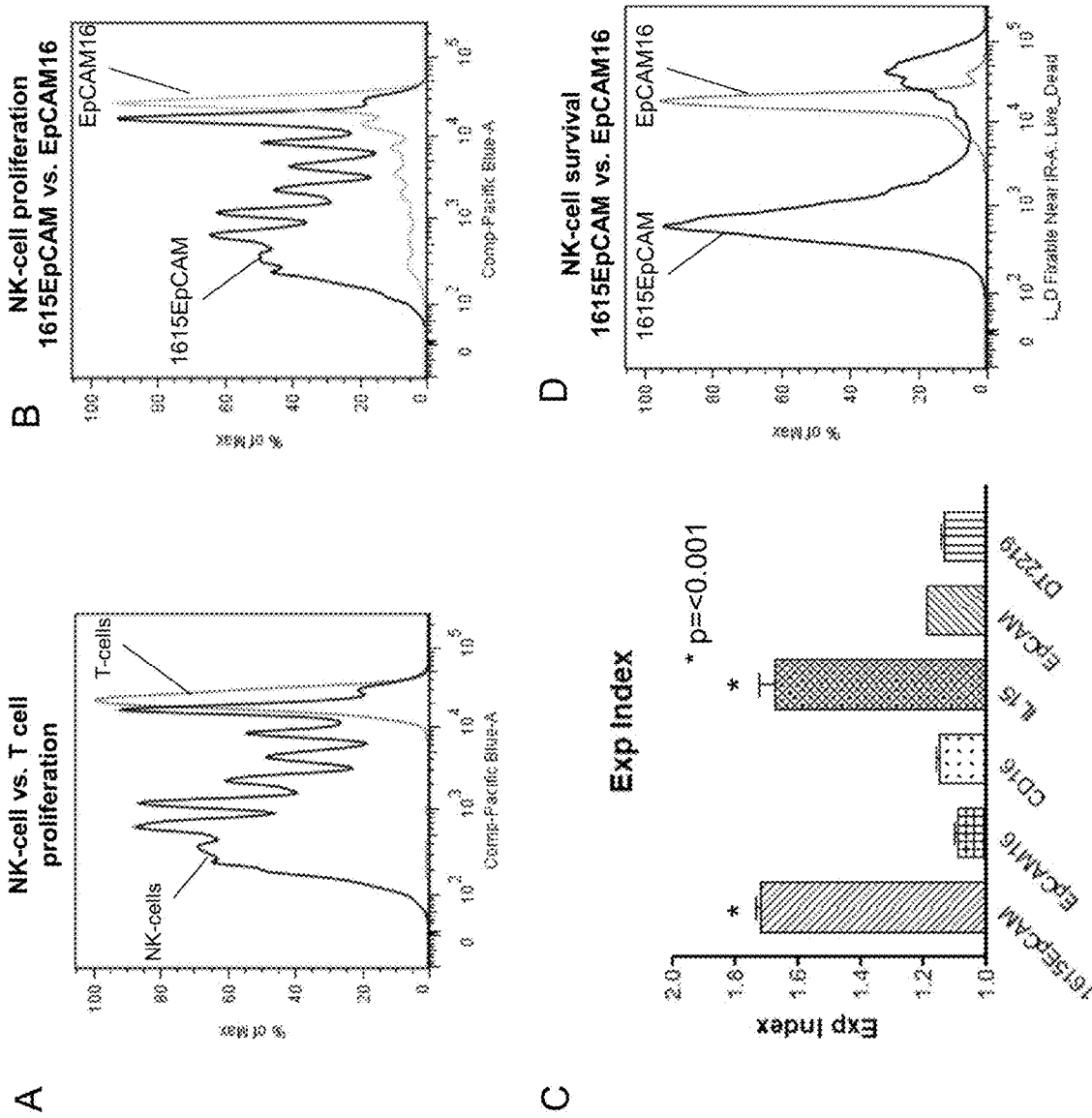
FIG. 11. Proliferation capabilities of 1615EpCAM TriKE. (A) In order to evaluate NK cell expansion, peripheral blood mononuclear cells were treated with 1615EpCAM TriKE or EpCAM16 BiKE. The discrete peaks in the histograms mark successive generations of NK cells after cell division leading in a repetitive slight reduction of florescence intensity. Whereas NK cells show a typical proliferation pattern, T-cells do not. Shown is a representative of five independent experiments. (B) PBMCs cells were co-cultured with the TriKE and the BiKE and NK cell proliferation was evaluated. Shown is a representative of five independent experiments. (C) PBMCs cells were co-cultured with the TriKE, the BiKE, anti-CD16scFv [CD16], Interleukin (IL)-15, anti-EpCAM scFv [EpCAM] and DT2219, a targeted toxin comprised of Diphtheria enterotoxin linked to anti-CD22 and anti-CD19 scFv. Evaluation of the NK cell Expansion Index showed a significantly (p<0.001) enhanced index in the 1615EpCAM construct and with IL-15 alone, marked with *, (n=5). (D) Purified NK cells were exposed to the TriKE and the BiKE. After seven days a reactive dye was used to differentiate alive and dead cells. The reactive dye permeates the impaired membranes of dead cells, resulting in more intense staining (right peak) whereas failure to penetrate the membrane of live cells results in a weaker staining (left peak).

The ability of the 1615EpCAM TriKE (SEQ ID NO:8) to induce proliferation in NK cells is shown in FIG. 11. When donor PBMCs were exposed to the TriKE, NK cells but not T cells showed a proliferation-specific pattern as measured by flow cytometry (FIG. 11A). The results were identical in three of the four donors. When exposed to the TriKE, NK cells undergo a more robust proliferation than T cells. FIG. 11B shows a direct comparison of NK-proliferation induced by the EpCAM16 BiKE and the 1615EpCAM TriKE. The TriKE induces proliferation and expansion, but the BiKE does not. To exclude the possibility of other factors that could induce NK cell proliferation, PBMCs were exposed to TriKE, BiKE, anti-CD16 scFv alone, IL-15 alone, anti-EpCAM scFv alone, or DT2219 (a targeted toxin comprising diphtheria toxin, linked to an anti-CD22 scFv and anti-CD19 scFv). Only TriKE-treated groups and IL-15-treated groups displayed significant NK cell proliferation, as indicted by the changes in expansion index (FIG. 11C), which reflects the fold expansion of the cells. The group stimulated with the TriKE showed higher NK cell survival while the group exposed to the BiKE contained predominantly dead cells, as confirmed with forward/side scatter flow cytometry (FIG. 11D) and trypan blue staining. These data indicate that besides increasing priming of the cells, the IL-15 moiety in the 1615EpCAM TriKE also induces expansion and maintenance of the NK cells.

Figure 12:
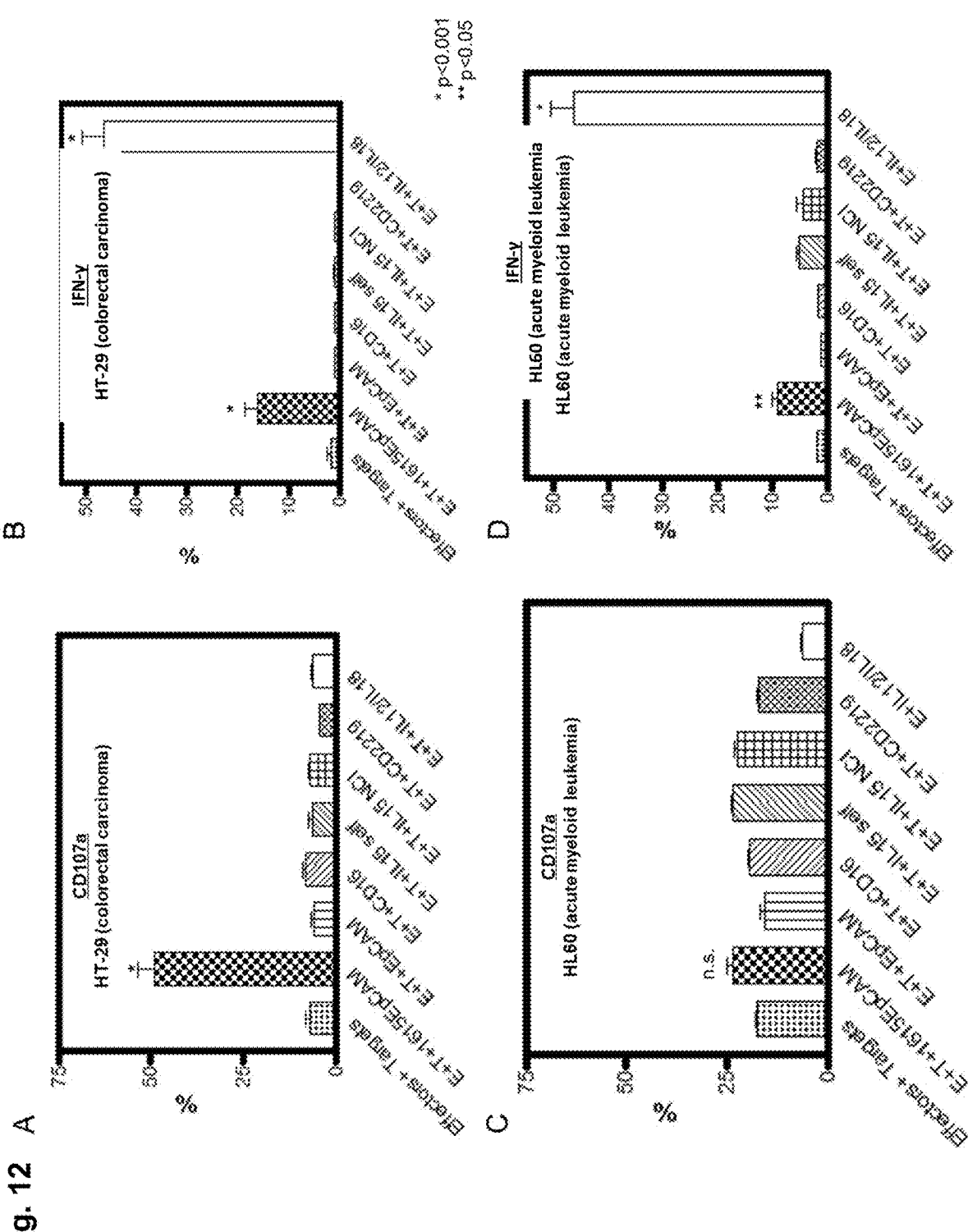
FIG. 12. Lytic degranulation and IFN-γ expression in HT-29 cells. To study NK cell activity, CD107a-expressing cells were evaluated within the gated $CD56^+/CD3^-$ NK cell population. (A) Cells treated with the 1615EpCAM TriKE (SEQ ID NO:8) showed precipitously elevated degranulation of EpCAM-expressing HT-29 target cells, while controls did not. E:T alone, E:T plus anti-EpCAM scFv devoid of 1615, E:T plus anti-CD16 alone, and E:T plus a combination of IL-12 and IL-18 (which does not augment lytic degranulation) did not have any effect. (B) IFN-γproduction from the same $CD56^+/CD3^-$ NK cell population was analyzed. Only 1615EpCAM showed an enhanced percentage of IFN-γ-expressing cells. Values did not approach values seen with the IL12+IL18 combination that is known to stimulate cytokine production at supraphysiologic levels. (C) No CD107a expression cells were observed when NK cells incubated with EpCAM− HL-60 myeloid leukemia cell targets were studied. (D) Only the E:T controls treated with IL12+IL18 showed precipitous expression of IFN-γ.
Figure 14:
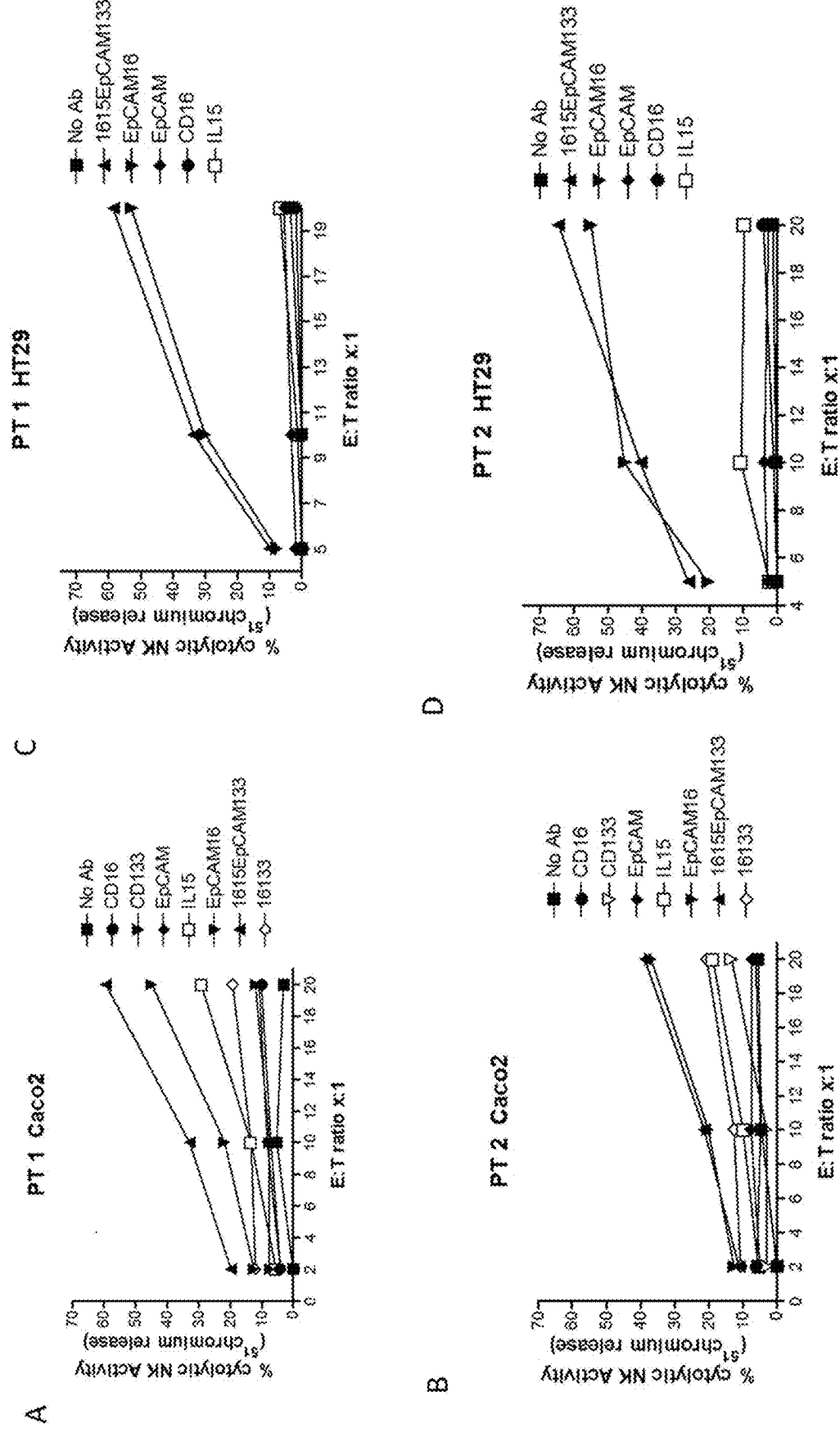
FIG. 14. Activity of 1615EpCAM133. An extra saFv recognizing CD133 expressed on cancer stem cells was added to 1615EpCAM to make 1615EpCAM133 TetraKE. (A) and (B) show the activity of 1615EpCAM133 evaluated with $^{51}Cr$ release assays. Freshly isolated NK cells from two donors (PT 1 and PT 2) were added to the human colorectal carcinoma cell line Caco-2 ($CD133^+$, $EpCAM^+$). Cells were co-cultured with targets at noted effector to target (E:T) ratios for four hours and $^{51}$chromium release was then evaluated. In (C) and (D), NK cells from two donors were exposed to human colorectal carcinoma cell line HT-29 ($EpCAM^+$, $CD133^-$) and $^{51}$chromium release was measured in the same manner as described above.

1615EpCAM TriKE Induces Lytic Degranulation and IFN-γ Expression Against HT-29 Target Cells To study lytic degranulation as a parameter of NK cell activity, CD107a expression was measured within a CD56$^+$/CD3$^-$ NK cell population incubated with EpCAM-expressing HT-29 targets. Cells incubated with EpCAM16 BiKE showed elevated CD107a expression when compared with effectors alone, effectors plus targets without drug, or effectors plus targets with anti-EpCAM scFv. The 1615EpCAM TriKE induced significantly more CD107a expression than the BiKE (FIG. 12A). The 1615EpCAM also induced significantly elevated degranulation when compared to an extensive panel of controls (including E:T alone, E:T plus anti-EpCAM scFv devoid of 1615, E:T plus anti-CD16 ScFv alone, CD2219, and E:T plus a combination of IL-12 and IL-18) that did not have any effect. Two different sources of stand-alone IL-15, when combined with E:T, also failed to enhance lytic degranulation (IL-15 self, linker protein; IL-15 NCI, NCI derived). IFN-γ production also was enhanced in the 1615EpCAM TriKE-treated NK cells when compared to NK cells treated with the BiKE alone or the BiKE plus IL-15, indicating the biological ability of the IL-15 moiety within the TriKE to induce priming for cytokine secretion (FIG. 12B). As before, an extensive panel of controls was tested against the TriKE, in which only IL-12/IL-18 supraphysiologic stimulation outperformed the TriKE.

In FIG. 12C, no CD107a expression was observed when NK cells were incubated with control EpCAM$^-$ HL-60 myeloid leukemia cells. No elevation of IFN-γ expression was observed as expected with negative control HL-60 targets, except for control cells treated with IL-12/IL-18, showing the IFN-γ assay was working (FIG. 1D).

1615EpCAM133 Induces Chromium-51 Release

The design of the engineered tetraspecific 1615EpCAM133 (SEQ ID NO:9) is shown in FIG. 13. 1615EpCAM133 activity was evaluated with chromium release assays in order to measure NK cell killing. The assay was performed using Caco-2 (CD133$^+$, EpCAM$^-$) and HT-29 (CD133$^-$, EpCAM$^+$) targets and freshly isolated NK cells of two donors (PT1 and PT2) for each cancer cell line, with no antibody (No Ab), anti-CD16 scFv, anti-CD133 scFv, anti-EpCAM scFv, IL-15 alone, and the EpCAM16 BiKE run as controls. In all donors and in both cancer cell types, 1615EpCAM133 showed superior killing at increasing E:T ratios (FIG. 14A-D). Controls showed minimal activity. These data show that targeting two different moieties on the tumor cell is possible. In this case, one is a broader epithelial marker target (EpCAM) and the other is the more specific anti-cancer stem cell target CD133.

1615EpCAM133 Induces NK Cell Proliferation

Figure 15:
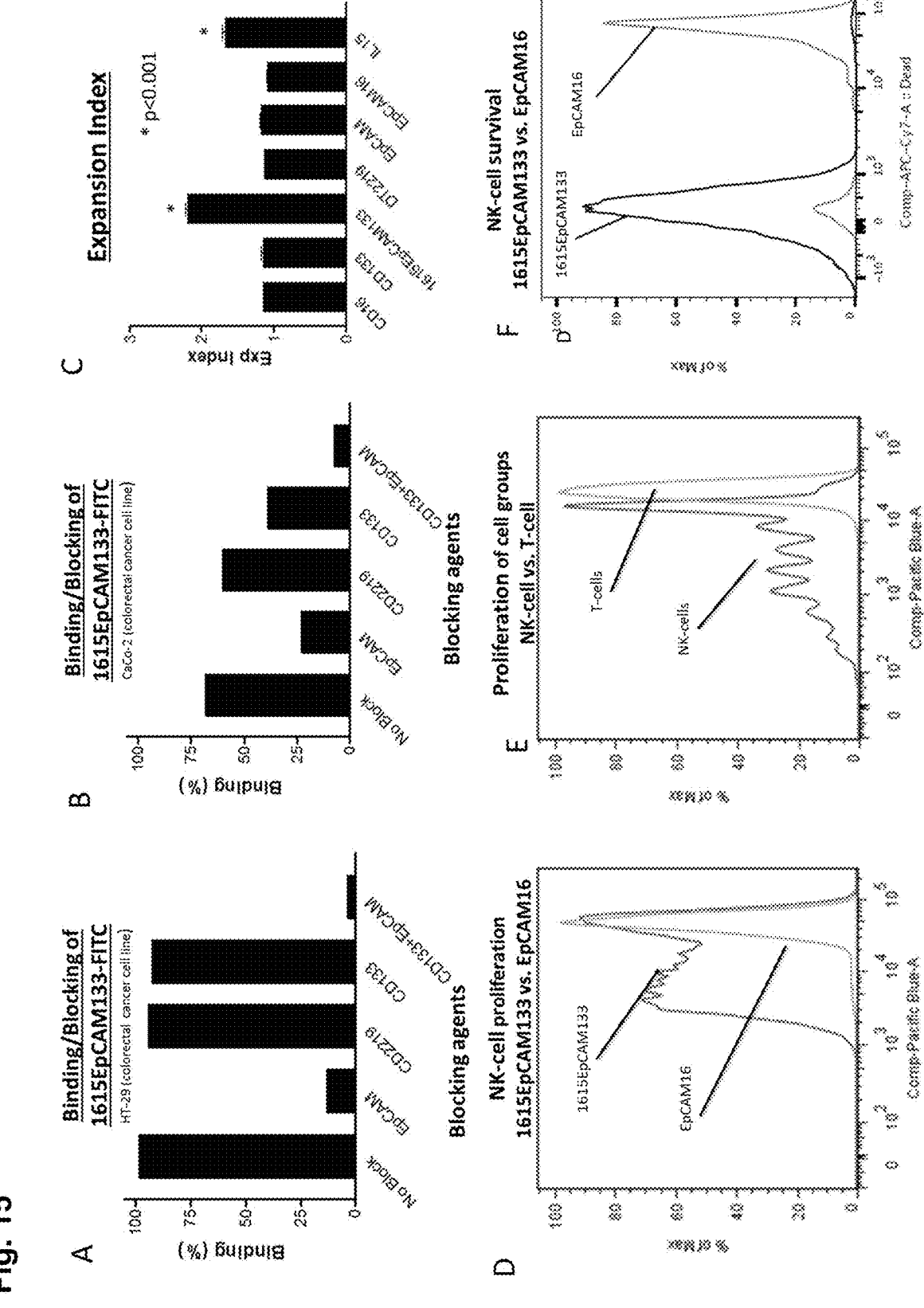
FIG. 15. Just like 1615EpCAM, 1615EpCAM133 shows enhanced expansion due to the presence of IL-15. (A) Binding assays against HT-29 cells and (B) Caco-2 cells were performed using FITC-labeled 1615EpCAM133 TetraKE (200 nM) competed with excess unlabeled noted scFvs (1000 nM). Experiments were repeated with 200 nM of 1615EpCAM133 and a lower block with 500 nM of the scFv. Results were reproducible. (C) Purified NK cells were stained with CELLTRACE (Thermo Fisher Scientific, Waltham, Mass.) to measure proliferation and co-cultured with an anti-CD16 scFv [CD16], anti-CD133 scFv [CD133], 1615EpCAM133 TetraKE, DT2219 (mutated diphtheria toxin linked to an anti-CD22 and an anti-CD19 scFv), anti-EpCAM scFv [EpCAM], EpCAM16 BiKE, or IL-15 [IL15] for seven days (n=5). Graph shows pooled data of the expansion index for each of the groups. (D) Representative histogram of PBMCs stained with CELLTRACE dye and co-cultured with 30 nM of 1615EpCAM133 TetraKE or EpCAM16 BiKE for seven days. (E) Representative histogram comparing proliferation on $CD56^+CD3^-$ NK cells with $CD56^-CD3^+$ T cells. (F) Representative histogram illustrating survival (by means of Live Dead dye exclusion) of purified NK cells exposed to the 1615EpCAM133 TetraKE or EpCAM16 BiKE for seven days. Dead cells display inclusion of the dye (high peak) while live cells exclude it (low peak). P-values were estimated with one-way-ANOVA and presented with standard deviation.

The ability of 1615EpCAM133 to selectively bind is shown in FIGS. 15A and 15B. The ability of the IL-15 moiety within the molecule to induce proliferation and survival is shown in FIG. 15C-F. Purified NK cells were exposed to an anti-CD16 scFv, anti-CD133 scFv, 1615EpCAM133, DT2219 (mutated diphtheria toxin linked to an anti-CD22 and an anti-CD19 scFv), anti-EpCAM scFv, EpCAM16 BiKE, or IL-15 alone (NCI). Expansion index, which determines overall expansion of the culture, showed significantly enhanced expansion in the 1615EpCAM133 and in the IL-15 groups (p<0.001), (FIG. 15C). To compare the ability of the IL-15 linker to induce proliferation, PBMCs or purified NK cells were cultured after staining with a reactive dye and exposed to the EpCAM16 BiKE or the 1615EpCAM133 tetraspecific molecule. After incubation, flow cytometry was performed on gated CD56$^+$CD3$^-$ cells to evaluate NK cells and on CD56$^-$CD3$^+$ cells to evaluate T-cells. In FIG. 15D, only NK cells treated with 1615EpCAM133 showed substantial proliferation. Treatment with the EpCAM16 BiKE did not. The ability to induce specific proliferation to NK cell is shown in FIG. 15E; T cells did not proliferate after exposure to 1615EpCAM133.

To study the ability of 1615EpCAM133 to enhance survival of NK cells, purified NK cells were co-cultured for seven days and treated with1615EpCAM133 or EpCAM16 BiKE. After live-dead staining via flow cytometry, a much higher percentages of live NK cells were seen in the 1615EpCAM133 group (FIG. 15F).

1615133 induces Chromium-51 Release

Figure 16:
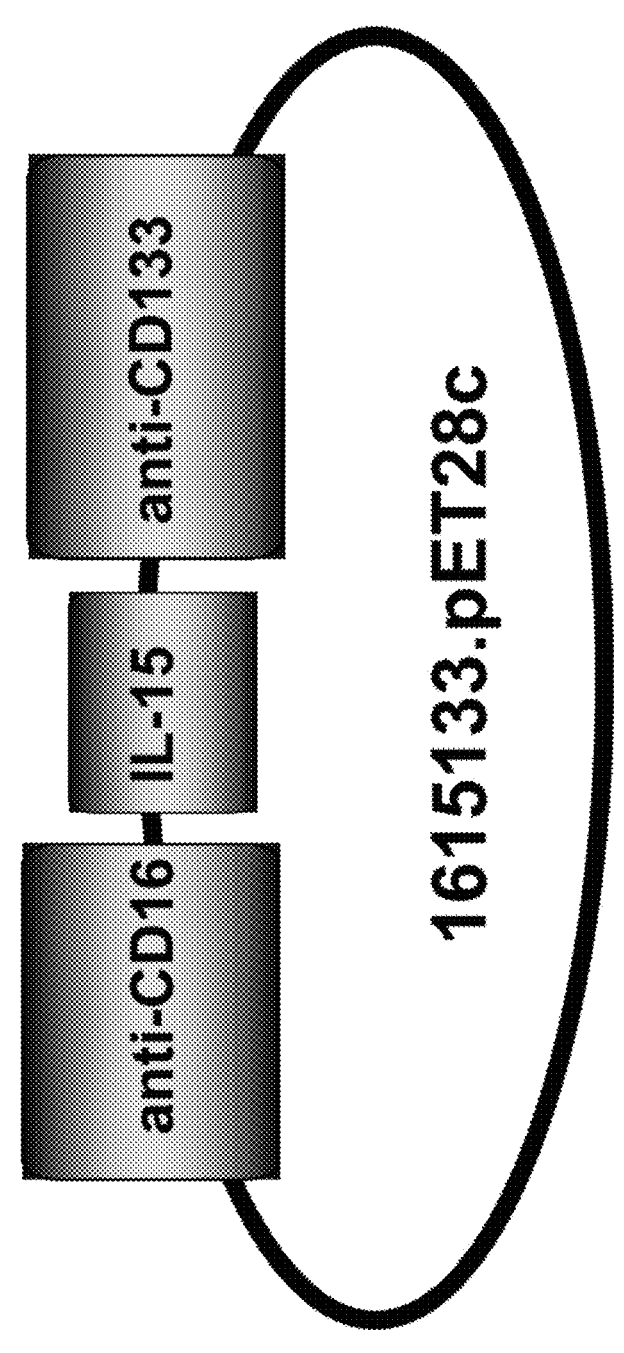
FIG. 16. Schematic of placement of the coding regions for 1615133 (SEQ ID NO:10) in the pET expression vector. The hybrid polynucleotide encoding 1615133 was synthesized using dNA shuffling and DNA ligation techniques. The fully assembled polynucleotide has, from the 5' end to the 3' end, a NcoI restriction site; an ATG start codon; coding regions encoding anti-human CD16 scFv, a 20 amino acid segment (PSGQAGAAASESLFVSNHAY; SEQ ID NO:3), mutated human IL-15, a seven amino acid linker (EASGGPE; SEQ ID NO:4), and anti-CD133 scFv; and a NotI restriction site. The resultant 1884 base pair NcoI/NotI fragment polynucleotide was spliced into the pET28c expression vector under control of an isopropyl-β-D-thiogalactopyranoside (IPTG) inducible T7 promoter.
Figure 17:
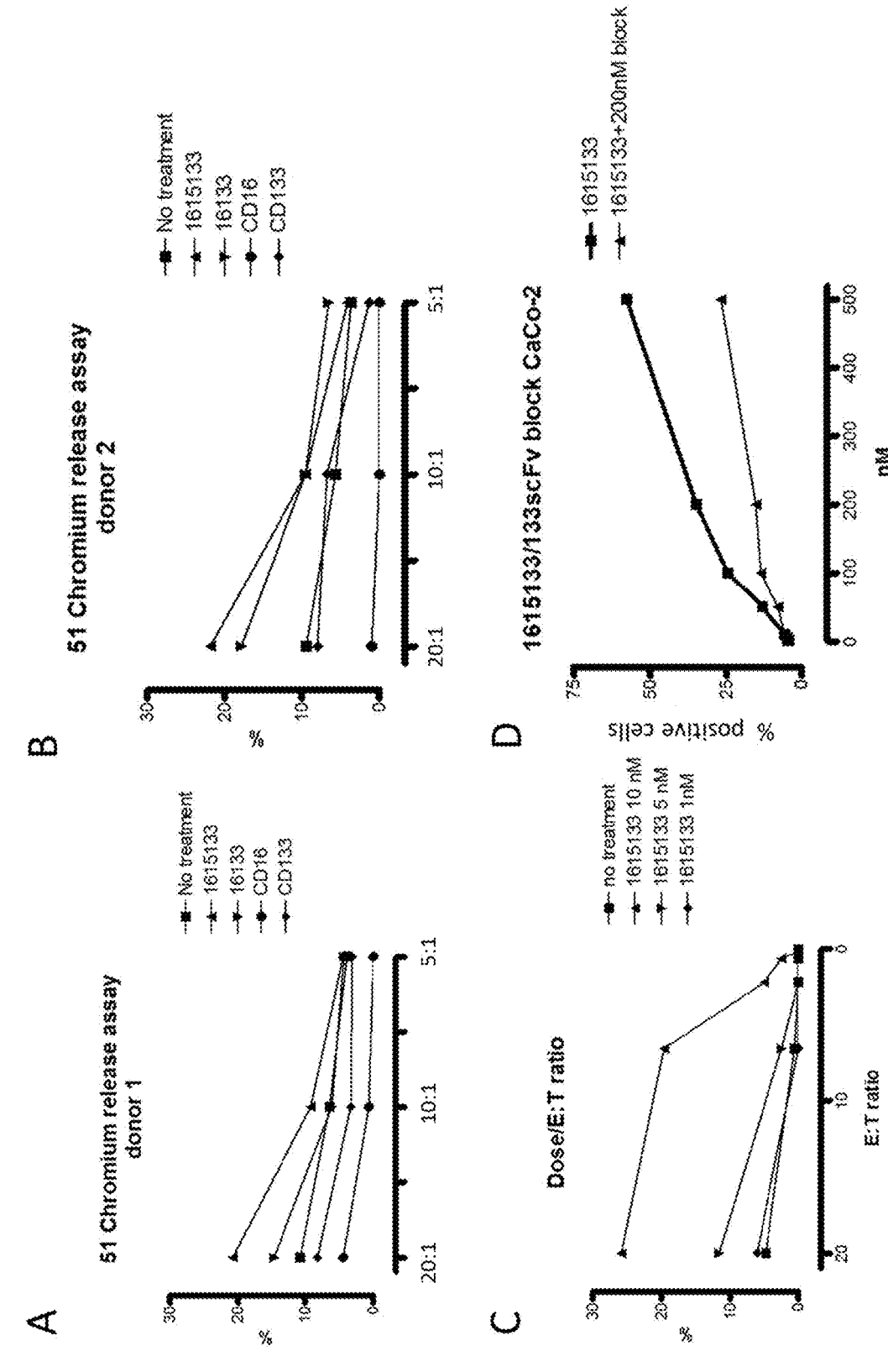
FIG. 17. [51]Chromium release and binding of TriKE 1615133. (A, B) For evaluation of activity, [51] Chromium release assays using two donors were performed. 1615133 TriKE, 16133 BiKE, anti-CD16 scFv [CD16], or anti-CD133 scFv [CD133] was co-cultured with CD133[+] Caco-2 cells and PBMCs at labeled E:T ratios. (C) PBMCs and Caco-2 cells were exposed to different TriKE concentrations (1 nM, 5 nM, 10 nM) and titered in their E:T ratio (20:1, 6.6:1, 2,2:1, 0.75:1, 0.23:1, 0.08:1). (D) FITC-labeled 1615133 TriKE was incubated at labeled concentrations with Caco-2 cells. In the same experiment, the same amount of FITC labeled 1615133 was added with 200 nM of a monomeric CD133 scFv for blocking.

The design of the engineered 1615133 is shown in FIG. 16. In order to evaluate functional activity of the 1615133 TriKE, standard $^{51}$Chromium release assays were performed. To determine the effect of incorporating IL-15 into the 16133 scaffold, the cytotoxicity was evaluated using NK cells of two separate donors and Caco-2 tumor targets at different E:T ratios (20:1, 10:1, and 5:1) and compared activity between 1615133 TriKE, 16133 BiKE, anti-CD16 scFv, anti-CD133 scFv, and no drug treatment (FIGS. 17A and 17B). Killing of Caco-2 targets was elevated in the TriKE compared to controls. Dose dependent titration of the 1615133 TriKE (1 nM, 5 nM, and 10 nM) with a broader spectrum of E:T ratios (20:1, 6.6:1, 2.2:1, 0.7:1, 0.23:1, and 0.08:1) showed highest impact of the drug activity at higher doses (FIG. 17C). To evaluate specificity of binding, flow-cytometry-based fluorescence intensity was measured after incubating Caco-2 cells with FITC-labeled 1615133 TriKE in different concentrations (1 nM, 5 nM, 10 nM, 50 nM, 100 nM, 200 nM, or 500 nM). When an unlabeled anti-CD133 scFv (200 nM) was added along with the 1615133 TriKE, binding was potently reduced (FIG. 17D), indicating that the 1615133 TriKE binds to target cells specifically through interaction with CD133. Together, these data indicated that the ADCC mediated by the TriKE is antigen directed.

1615133 Induces NK Cell Proliferation

Figure 18:
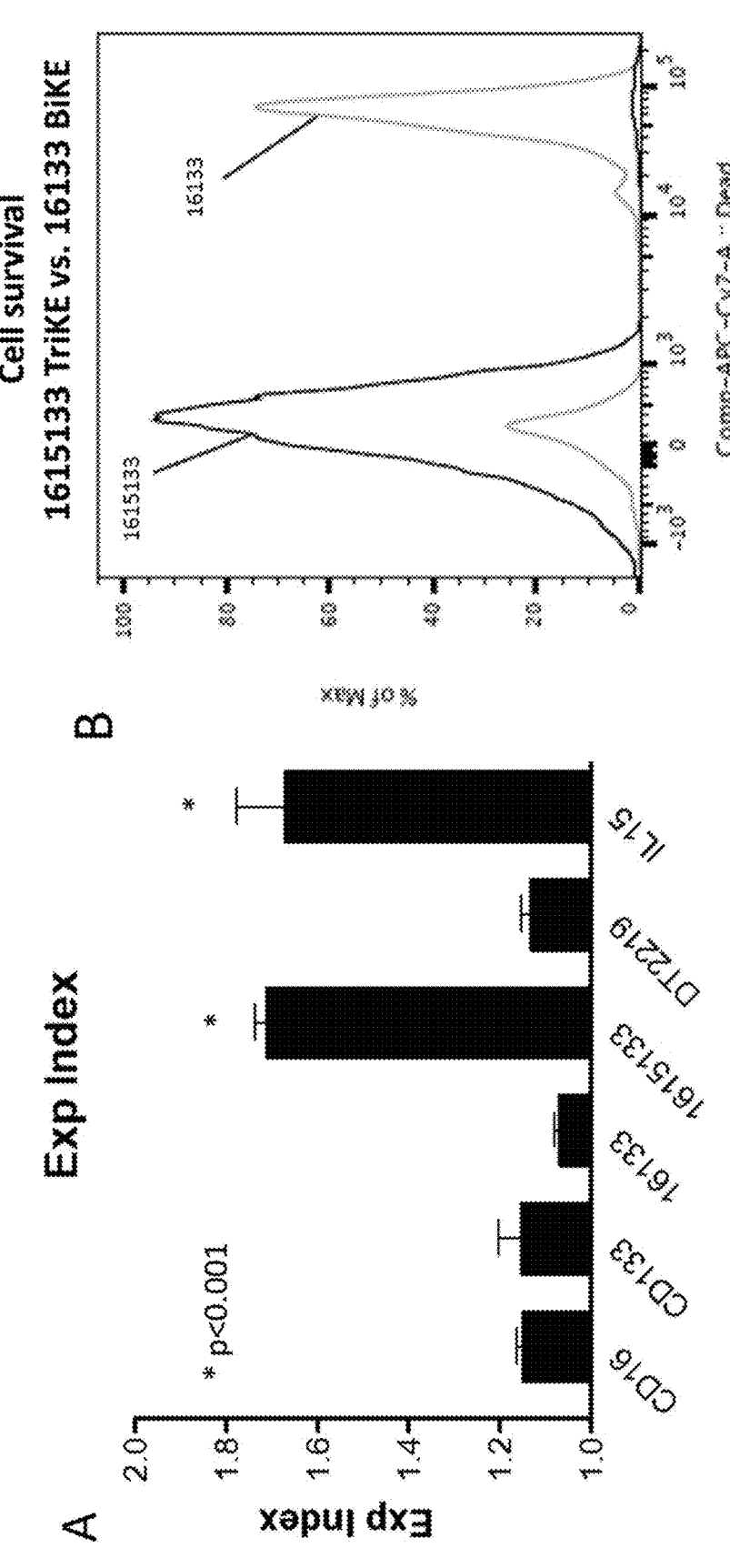
FIG. 18. Expansion and survival, (A) Purified NK cells were exposed to anti-CD16 scFv (CD16), anti-CD133 scFv (CD133), 16133 BiKE, 1615133 TriKE, DT2219 (a targeted. toxin consisting of an anti-CD22 and anti-CD19 scFv linked to a diphtheria toxin), or NCI-derived IL-15. Only the TriKE and IL-15 significantly increased proliferation (n=5). Graph shows pooled data of the expansion index, calculated in Flowjo software, for each of the groups. (B) Purified NK cells were exposed to 16151:33 TriKE and 16133 BiKE and incubated for seven days. The representative histogram illustrates a higher amount of live cells with the TriKE compared to the BiKE construct without the IL-15 moiety. Significance was estimated with one-way-ANOVA and presented with standard deviation.

The proliferation induced by 1615133 (SEQ ID NO:10) was measured by CELLTRACE dye dilution in the viable NK and T cell populations. When donor PBMCs were exposed to 1615133 TriKE or 16133 BiKE, only the TriKE group induced proliferation (FIG. 18A). Importantly, comparison to other control agents including anti-CD16 scFv, anti-CD133 scFv, DT2219 (a targeted toxin consisting of an anti-CD22 and anti-CD19 scFv linked to a diphtheria toxin), and NCI derived IL-15 showed that only the 1615133 TriKE and NCI IL-15 induced proliferation. To show the potential of 1615133 TriKE to induce prolonged survival, purified NK cells were incubated for seven days with 1615133 or 16133 BiKE. A reactive dye was used to quantify cell death in the different treatment groups. The TriKE group showed a greater amount of live cells, which do not incorporate the reactive dye, compared to the BiKE (FIG. 18B). Together, the results indicate that the IL-15 present in the 1615133 TriKE induces NK cell proliferation and prolonged their survival.

Figure 19:
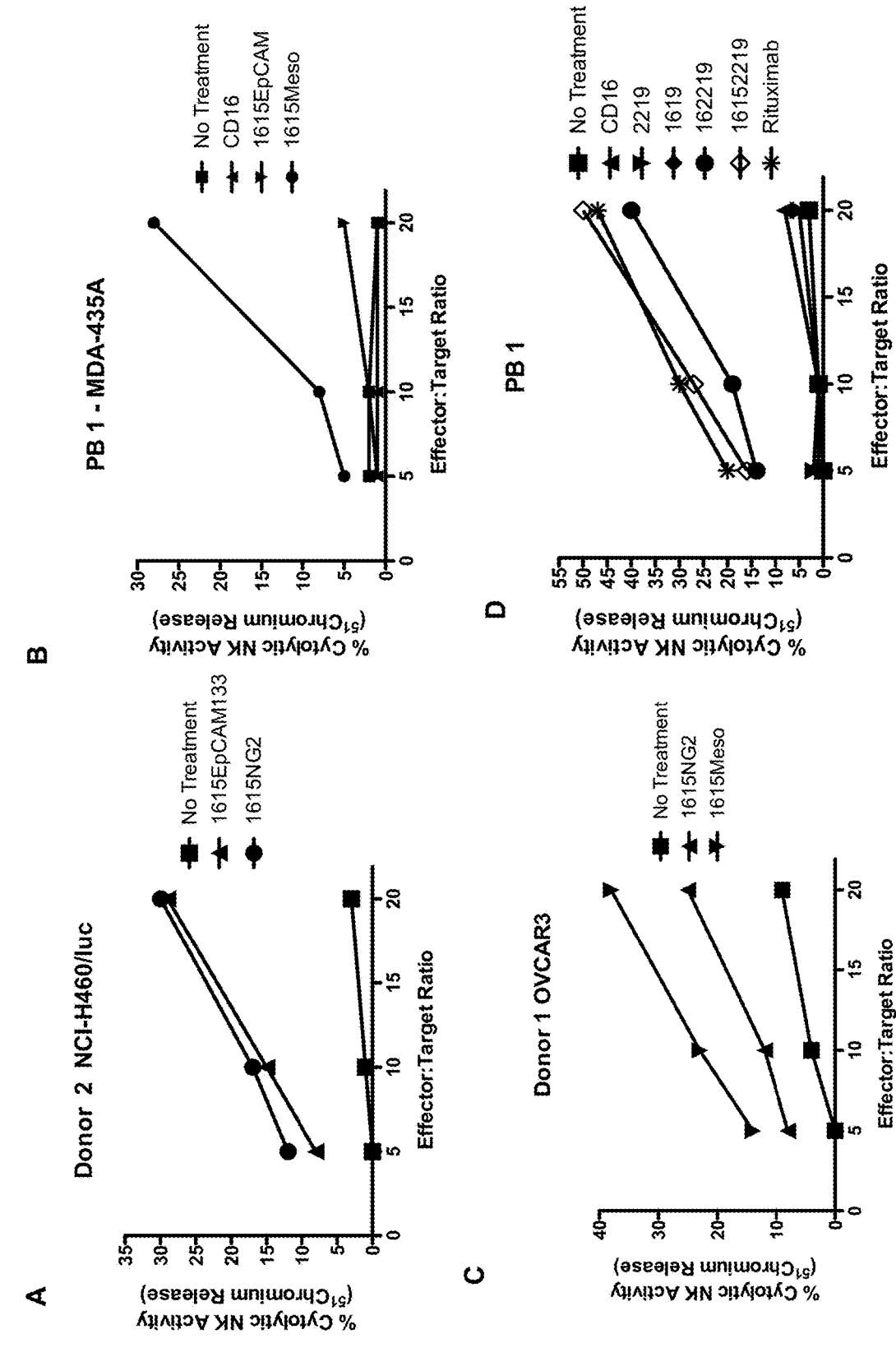
FIG. 19. [51]Chromium release assays were performed with several different new TriKEs to show that any scFv that targets cancer cells can be made into functional TriKEs. (A) EpCAM+CD133+NG2+ non-small cell lung cancer NCI-H460 cells plus NK cells were incubated with 1615EPCAM133 TriKE or 1615NG2 TriKE (neuron glial antigen 2 or CSPG4). Both 1615NG2 and 1615EpCAM133 had activity at several different E:T ratios (20:1, 10:1, and 5:1). (B) Mesothelin+EpCAM−CD133−NG2 MDA-435A melanoma cells were incubated with 1615EPCAM TriKE (SEQ NO:8) or the 1615Meso TriKE (SEQ ID NO:11) TriKE. Only 1615Meso had activity. (C) Mesothelin+NG2+ ovarian cancer cells (Ovcar3 cells) were incubated with 1615NG2 TriKE or 1615SS1 TriKE. 1615Meso and 1615NG2 had activity. (D) Raji cells were cultured with NK cells and studied in $^{51}$Cr release assays. TriKE 16152219 (SEQ ID NO:12) simultaneously targets the B cell markers CD19 and CD22. Only 16152219, 162219, and Rituximab killed the CD22+CD19+ targets. The controls did not.

TriKEs Generally Induce Chromium-51 Release $^{51}$Chromium release assays were performed with several different TriKEs to show that any scFv that targets cancer cells can be incorporated into a functional Non-small cell lung cancer cells (NCI-H460) cells were incubated with the 1615EPCAM133 TriKE (SEQ ID NO:9) or the 1615NG2 TriKE. Both 1615NG2 and 1615EpCAM133 had activity at several different E:T ratios (20:1, 10:1, and 5:1). FIG. 19B shows melanoma cells were incubated with the 1615EPCAM133 Mesothelin+EpCAM–NG2 MDA-435A melanoma cells were incubated with 1615EPCAM TriKE, or the 1615Meso TriKE (SEQ ID NO:11). Only 1615Meso had activity. Ovarian cancer cells (Ovcar3 cells) were incubated with the 1615NG2 TriKE or the 1615Meso TriKE. Both TriKEs induced NK cytolytic activity. Also, an anti-leukemic TriKE was made recognizing the leukemia markers CD19 and CD22, 16152219 TriKE was tested on CD22+ CD19+ Raji cells and killed them very well (as well as rituximab). Together, these data show that any scFv can be inserted into the generalized TriKE structural platform of 1615X and the resulting TriKE can direct NK cells to respond to the scFv target and expand. Additional exemplary TriKE molecules are listed in Table 3.

TABLE 3

Exemplary TriKE molecules

| TriKE molecule | Target(s) | ADCC* | Expansion** | Activation*** |
|---|---|---|---|---|
| 161533 | CD33 | + | + | + |
| 1615EpCAM | EpCAM | + | + | + |
| 1615EpCAM133 | EpCAM/CD133 | +/+ | +/+ | +/+ |
| 1615133 | CD133 | + | + | + |
| 1615NG2 | NG2 | + | + | + |
| 1615Meso | mesothelin | + | + | + |
| 1615ROR-1 | ROR-1 | + | + | + |
| 16a1538 | CD38 | + | + | + |
| 1615IGF-1 | IGF1 | + | + | + |
| 1615Her2 | Her2/neu | + | + | + |
| 16152219 | CD22/CD19 | +/+ | +/+ | +/+ |
| Llama161533 | CD33 | + | + | + |
| 1615HIV | HIV | + | + | + |

*ADCC or cytotoxic activity enhanced over 30% by TriKE platform
**Expansion: TriKE enhances of NK cells, BiKE does not.
***Activation: TriKE enhances the production of various anti-cancer cytokines including INFγ and TNFα.

Several TriKEs have been produced and tested in an identical manner, but target different cancer markers. CD33 or Siglec-3 (sialic acid binding Ig-like lectin 3, SIGLEC3, SIGLEC-3, gp67, p6'7) is a transmembrane receptor expressed on cells of myeloid lineage. It is usually considered myeloid-specific. EpCAM, epithelial cell adhesion molecule, is a transmembrane glycoprotein mediating $Ca^{2+}$-independent homotypic cell-cell adhesion in epithelia. CD133, also known as prominin-1, is a glycoprotein that in humans is encoded by the PROM1 gene and a member of pentaspan transmembrane glycoproteins (5-transmembrane, 5-TM), which specifically localize to cellular protrusions. NG2 is chondroitin sulfate proteoglycan 4, also known as melanoma-associated chondroitin sulfate proteoglycan (MCSP) or neuron-glial antigen 2 (NG2). It represents an integral membrane chondroitin sulfate proteoglycan expressed by human malignant melanoma cells. Mesothelin is a 40 kDa protein present on normal mesothelial cells and overexpressed in several human tumors, including mesothelioma and ovarian and pancreatic adenocarcinoma. ROR-1 is a receptor tyrosine kinase that modulates neurite growth. It is a type I membrane protein belonging to the ROR subfamily of cell surface receptors and is currently under investigation for its role in the metastasis of cancer cells. HER2 is a member of the human epidermal growth factor receptor (HER/EGFR/ERBB) family. CD38 (cluster of differentiation 38), also known as cyclic ADP ribose hydrolase, is a glycoprotein found on the surface of many immune cells. IGF-1 is insulin-like growth factor 1 (IGF-1), also called somatomedin C. IGF-1 is a protein that in humans is encoded by the IGF1 gene and associated with breast cancer. The human immunodeficiency virus (HIV) is a lentivirus (a subgroup of retrovirus) that causes HIV infection and over time acquired immunodeficiency syndrome (AIDS) and Kaposi Sarcoma.

CD3–IL2–EpCAM TriKE Selectively Boosts Proliferation of T Cells

Figure 20:
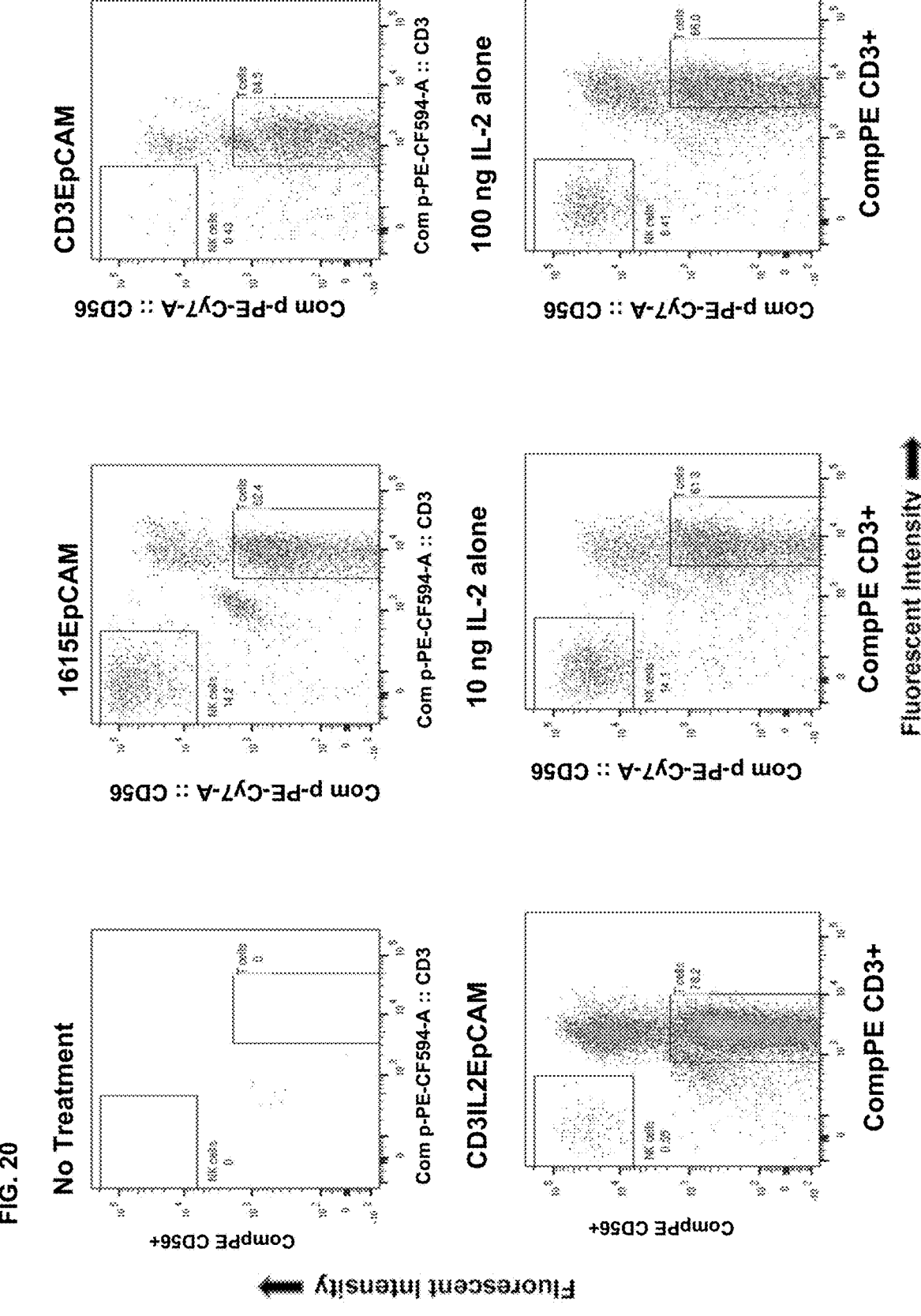
FIG. 20. TriKEs have been synthesized that work with IL-2 and stimulate the expansion of T cells rather than NK cells. in order to determine if other cytokines work in place of IL-15, CD3−IL−2−EpCAM (SEQ ID NO:13) was constructed using the same flanking sequences on either side of IL-2 that were used on either side of the IL-15 domain in the NK-activating TriKE constructs. PBMCs were CELL- TRACE (Thermo Fisher Scientific, Waltham, Mass.) labeled and placed in culture with no treatment (neg control), 1615EpCAM TriKE (pos control), CD3EpCAM BiTE, CD3−IL−2−EpCAM TriKE, 10 ng/ml IL-2, or 100 ng/ml IL-2. The CD3−IL2−EpCAM TriKE stimulated CD3+ T cells much greater than 1.615EpCAM TriKE, CD3EpCAM BiTE, or IL-2 at either 10 ng/ml or 100 ng/ml.

TriKEs have been synthesized that work with IL-2 in place of IL-15 with the same flanking sequences. These stimulate the expansion of I cells rather than NK cells, The T-cell-directed TriKE CD3–IL–2–EpCAM (SEQ ID NO:13) was synthesized and tested for its ability to stimulate T cells rather than NK cells (FIG. 20). IL-2 is known to be a better stimulant of T cell proliferation than IL-15. PBMCs were CELLTRACE (Thermo Fisher Scientific, Waltham, Mass.) labeled and placed in culture. The histogram shows that CD3–IL–2–EpCAM drove robust proliferation of T cells, but not NK cells. CD3–IL–2–EpCAM showed better stimulation than any other agent tested including 1615EpCAM TriKE (pos control), CD3EpCAM BiTE, CD3–IL–2–EpCAM, IL-2, or no treatment. These data indicate that IL-2 works in the same manner as IL-15 when used as a cross-linker on this platform.

Thus, this disclosure describes the design and use of a tri-specific killer engager (TriKE) capable of creating immunologic synapses between NK cells and a target. A CD33$^+$ myeloid target was used as a model target for a model TriKE that included an anti-CD16 antibody as a model NK engaging domain, an anti-CD33 antibody as a model targeting domain that targeted the CD33$^+$ myeloid target, a model IL-15-based NK activating domain, and flanking sequences on either side of the NK activating domain linking the NK activating domain to the remaining domains. The flanking sequences are PSGQAGAAASESLFVSNHAY (SEQ ID NO:3) upstream of the NK activating domain and EASGGPE (SEQ ID NO:4) downstream of the NK activating domain. The flanking sequences influence the functional activity of the TriKE molecules and represents an entirely unexpected finding.

One exemplary model TriKE (161533, SEQ ID NO:1) exhibited increased function to a comparable bi-specific killer engager (1633 BiKE, SEQ ID NO:2) in cytotoxicity, CD107a degranulation, and cytokine production assays of NK-cell-mediated responses against HL-60 targets. The activity of the exemplary model TriKE in a physiologic context was evaluated using patient NK cells collected early after allogeneic stem cell transplantation, a context where NK cell function is defective. Compared to the 1633 BiKE, the TriKE containing an IL-15 NK activating domain induced NK cell but not T cell survival and proliferation. The exemplary model TriKE molecule also induced the hyporesponsive patient NK cells to mediate potent responses against primary acute myeloid leukemia targets. Lastly, the exemplary model TriKE molecule exhibited superior anti-tumor activity compared to the comparable BiKE, and induced in vivo persistence and survival of human NK cells for at least three weeks in a xenogeneic model using HL-60-Luc and human NK cells.

The data presented herein establish the utility of the exemplary TriKE molecule and provides the foundation for the design and construction of alternative TriKE molecules. As described in detail above, a TriKE molecule may be designed using any suitable NK engaging domain and/or any suitable targeting domain.

The exemplary 161533 TriKE (SEQ ID NO:1) was used as a model because CD16 is expressed on the surface of NK cells. Thus, an scFv that selectively binds to NK cells can be used as an NK cell engaging domain. CD33 is expressed on AML, acute myeloid leukemia cells (a common form of adult leukemia), but is also found on myelodysplastic cells that may signal a predisposition to AML. Thus, and anti-CD33 scFv can be used as a targeting domain.

In an alternative embodiment, however, an anti-EpCAM antibody can be used in the targeting domain of a TriKE. EpCAM is an epithelial cancer marker expressed on most types of carcinoma including, for example, lung, breast, colorectal, prostate, pancreatic, GI, renal, and ovarian cancer. Data showing that a TriKE (1615EpCAM, SEQ ID NO:8) that includes an anti-EpCAM scFv enhances killing of colorectal cancer cells indicates that any suitable targeting domain (e.g., any suitable scFv) can be included in a TriKE based on the anti-CD16/IL15 platform with similar success. The 1615EpCAM TriKE includes an anti-CD16 scFv as the NK engaging domain, and IL-15 NK activating domain, and the anti-EpCAM scFv as the targeting domain.

In yet another alternative embodiment, CD38 is known to be expressed on multiple myeloma cells. Data showing that a TriKE (16a1538, SEQ ID NO:16) that includes an anti-CD38 scFv enhances killing of multiple myeloma cells in vitro further indicates the general modularity of the TriKE platform. The 16a1538 TriKE includes an anti-CD16a scFv as the NK engaging domain, an IL-15 NK activating domain, and an anti-CD38 scFv as the targeting domain. Finally, one can create a TetraKE (tetramer) by designing the molecule to include a second targeting domain. For example, one can design a TetraKE to include an anti-CD133 scFv (SEQ ID NO:17) to, for example, the 1615EpCAM TriKE (SEQ ID NO:8) to form an exemplary TetraKE (1615EpCAM133, SEQ ID NO:9). CD133 is an established marker on cancer stem cells. Cancer stem cells represent the small population of stem cells in a tumor that are responsible for tumor initiation, renewal, and chemotherapy resistance.

In some embodiments this disclosure describes an immune engager that simultaneously mediates ADCC and provides a self-sustaining signal inducing NK effector cell expansion and maintenance. Although a BiKE that includes anti-CD16 scFv spliced to anti-EpCAM scFv promoted formation of an immune synapse between NK effector cells and EpCAM-expressing carcinoma cells that resulted in cytotoxic degranulation culminating in ADCC of the target cells, both cytotoxic activity and NK longevity can benefit by the addition of a costimulatory signal that enhances effector cell expansion directly at the site of immune engagement. In some embodiments, this costimulatory signal is provided by adding an agent well-suited for expanding NK cells. For example, to facilitate selective NK expansion, IL-15 was cross-linked into EpCAM16 BiKE. As shown in Example 2, the molecular addition of IL-15 to an immune engager can mediated NK proliferation, can produce sustained ADCC activity, and can improve lytic degranulation and cytokine secretion of the immune engager.

In some embodiments, the NK cell engager can involve the use of a humanized CD16 engager derived from an animal nanobody. While an scFv has a heavy variable chain component and a light variable chain component joined by a linker, a nanobody consists of a single monomeric variable chain—i.e., a variable heavy chin or a variable light chain—that is capable of specifically engaging a target. A nanobody may be derived from an antibody of any suitable animal such as, for example, a camelid (e.g., a llama or camel) or a cartilaginous fish. A nanobody can provide superior physical stability, an ability to bind deep grooves, and increased production yields compared to larger antibody fragments.

Figure 22C:
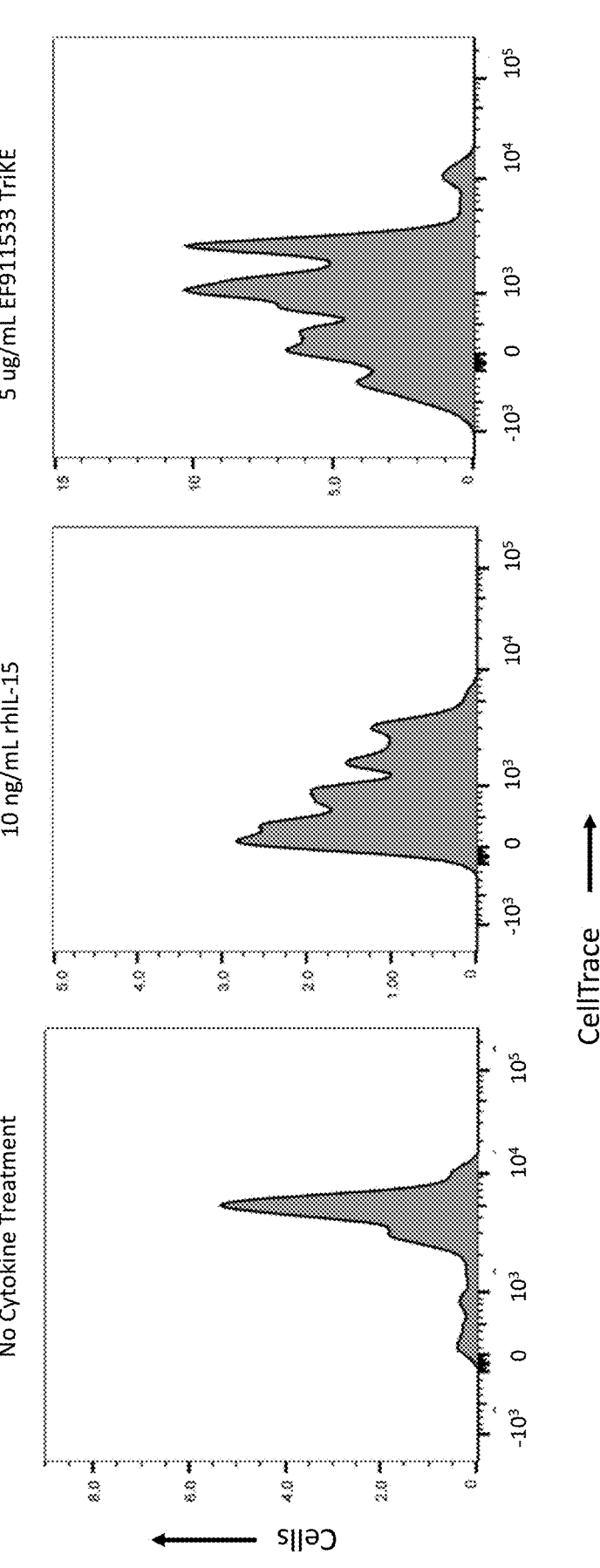
FIG. 22C. The llama161533 TriKE (SEQ ID NO:14) is capable of expanding NK cells.

In one exemplary embodiment, a nanobody-based NK engager molecule can involve a humanized CD16 nanobody derived from a published llama nanobody (GeneBank sequence EF561291; Behar et al., 2008. *Protein Eng Des Sel.* 21(1):1-10), termed EF91. Llama EF91 was initially constructed into a BiKE containing CD19 to test the ability of this CD16 engager to drive NK cell activation. It showed functionality similar to rituximab-mediated killing in a chromium release assay with Raji targets (FIG. 22A). Upon confirming functionality of the molecule, the CDRs were cloned into a humanized camelid scaffold (Vincke et al., 2009. *J Biol Chem.* 284(5):3273-3284) to humanize the CD16 engager, now termed HuEF91. The binding of HuEF91 is shown in FIG. 22B and is equivalent to binding observed using a standard CD16 scFv, indicating that incorporating the llama nanobody variable heavy chain into the humanized backbone has not hindered the specificity of the molecule. The use HuEF91 as an NK engager in the TriKE molecules described herein can increase drug yield, increase stability, and/or increase NK-cell-mediated ADCC efficacy.

In some embodiments, an immune engager as described herein can be used to stimulate a patient's own immune system to eliminate tumor cells. Although studies show that T cells, genetically modified to express chimeric antigen receptors (CARs), are powerful clinical mediators of anti-tumor activity, production of T-CARs is costly and complex. Other disadvantages include the risk of cytokine toxicity and long-term persistence of T-CARs resulting in interaction with healthy tissue or neoplastic transformation. As described herein, a tri-specific killer engager can serve as a mediator of ADCC and can expand NK cells without the need of extracorporal genetic modification and gene therapy, providing a potential advantage over the T-CAR system. Because the immune engager is rapidly cleared, the response cannot be indefinitely sustained, perhaps reducing the risk of cytokine toxicity of the immune engagers compared to T-CARs.

In some embodiments, a tri-specific killer engager includes a cytokine. In some embodiments, a tri-specific killer engager preferably includes IL-15. IL-15 does not induce Tregs and IL-15 is a regulator of NK cells. In addition to improving activation and cytotoxicity, IL-15 can regulate and initiate anti-apoptotic and proliferative signals on NK cells, leading to enhanced NK cell expansion and survival. These characteristics can be beneficial during the use of the tri-specific killer engager in the treatment against cancer. In some embodiments, including IL-15 in the tri-specific killer engager can mediate directed delivery of the TriKE to the NK/Target cell synapse, potentially causing IL-15 to accumulate at a tumor site more effectively than systemic IL-15.

In some embodiments, a tri-specific killer engager preferably includes IL-15, anti-CD16 scFv, and anti-EpCAM scFv (1615EpCAM TriKE). In some embodiments, IL-15 acts as a crosslinker between the anti-CD16 scFv and the anti-EpCAM scFv.

In some embodiments, the immune engager increases the secretion of an immune cell-mediated cytokine. In some embodiments, the cytokine secretion is preferably antigen specific. In some embodiments, this cytokine can include IFN-γ, GM-CSF, IL-6, IL-8, and/or TNF-α. In some embodiments, this cytokine production is preferably at physiologic levels. In some embodiments, this cytokine production is at a level lower than the level observed in an IL-12/IL-18 stimulated NK cell (Papadakis et al., 2004. *J Immunol.* 172:7002-7007). As shown in Example 2, measuring hallmark inflammatory cytokines including GM-CSF, IL-6, IL-8, TNF-α using a cytokine Luminex analysis demonstrates a statistically significant difference in GM-CSF secretion between BiKE and TriKE but no difference in the secretion of other cytokines.

In some embodiments, the immune engager increases proliferation of a lymphocyte. The lymphocyte can include, for example, an NK cell, a γδ-T cell, and/or, a CD8 T cell.

Just as the 1615EpCAM133 TetraKE molecule includes more than one targeting domain, one can design a TetraKE, or larger molecule, that includes more than one NK cell engager domain and/or more than one NK activating domain.

In another aspect, this disclosure describes methods of killing a target cell in a subject. Generally, the method includes administering to the subject a TriKE molecule in an amount effective to induce NK-mediated killing of the target cells. "Treat" or variations thereof refer to reducing, limiting progression, ameliorating, or resolving, to any extent, the symptoms or signs related to a condition. As used herein, "ameliorate" refers to any reduction in the extent, severity, frequency, and/or likelihood of a symptom or clinical sign characteristic of a particular condition; "symptom" refers to any subjective evidence of disease or of a patient's condition; and "sign" or "clinical sign" refers to an objective physical finding relating to a particular condition capable of being found by one other than the patient.

A "treatment" may be therapeutic or prophylactic. "Therapeutic" and variations thereof refer to a treatment that ameliorates one or more existing symptoms or clinical signs associated with a condition. "Prophylactic" and variations thereof refer to a treatment that limits, to any extent, the development and/or appearance of a symptom or clinical sign of a condition. Generally, a "therapeutic" treatment is initiated after the condition manifests in a subject, while "prophylactic" treatment is initiated before a condition manifests in a subject. Thus, in certain embodiments, the method can involve prophylactic treatment of a subject at risk of developing a condition. "At risk" refers to a subject that may or may not actually possess the described risk. Thus, for example, a subject "at risk" for developing a specified condition is a subject that possesses one or more indicia of increased risk of having, or developing, the specified condition compared to individuals who lack the one or more indicia, regardless of the whether the subject manifests any symptom or clinical sign of having or developing the condition. Exemplary indicia of a condition can include, for example, genetic predisposition, ancestry, age, sex, geographical location, lifestyle, or medical history. Treatment may also be continued after symptoms have resolved, for example to prevent or delay their recurrence.

In some cases, the treatment can involve administering the TriKE molecule to a subject so that the TriKE molecule can stimulate endogenous NK cells in vivo. Using a TriKE molecule as a part of an in vivo can make NK cells antigen specific with simultaneous co-stimulation, enhancement of survival, and expansion, which may be antigen specific. In other cases, the TriKE can be used in vitro as an adjuvant to NK cell adoptive transfer therapy.

In another aspect, the TriKE can be designed to activate T cells rather than NK cells. In this aspect, the TriKE can generally include one or more T cell engaging domains, one or more T cell activating domains, and one or more targeting domain (that target, e.g., a tumor cell or virally-infected cell), and one or more T ell activating domains (e.g., IL-2 or other T cell enhancing cytokine, chemokine, and/or activating molecule), with each domain operably linked to the other domains.

The T cell engaging domain can include any moiety that binds to and/or activates a T cell and/or any moiety that blocks inhibition of a T cell. In some embodiments, the T cell engaging domain can include an antibody or fragment thereof that selectively binds to a component of the surface of a T cell. In other embodiments, the T cell engaging domain can include a ligand or small molecule that selectively binds to a component of the surface of a T cell.

In some embodiments, the T cell engaging domain can selectively bind to a receptor at least partially located at the surface of a T cell. In certain embodiments, the T cell engaging domain can serve a function of binding a T cell and thereby bring the T cell into spatial proximity with a target to which the targeting domain—described in more detail below—selectively binds. In certain embodiments, however, the T cell engaging domain can selectively bind to a receptor that activates the T cell and, therefore, also possess an activating function.

While described herein in the context of various embodiments in which the T cell engaging domain includes an anti-CD3 receptor scFv, the T cell engaging domain can include any antibody or other ligand that selectively binds to the CD3 receptor. Moreover, the T cell engaging domain can include an antibody or ligand that selectively binds to any T cell receptor such as, for example, an anti-CD4 antibody, an anti-CD8 antibody, an anti-LFA-1 antibody, an anti-LFA-2 antibody, an anti-CTLA4 antibody, an anti-TCR antibody, an anti-CD28 antibody, an anti-CD25 antibody, an anti-PD1 antibody, PD-L1, B7-1, B7-2, MHC molecules, CD80, CD86, B7H, an anti-SLAM antibody, or an anti-BTLA antibody.

The targeting domain can include any moiety that selectively binds to an intended target such as, for example, a tumor cell, a target in the cancer stroma, a target on an inhibitory cell such as myeloid derived suppressor cells that are CD33+, or a target on a virally-infected cell. Thus, a targeting domain can include, for example, any one of the targeting domains described above in the context of NK-activating TriKE molecules.

The T cell activating domain can include an amino acid sequence that activates T cells, promotes sustaining T cells, or otherwise promotes T cell activity. The T cell activating domain can be, or can be derived from, one or more cytokines that can activate and/or sustain T cells. As used herein, the term "derived from" refers to an amino acid fragment of a cytokine (e.g., IL-2) that is sufficient to provide T cell activating and/or sustaining activity. In embodiments that include more than one T activating domain, the T activating domains may be provided in series or in any other combination. Additionally, each cytokine-based T activating domain can include either the full amino acid sequence of the cytokine or may be an amino acid fragment, independent of the nature of other T cell activating domains included in the TriKE molecule. Exemplary cytokines on which a T cell activating domain may be based include, for example, IL-2 or any cytokine of the IL-2 family that shares a chain with the IL-2 receptor such as, for example, IL-15, IL-4, IL-7, IL-9, IL-21, and IL-13. Thus, while described in detail herein in the context of an exemplary model embodiment in which the T cell activating domain is derived from IL-2, a TriKE may be designed using a T cell activating domain that is, or is derived from, any suitable cytokine.

For brevity in this description, reference to a T cell activating domain by identifying the cytokine on which it is based includes both the full amino acid sequence of the cytokine and any suitable amino acid fragment of the cytokine. Thus, reference to an "IL-2" T cell activating domain includes a T cell activating domain that includes the full amino acid sequence of IL-2 or an T cell activating domain that includes a fragment of IL-2. In some embodiments, therefore, the T cell activating domain can include the amino acid sequence of SEQ ID NO:18.

In another aspect, this disclosure describes methods of killing a target cell in a subject. Generally, the method includes administering to the subject a TriKE molecule in an amount effective to induce T-cell-mediated killing of the target cells. Here again, the treatment may be therapeutic or prophylactic as described above in the context of methods that involve the use of an NK-activating TriKE.

Accordingly, a TriKE molecule—whether an NK-activating TriKE or a T-cell-activating TriKE—may be administered before, during, or after the subject first exhibits a symptom or clinical sign of the condition. Treatment initiated before the subject first exhibits a symptom or clinical sign associated with the condition may result in decreasing the likelihood that the subject experiences clinical evidence of the condition compared to a subject to which the TriKE molecule is not administered, decreasing the severity of symptoms and/or clinical signs of the condition, and/or completely resolving the condition. Treatment initiated after the subject first exhibits a symptom or clinical sign associated with the condition may result in decreasing the severity of symptoms and/or clinical signs of the condition compared to a subject to which the composition is not administered, and/or completely resolving the condition.

The TriKE molecule can be any embodiment of the TriKE molecule described above having a targeting domain that selectively binds to an appropriate target cell population. In some cases, the target cell can include a tumor cell so that the method can involve treating cancer associated with the tumor cells. Thus, in some embodiments, the method can include ameliorating at least one symptom or clinical sign of the tumor.

In embodiments in which the target cell includes a tumor cell, the method can further include surgically resecting the tumor and/or reducing the size of the tumor through chemical (e.g., chemotherapeutic) and/or radiation therapy. Exemplary tumors that may be treated include tumors associated with prostate cancer, lung cancer, colon cancer, rectum cancer, urinary bladder cancer, melanoma, kidney cancer, renal cancer, oral cavity cancer, pharynx cancer, pancreas cancer, uterine cancer, thyroid cancer, skin cancer, head and neck cancer, cervical cancer, ovarian cancer and/or hematopoietic cancer.

In various embodiments, the TriKE targeting domain can include a polypeptide that selectively binds to, for example, EGFR, HER2/neu EpCAM, CSPG4, HSPG2, IGF-1, CD38, CD19, CD20, CD22, CD30, CD52, CD33, ROR-1, UPAR, VEGFR, CD33, LIV-1, SGN-CD70A, CD70, IL-3, IL-4R, CD133, mesothelin, the epithelial-mesenchymal transition (EMT), TRAIL, CD38, CD45, CD74, CD23, or cancer viral markers such as HIV.

As used herein, a "subject" can be any animal such as, for example, a mammal (e.g., dog, cat, horse, cow, sheep, goat, monkey, etc.). In certain embodiments, the subject can be a human.

A TriKE molecule described herein may be formulated with a pharmaceutically acceptable carrier. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with a TriKE molecule without causing any undesirable biological effects or interacting in a deleterious manner with any of the other components of the pharmaceutical composition in which it is contained.

A TriKE molecule may therefore be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical composition can be administered to a mucosal surface, such as by administration to, for example, the nasal or respiratory mucosa (e.g., by spray or aerosol). A composition also can be administered via a sustained or delayed release.

Thus, a TriKE molecule may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

A formulation may be conveniently presented in unit dosage form and may be prepared by methods well known in the art of pharmacy. Methods of preparing a composition with a pharmaceutically acceptable carrier include the step of bringing a TriKE molecule into association with a carrier that constitutes one or more accessory ingredients. In general, a formulation may be prepared by uniformly and/or intimately bringing the active molecule into association with a liquid carrier, a finely divided solid carrier, or both, and then, if necessary, shaping the product into the desired formulations.

The amount of TriKE molecule administered can vary depending on various factors including, but not limited to, the specific TriKE molecule being used, the weight, physical condition, and/or age of the subject, and/or the route of administration. Thus, the absolute weight of TriKE molecule included in a given unit dosage form can vary widely, and depends upon factors such as the species, age, weight and physical condition of the subject, and/or the method of administration. Accordingly, it is not practical to set forth generally the amount that constitutes an amount of TriKE molecule effective for all possible applications. Those of ordinary skill in the art, however, can readily determine the appropriate amount with due consideration of such factors.

In some embodiments, the method can include administering sufficient TriKE molecule to provide a dose of, for example, from about 100 ng/kg to about 50 mg/kg to the subject, although in some embodiments the methods may be performed by administering TriKE molecule in a dose outside this range. In some of these embodiments, the method includes administering sufficient TriKE molecule to provide a dose of from about 10 μg/kg to about 5 mg/kg to the subject, for example, a dose of from about 100m/kg to about 1 mg/kg.

Alternatively, the dose may be calculated using actual body weight obtained just prior to the beginning of a treatment course. For the dosages calculated in this way, body surface area (m²) is calculated prior to the beginning of the treatment course using the Dubois method: $m^2 = (wt \, kg^{0.425} \times height \, cm^{0.725}) \times 0.007184$.

In some embodiments, the method can include administering sufficient TriKE molecule to provide a dose of, for example, from about 0.01 mg/m² to about 10 mg/m².

In some embodiments, a TriKE molecule may be administered, for example, from a single dose to multiple doses per week, although in some embodiments the method can be performed by administering a TriKE molecule at a frequency outside this range. In certain embodiments, a TriKE molecule may be administered from about once per month to about five times per week.

In some embodiments, the method further includes administering one or more additional therapeutic agents. The one or more additional therapeutic agents may be administered before, after, and/or coincident to the administration of a TriKE molecule. A TriKE molecule and the additional therapeutic agents may be co-administered. As used herein, "co-administered" refers to two or more components of a combination administered so that the therapeutic or prophylactic effects of the combination can be greater than the therapeutic or prophylactic effects of either component administered alone. Two components may be co-administered simultaneously or sequentially. Simultaneously co-administered components may be provided in one or more pharmaceutical compositions. Sequential co-administration of two or more components includes cases in which the components are administered so that each component can be present at the treatment site at the same time. Alternatively, sequential co-administration of two components can include cases in which at least one component has been cleared from a treatment site, but at least one cellular effect of administering the component (e.g., cytokine production, activation of a certain cell population, etc.) persists at the treatment site until one or more additional components are administered to the treatment site. Thus, a co-administered combination can, in certain circumstances, include components that never exist in a chemical mixture with one another. In other embodiments, the TriKE molecule and the additional therapeutic agent may be administered as part of a mixture or cocktail. In some aspects, the administration of TriKE molecule may allow for the effectiveness of a lower dosage of other therapeutic modalities when compared to the administration of the other therapeutic agent or agents alone, thereby decreasing the likelihood, severity, and/or extent of the toxicity observed when a higher dose of the other therapeutic agent or agents is administered.

Exemplary additional therapeutic agents include altretamine, amsacrine, L-asparaginase, colaspase, bleomycin, busulfan, capecitabine, carboplatin, carmustine, chlorambucil, cisplatin, cladribine, cyclophosphamide, cytophosphane, cytarabine, dacarbazine, dactinomycin, daunorubicin, docetaxel, doxorubicin, epirubicin, etoposide, fluorouracil, fludarabine, fotemustine, ganciclovir, gemcitabine, hydroxyurea, idarubicin, ifosfamaide, irinotecan, lomustine, melphalan, mercaptopurine, methotrexate, mitoxantrone, mitomycin C, nimustine, oxaliplatin, paclitaxel, pemetrexed, procarbazine, raltitrexed, temozolomide, teniposide, tioguanine, thiotepa, topotecan, vinblastine, vincristine, vindesine, and vinorelbine.

In some embodiments, of the method can include administering sufficient TriKE molecule as described herein and administering the at least one additional therapeutic agent demonstrate therapeutic synergy. In some aspects of the methods of the present invention, a measurement of response to treatment observed after administering both a TriKE molecule as described herein and the additional therapeutic agent is improved over the same measurement of response to treatment observed after administering either the TriKE molecule or the additional therapeutic agent alone. In some embodiments, an additional therapeutic agent can include an additional agent that targets EpCAM including, for example, an EpCAM specific monoclonal antibody, such as, for example, Catumaxomab, a monoclonal hybrid antibody targeting EpCAM and CD3.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Cell Isolation, Patients and Samples

PBMCs from age-matched normal donors were isolated from adult blood obtained from Memorial Blood Center (Minneapolis, Minn.) by centrifugation using a Histopaque gradient (Sigma-Aldrich, St. Louis, Mo.) and cryopreserved. For the post-transplant patient sample study, matched sibling donor allogeneic hematopoietic cell transplant samples were used from an immune reconstitution tissue bank. Recipient PBMCs were collected at either day 100 [n=5] or earlier (day 20-44) [n=5] after transplant and cryopreserved for future use. All samples were obtained after informed consent, using guidelines approved by the Committee on the Use of Human Subjects in Research at the University of Minnesota in accordance with the Declaration of Helsinki.

Cell Lines

HL-60, a CD33$^+$ human acute promyelocytic leukemia cell line (ATCC, Manassas, Va.), was cultured in Iscove's medium (Invitrogen, Carlsbad, Calif.) supplemented with 20% FBS (Gibco-Invitrogen) and 100 U/mL penicillin and 100 U/mL streptomycin (Invitrogen, Carlsbad, Calif.) at 37° C. and 5% $CO_2$. The control human colorectal carcinoma cell line HT-29 (ATCC) was cultured at 37° C. with 5% $CO_2$ in Dulbecco's Modified Eagle's Medium (DMEM), high glucose (Invitrogen, Carlsbad, Calif.) supplemented with 10% FBS and 100 U/mL penicillin and 100 U/mL streptomycin.

Construction, Expression and Purification of BiKEs and TriKEs

The hybrid polynucleotide encoding 161533 (SEQ ID NO:1) was synthesized using DNA shuffling and DNA ligation techniques (Vallera et al., 2013 Cancer Biother Radiopharm 4:274-482; Vallera et al., 2009. Leuk Res 33(9):

1233-1242). Coding regions for the $V_L$ and $V_H$ of each scFv were linked by a fragment encoding G45 linker. In its final configuration, the 161533 NcoI/XhoI polynucleotide has a start codon followed first by coding regions for anti-human CD16 scFv (McCall et al., 1999. Mol Immunol. 7:433-445), a 20 amino acid flanking polypeptide (PSGQAGAAAS-ESLFVSNHAY; SEQ ID NO:3), human IL-15N72D, a seven amino acid flanking polypeptide (EASGGPE; SEQ ID NO:4), and then the anti-CD33 scFv. The polynucleotide was spliced into the pET28c expression vector and inclusion bodies expressed. DNA-sequencing analysis (Biomedical Genomics Center, University of Minnesota) was used to verify that the ploynucleotide was correct in sequence and cloned in frame.

The same components were used to construct a hybrid polynucleotide encoding 163315 (SEQ ID NO:7), except that the order of the components was CD16scFv, the flanking polypeptide PSGQAGAAASESLFVSNHAY (SEQ ID NO:3), anti-CD33 scFv, the flanking polypeptide EASGGPE (SEQ ID NO:4), then human IL-15.

Plasmid was transformed into the Escherichia coli strain BL21(DE3)(EMD, Madison Wis.). Bacteria were grown in 600 ml Luria Broth supplemented with 100 μg/ml kanamycin in a 2 L flask at 37° C. with shaking. Expression of the hybrid polynucleotide was induced by the addition of iso-propyl-b-D-thiogalactopyranoside (IPTG, FisherBiotech Fair Lawn, N.J.). Two hours after induction, the bacteria were harvested by centrifugation. The cell pellets were suspended and homogenized using a polytron homogenizer. After sonication and centrifugation, the pellets were extracted with 0.3% sodium Deoxycholate, 5% Triton X-100, 10% Glycerin, 50 mM Tris, 50 mM NaCl, 5 mM EDTA, pH 8.0 and inclusion bodies extensively washed to remove endotoxin.

The proteins were refolded using a sodium N-lauroyl-sarcosine (SLS) air oxidation method modified from a previously reported procedure for isolating scFv (Vallera et al., 2005. Leuk Res 29(3):331-341). Refolded 161533 was purified by FPLC ion exchange chromatography (Q Sepharose Fast Flow, Sigma, St. Louis, Mo.) using a stepwise gradient from 0.2 M to 0.5 M NaCl in 20 mM Tris-HCl, pH 9.0 over four column volumes.

Flow Cytometry

Cells were immunophenotyped with the following fluorescent-labeled monoclonal antibodies (mAb) against: PE-Cy7-conjugated CD56 (HCD56; BioLegend, Inc., San Diego, Calif.), ECD/PE-CF594-conjugated CD3 (UCHT1; Beckman Coulter, Brea, Calif.), APC-Cy7-conjugated CD16 (3G8; BioLegend, Inc.), Pacific Blue-conjugated CD45 (HI30; BioLegend, Inc.), PerCP-Cy5.5/FITC-conjugated anti-human CD107a (LAMP-1) (H4A3; BioLegend, Inc.), Pacific Blue/BV421-conjugated anti-human IFN-γ (4S.B3; BioLegend, Inc.), FITC/Alexa Fluor 647-conjugated TNF-α (MAbl1; BioLegend, Inc.), FITC/PE-conjugated CD33 (P67.6; BD Biosciences), and APC-conjugated CD45 (HI30; BioLegend, Inc.), FITC-conjugated EpCAM; (BioLegend, Inc.). Phenotypic acquisition of cells was performed on the LSRII (BD Biosciences) and analyzed with FlowJo software (Tree Star Inc., Ashland, Oreg.).

CD107a and IFNγTNFα Functional Flow Assay

Post-transplant patient PBMCs or primary AML blasts were thawed and placed in RPMI-10 overnight. The next night, the PBMCs were incubated with 50 nM 1633 BiKE or 161533 TriKE. The next morning cells were washed and another round of 50 nM 1633 BiKE or 161533 TriKE was added to address any possible issues with molecule internalization. HL-60 Targets or primary AML blasts were added immediately after to generate a 5:1 effector to target ratio. PBMCs, HL-60 targets or primary AML blasts, and BiKE or TriKE molecules were co-cultured for four hours and CD107a expression and intracellular IFN-γ and TNF-α production were evaluated as previously described (Vallera et al., 2013 *Cancer Biother Radiopharm* 4:274-282).

Proliferation Assay

PBMCs from post-transplant patients (day 100 or earlier [day 20-44]) were labeled with CELLTRACE Violet Cell Proliferation Dye (Thermo Fisher Scientific, Waltham, Mass.), per manufacturer's protocol, placed in culture medium with HL-60 target cells at 5:1 (E:T) ratio, and treated with 50 nM 1633 BiKE or 161533 TriKE. Cells were then harvested seven days later and analyzed for viability, through Live/Dead staining, and proliferation, through dilution of CELLTRACE, in the NK cell (CD56⁺CD3⁻) population.

51-Chromium Release Cytotoxicity Assay

Cytotoxicity was evaluated by 4-hour $^{51}$Cr-release assays. Briefly, resting PBMC from normal donors treated with the 1633 BiKE (10 μg/mL), scFvCD16 control reagent (10 μg/mL) or no reagent were co-cultured for four hours with $^{51}$Cr-labeled or HL-60 targets at varying E:T ratios. For post-transplant study PBMCs cells were with HL-60 targets at a 20:1 (E:T) ratio in the presence of 50 nM 1633 BiKE or 50 nM 161533 TriKE. $^{51}$Cr release was measured by a gamma scintillation counter (Perkin Elmer, Walthman, MA) and specific target lysis was determined (Vallera et al., 2013. *Cancer Biother Radiopharm* 4:274-282).

In vivo Mouse Study and Imaging

NSG mice (n=5/group) were conditioned with 275 cGy and injected IV with 0.75×10⁵ HL-60-luc S4 subcultured for tumor invasiveness. Drug treatment was begun on day 3. A single course of treatment consisted of an intraperitoneal (IP) injection of 20 μg of drug given every day for a week (MTWThF) and mice were treated for three weeks. The control group received no NK cells while the 1633 BiKE and the 161533 TriKE groups received 1×10⁶ NK cells, calculated from a CD3/CD19 magnetically depleted product, three days after injection of the HL-60-luc cells. The HL-60-luc cells contain a luciferase reporter, allowing for imaging of the mice each week to determine their bioluminescent activity and monitor cancer leukemia progression as described previously (Waldron et al., 2011. *Mol Cancer Ther* 10(10):1829-1838.). Briefly, mice were injected with 100 μl of 30 mg/ml luciferin substrate 10 minutes prior to imaging and then anesthetized via inhalation of isoflurane gas. The mice were then imaged using the Xenogen Ivis 100 imaging system and analyzed with Living Image 2.5 software (Xenogen Corporation, Hopkington Mass.). On day 20, all the animals were bled and two-minute exposures were made and units for the regions of interest (ROI) were expressed as photons/sec/cm2/sr. The blood was analyzed by flow cytometry for presence of human CD45⁺CD56⁺CD3⁻ NK cells. A second experiment was performed to verify reproducibility of data.

Statistical Analysis

Grouped data were expressed as mean±standard error mean (SEM). Differences between two groups were analyzed by Student's t test. Multiple comparisons were analyzed by paired one-way ANOVA with Tukey correction. Analysis was carried out in Graphpad Prism software.

Example 2

Construction of 1615EpCAM TriKE

Synthesis and assembly of a hybrid polynucleotide encoding 1615EpCAM TriKE (SEQ ID NO:8) was accomplished using DNA shuffling and ligation techniques. The fully-assembled 1615EpCAM polynucleotide has, from the 5' end to the 3' end, an NcoI restriction site; an ATG initiation codon; coding regions encoding the $V_H$ and $V_L$ regions of human CD16 (NM3E2) derived from a phage display library produced by McCall et al. (*Mol Immunol.*, 1999, 36:433-445), a 20 amino acid segment (PSGQAGAAASESLFVSN-HAY; SEQ ID NO:3), modified IL-15N72D, a seven amino acid linker (EASGGPE; SEQ ID NO:4), and the humanized anti-EPCAM scFv from the antibody MOC-31; and finally a XhoI restriction site. The resulting 1914 bp NcoI/XhoI polynucleotide was spliced into the pET21c expression vector under control of an isopropyl-β-D-thiogalactopyranoside (IPTG) inducible T7 promoter. DNA sequencing analysis (Biomedical Genomics Center, University of Minnesota, Minn., USA) was used to verify that the ploynucleotide was correct in sequence and had been cloned in frame. Other constructs used in this study, were created in a similar manner but including coding regions for monospecific anti-CD16 scFv, and anti-EpCAM scFv.

Inclusion Body Isolation

Bacterial protein expression was performed with Escherichia coli strain BL21 (DE3) (Novagen, Madison, Wis., USA) by plasmid transformation. After overnight culture, bacteria were grown in 800 ml Luria broth containing 50 mg/ml kanamycin. Induction of gene expression occurred when culture media reached an optical density (OD) 600 of 0.65 with the addition of IPTG (FischerBiotech, Fair Lawn, N.J., USA). Two hours after induction, bacteria were harvested (from 5 liters cultured media a 43 g bacterial pellet was isolated). Next, the pellet was homogenized in a buffer solution (50 mM Tris, 50 mM NaCl, and 5 mM EDTA pH 8.0), sonicated and centrifuged. Pellets were extracted with 0.3% sodium deoxycholate, 5% Triton X-100, 10% glycerin, 50 mmol/L Tris, 50 mmol/L NaCl, 5 mmol/L EDTA (pH 8.0) and washed (final pellet weight: 12.5 g).

Refolding and Purification

Refolding and purification was performed as previously described (Schmohl et al., 2016. *Target Oncol.* 11(3):353-361). Briefly, in order to refold, proteins from inclusion bodies (IB) where dissolved at 20:1 (mg wet weight/mL) in solubilization buffer (7 M Guanidine Hydrochloride, 50 mM Tris, 50 mM NaCl, 5 mM EDTA and 50 mM DTT, pH 8.0). Following a one-hour incubation at 37° C., pellets were removed by centrifugation. The supernatant was diluted (20-fold) with refolding buffer (50 mM Tris-HCl, 50 mM NaCl, 0.8 mM L-arginine, 20% glycerin, 5 mM EDTA and 1 mM GSSG, pH 8.0) at 4° C. for two days. The buffer was removed by 10-fold dialysis against 20 mM Tris-HCl, pH 9.0 in 20 mM Tris-HCl, pH 9.0 over four column volumes. SDS-PAGE analysis was performed to evaluate purity. The fusion proteins were stained with Simply Blue life Stain (Invitrogen, Carlsbad, Calif.). The size of the TriKE was about 68860 Da.

NK Cell Isolation and Purification

A histopaque gradient (Sigma-Aldrich, St. Louis, Mo., USA) and SEPMATE tubes (Stemcell Technologies, Inc., Vancouver, Canada) were used to isolate peripheral blood mononuclear cells (PBMCs) from adult blood (Memorial Blood Center, Minneapolis, Minn., USA) of healthy volunteers and to obtain enriched NK cells via negative selection using magnetic beads per the manufacturer's protocol (Stemcell Technologies, Inc., Vancouver, Canada). Samples were obtained after informed consent and in accordance with the University of Minnesota human subjects Institutional Review Board and the Declaration of Helsinki.

Tissue Culture

The following cell lines were obtained from the American Type Culture Collection: Breast cancer cell lines BT-474, SK-BR-3; prostate cancer cell lines PC-3, DU145; head-and heck cancer cell lines UMSCC-11B, NA; ovarian cancer cell line SKOV-1; colon carcinoma cell line HT-29; lung cancer cell line Calu-3; Burkitts lymphoma cell line Daudi; acute myeloid leukemia cell line HL-60; human glioblastoma cell line U87. Carcinoma and glioblastoma cell lines were grown in monolayers using tissue flasks (Fogh et al., 1977. *J Natl Cancer Inst* 59:221-226), HL-60 and Daudi cell lines (Klein et al., 1968. *Cancer Res* 28:1300-1310) were grown in suspension. Cells were maintained in either RPMI 1640 (BT-474, SK-BR-3, PC-3, DU-145, HT-29, Daudi, HL60, Calu-3), DMEM (UMSCC-11B, NA, SK-OV-3, U87) supplemented with 10% fetal bovine serum and 2 mmol/L L-glutamine. In addition to the preceding supplements, BT-474 media contained 10 IU/mL insulin. Cells were incubated in a humidified constant 37° C. atmosphere containing 5% $CO_2$. When cells were 90% confluent, they were passaged using trypsin-EDTA for detachment. Cell counts were conducted using a standard hemacytometer. Only cells with a viability >95%, as determined by trypan blue exclusion, were used for experiments.

Binding/Blocking Assay

To evaluate binding, $4 \times 10^5$ of the respective cancer cells (BT-474, PC-3, UMSCC-11B, Calu-3, Daudi, U87) were washed and incubated in 4° C. with 10 nM Fluorescein isothiocyate (FITC)-labeled anti-EpCAM scFv for 30 minutes. For the blocking assay 200 nM FITC labeled 1615EpCAM TriKE was added to either 500 nM of anti-EpCAM scFv or an anti-CD22-CD19 scFv construct and was incubated for 30 minutes in 4° C. with HT-29 colon carcinoma cells. After washing, staining intensity was evaluated with an LSRII flow cytometer (BD Biosciences, San Jose, Calif., USA).

CD107a Degranulation Assay

Flow cytometry assays measuring cytolytic degranulation via CD107a expression and IFN-γ presence were performed previously reported (Gleason et al., 2012. *Mol Cancer Ther* 11:2674-2684). PBMCs were incubated overnight (37° C., 5% $CO_2$) in RPMI 1640 supplemented with 10% fetal calf serum and with recombinant IL-12 10 ng/ml (PeproTech, Rocky Hill, N.J.) and IL-18 100 ng/ml (R&D Systems, Inc., Minneapolis, Minn., USA) as a positive control. Cells were washed in 1× PBS, treated with 30 nM of 1615EpCAM TriKE or other drugs and incubated for 10 minutes at 37° C. with 5% $CO_2$. FITC-conjugated anti-human CD107a monoclonal antibody (mAb) (LAMP-1) (BD Biosciences, San Jose, Calif.) was added and further incubated for one hour with respective target cells (BT-474, SK-BR-3, PC-3, DU-145, HT-29, HL60, UMSCC-11B, NA, SK-OV-3). GolgiStop (1:1500) (BD Biosciences, San Jose, Calif.) and GolgiPlug (1:1000) (BD Biosciences, San Jose, Calif.) were added and cells were further incubated for three hours. Cells were washed in 1× PBS and stained with PE/Cy7-conjugated anti-CD56 mAb, APC/Cy 7-conjugated anti-CD16 mAb and PE-CF594-conjugated anti-CD3 mAb (BioLegend, Inc., San Diego, Calif.), incubated for 15 minutes and then fixed in 2% paraformaldehyde. Then cells were prepared for intracellular stain using permeabilization buffer (BD Biosciences, San Jose, Calif.). Cells were incubated with Pacific Blue-conjugated anti-human IFN-γ (BioLegend, Inc., San Diego, Calif.) for 20 minutes, washed and evaluated by FACS analysis using a LSRII flow cytometer (BD Biosciences, San Jose, Calif.). For compensation CompBead Plus Anti-Mouse Ig, κ/Negative Control (BSA) Compensation Plus (7.5 μm) particles (BD Biosciences, San Jose, Calif.) were used.

Chromium-51 Release Cytotoxicity Assay

HT-29 target cells were labeled for 1 hour with 1 μCi of $^{51}$Cr per $1 \times 10^5$ target cells at 37° C., 5% $CO_2$. Washing procedures were performed to remove excess $^{51}$Cr. Labeled target cells were added to the wells of 96-well round-bottom plates ($5 \times 10^3$ cells). Resting effector NK cells treated with 1615EpCAM TriKE, EpCAM16 BiKE or negative controls were added to the plates. E:T ratio ranged between 20:1 and 0.08:1. The amount of $^{51}$Cr released, which corresponds to target cell death, was measured by a gamma scintillation counter, and the percent target cell lysis was calculated as follows: [(experimental lysis–spontaneous lysis)/(maximal lysis–spontaneous lysis)]×100. To determine maximal lysis, $^{51}$Cr-labeled target cells were treated with 3% Triton X for four hours.

Luminex

For analysis of chemokines and cytokines, purified NK cells from six healthy volunteers were co-incubated in 96 well plates for 24 hours with HT-29 colon carcinoma cells at a 2:1 E:T ratio and the respective drug in a concentration of 50 nM at 37° C., 5% $CO_2$. After a 24 hour incubation time, cells were centrifuged and supernatants were collected and stored at −80° C. until being analyzed. GM-CSF, IL-6, IL-8 and TNF-α (R&D Systems, Inc., Minneapolis, Minn.) were determined using the Luminex system (MAGPIX, Luminex, Austin, Tex.). Values represent pg/ml and were interpolated from standard curves of the recombinant human proteins by using Xponent 4.2 software (Luminex, Austin, Tex.).

Proliferation and Viability Assays

PBMCs or enriched NK cells from healthy donors were labeled with CELLTRACE Violet Cell Proliferation Dye (Thermo Fisher Scientific, Waltham, Mass.) according to the manufacturer's protocol. After labeling, cells were cultured with 50 nM concentrations of the respective drugs. Cells were harvested after seven days, stained for viability with Live/Dead reagent (Invitrogen, Carlsbad, Calif.) and surface stained for anti-CD56 PE/Cy7 (BioLegend, Inc., San Diego, Calif., USA) and anti-CD3 PE-CF594 (BD Biosciences, San Jose, Calif.) to gate on the viable CD3⁻CD56⁺ population. Data were analyzed with FlowJo software version 7.6.5. (FlowJo, LLC, Ashland, Oreg., USA).

Statistical Analyses

Data are presented as mean+/−standard deviation. Differences between two groups were analyzed by Student's t test or one-way-ANOVA. Analysis and presentation of data was done with GraphPad Prism 5 (GraphPad Software, Inc., La Jolla, Calif.).

Example 3

Construction of EF91(llama anti-human IL16)-IL15-CD33

Synthesis and assembly of a hybrid polynucleotide encoding the TriKE EF91(llama anti-human IL16)-IL15-CD33 (SEQ ID NO:14) was accomplished using DNA shuffling and ligation techniques. The fully-assembled polynucleotide has, from the 5' end to the 3' end, an NcoI restriction site; an ATG initiation codon; coding regions encoding the the $V_H$ and $V_L$ regions of EF91 (llama anti-human IL16), a 20 amino acid segment (PSGQAGAAASESLFVSNHAY; SEQ ID NO:3), modified IL-15, a seven amino acid linker (EASGGPE; SEQ ID NO:4), and the humanized anti-CD33 scFv; and finally a XhoI restriction site. The resulting NcoI/XhoI polynucleotide was spliced into the pET21d expression vector under control of an isopropyl-β-D-thio-galactopyranoside (IPTG) inducible T7 promoter.

Example 4

Construction of 1615 AntiHIV

Since 1615x is a platform technology, it is also possible to use anti-viral scFvs that are or are not associated with cancer development. Synthesis and assembly of a hybrid polynucleotide encoding the TriKE 1615antiHIV (SEQ ID NO:19) was accomplished using DNA shuffling and ligation techniques. The fully-assembled polynucleotide has, from the 5' end to the 3'end, an NcoI restriction site; an ATG initiation codon; the $V_H$ and $V_L$ regions of the anti-CD16 scFv, a 20 amino acid segment (PSGQAGAAASESLFVSN-HAY; SEQ ID NO:3), modified IL-15, a seven amino acid linker (EASGGPE; SEQ ID NO:4), and an anti-HIV scFv; and finally a XhoI restriction site.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

```
              SEQUENCE LISTING FREE TEXT
                                    SEQ ID NO: 1
        MEVQLVESGG GVVRPGGSLR LSCAASGFTF

DDYGMSWVRQ APGKGLEWVS GINWNGGSTG
```

```
              -continued
        YADSVKGRFT ISRDNAKNSL YLQMNSLRAE

DTAVYYCARG RSLLFDYWGQ GTLVTVSRGG

GGSGGGGSGG GGSSELTQDP AVSVALGQTV

RITCQGDSLR SYYASWYQQK PGQAPVLVIY

GKNNRPSGIP DRFSGSSSGN TASLTITGAQ

AEDEADYYCN SRDSSGNHVV FGGGTKLTVL

PSGQAGAAAS ESLFVSNHAY NWVNVISDLK

KIEDLIQSMH IDATLYTESD VHPSCKVTAM

KCFLLELQVI SLESGDASIH DTVENLIILA

NDSLSSNGNV TESGCKECEE LEEKNIKEFL

QSFVHIVQMF INTSEASGGP EQVQLVQSGA

EVKKPGSSVK VSCKASGYTF TDYNMHWVRQ

APGQGLEWIG YIYPYNGGTG YNQKFKSKAT

ITADESTNTA YMELSSLRSE DTAVYYCARG

RPAMDYWGQG TLVTVSSGGG GSGGGGSGGG

GSDIQMTQSP SSLSASVGDR VTITCRASES

VDNYGISFMN WFQQKPGKAP KLLIYAASNQ

GSGVPSRFSG SGSGTDFTLT ISSLQPDDFA

TYYCQQSKEV PWTFGQGTKV EIK

SEQ ID NO: 2
        MEVQLVESGG GVVRPGGSLR LSCAASGFTF

DDYGMSWVRQ APGKGLEWVS GINWNGGSTG

YADSVKGRFT ISRDNAKNSL YLQMNSLRAE

DTAVYYCARG RSLLFDYWGQ GTLVTVSRGG

GGSGGGGSGG GGSSELTQDP AVSVALGQTV

RITCQGDSLR SYYASWYQQK PGQAPVLVIY

GKNNRPSGIP DRFSGSSSGN TASLTITGAQ

AEDEADYYCN SRDSSGNHVV FGGGTKLTVL

PSGQAGAAAS ESLFVSNHAY QVQLVQSGAE

VKKPGSSVKV SCKASGYTFT DYNMHWVRQA

PGQGLEWIGY IYPYNGGTGY NQKFKSKATI

TADESTNTAY MELSSLRSED TAVYYCARGR

PAMDYWGQGT LVTVSSGGGG SGGGGSGGGG

SDIQMTQSPS SLSASVGDRV TITCRASESV

DNYGISFMNW FQQKPGKAPK LLIYAASNQG

SGVPSRFSGS GSGTDFTLTI SSLQPDDFAT

YYCQQSKEVP WTFGQGTKVE IK

SEQ ID NO: 3
        PSGQAGAAAS ESLFVSNHAY

SEQ ID NO: 4
        EASGGPE
```

-continued

SEQ ID NO: 5

MEVQLVESGG GVVRPGGSLR LSCAASGFTF

DDYGMSWVRQ APGKGLEWVS GINWNGGSTG

YADSVKGRFT ISRDNAKNSL YLQMNSLRAE

DTAVYYCARG RSLLFDYWGQ GTLVTVSRGG

GGSGGGGSGG GGSSELTQDP AVSVALGQTV

RITCQGDSLR SYYASWYQQK PGQAPVLVIY

GKNNRPSGIP DRFSGSSSGN TASLTITGAQ

AEDEADYYCN SRDSSGNHVV FGGGTKLTVL

NWVNVISDLK KIEDLIQSMH IDATLYTESD

VHPSCKVTAM KCFLLELQVI SLESGDASIH

DTVENLIILA NDSLSSNGNV TESGCKECEE

LEEKNIKEFL QSFVHIVQMF INTSQVQLVQ

SGAEVKKPGS SVKVSCKASG YTFTDYNMHW

VRQAPGQGLE WIGYIYPYNG GTGYNQKFKS

KATITADEST NTAYMELSSL RSEDTAVYYC

ARGRPAMDYW GQGTLVTVSS GGGGSGGGGS

GGGGSDIQMT QSPSSLSASV GDRVTITCRA

SESVDNYGIS FMNWFQQKPG KAPKLLIYAA

SNQGSGVPSR FSGSGSGTDF TLTISSLQPD

DFATYYCQQS KEVPWTFGQG TKVEIK

SEQ ID NO: 6

MENWVNVISD LKKIEDLIQS MHIDATLYTE

SDVHPSCKVT AMKCFLLELQ VISLESGDAS

IHDTVENLII LANDSLSSNG NVTESGCKEC

EELEEKNIKE FLQSFVHIVQ MFINTSPSGQ

AGAAASESLF VSNHAYEVQL VESGGGVVRP

GGSLRLSCAA SGFTFDDYGM SWVRQAPGKG

LEWVSGINWN GGSTGYADSV KGRFTISRDN

AKNSLYLQMN SLRAEDTAVY YCARGRSLLF

DYWGQGTLVT VSRGGGGSGG GGSGGGGSSE

LTQDPAVSVA LGQTVRITCQ GDSLRSYYAS

WYQQKPGQAP VLVIYGKNNR PSGIPDRFSG

SSSGNTASLT ITGAQAEDEA DYYCNSRDSS

GNHVVFGGGT KLTVLEASGG PEQVQLVQSG

AEVKKPGSSV KVSCKASGYT FTDYNMHWVR

QAPGQGLEWI GYIYPYNGGT GYNQKFKSKA

TITADESTNT AYMELSSLRS EDTAVYYCAR

GRPAMDYWGQ GTLVTVSSGG GGSGGGGSGG

GGSDIQMTQS PSSLSASVGD RVTITCRASE

SVDNYGISFM NWFQQKPGKA PKLLIYAASN

-continued

QGSGVPSRFS GSGSGTDFTL TISSLQPDDF

ATYYCQQSKE VPWTFGQGTK VEIK

SEQ ID NO: 7

MEVQLVESGG GVVRPGGSLR LSCAASGFTF

DDYGMSWVRQ APGKGLEWVS GINWNGGSTG

YADSVKGRFT ISRDNAKNSL YLQMNSLRAE

DTAVYYCARG RSLLFDYWGQ GTLVTVSRGG

GGSGGGGSGG GGSSELTQDP AVSVALGQTV

RITCQGDSLR SYYASWYQQK PGQAPVLVIY

GKNNRPSGIP DRFSGSSSGN TASLTITGAQ

AEDEADYYCN SRDSSGNHVV FGGGTKLTVL

PSGQAGAAAS ESLFVSNHAY QVQLVQSGAE

VKKPGSSVKV SCKASGYTFT DYNMHWVRQA

PGQGLEWIGY IYPYNGGTGY NQKFKSKATI

TADESTNTAY MELSSLRSED TAVYYCARGR

PAMDYWGQGT LVTVSSGGGG SGGGGSGGGG

SDIQMTQSPS SLSASVGDRV TITCRASESV

DNYGISFMNW FQQKPGKAPK LLIYAASNQG

SGVPSRFSGS GSGTDFTLTI SSLQPDDFAT

YYCQQSKEVP WTFGQGTKVE IKEASGGPEN

WVNVISDLKK IEDLIQSMHI DATLYTESDV

HPSCKVTAMK CFLLELQVIS LESGDASIHD

TVENLIILAN DSLSSNGNVT ESGCKECEEL

EEKNIKEFLQ SFVHIVQMFI NTS

SEQ ID NO: 8

MEVQLVESGG GVVRPGGSLR LSCAASGFTF

DDYGMSWVRQ APGKGLEWVS GINWNGGSTG

YADSVKGRFT ISRDNAKNSL YLQMNSLRAE

DTAVYYCARG RSLLFDYWGQ GTLVTVSRGG

GGSGGGGSGG GGSSELTQDP AVSVALGQTV

RITCQGDSLR SYYASWYQQK PGQAPVLVIY

GKNNRPSGIP DRFSGSSSGN TASLTITGAQ

AEDEADYYCN SRDSSGNHVV FGGGTKLTVL

PSGQAGAAAS ESLFVSNHAY NWVNVISDLK

KIEDLIQSMH IDATLYTESD VHPSCKVTAM

KCFLLELQVI SLESGDASIH DTVENLIILA

NDSLSSNGNV TESGCKECEE LEEKNIKEFL

QSFVHIVQMF INTSEASGGP EDIQMTQSPS

SLSASVGDRV TITCRSTKSL LHSNGITYLY

WYQQKPGKAP KLLIYQMSNL ASGVPSRFSS

SGSGTDFTLT ISSLQPEDFA TYYCAQNLEI

PRTFGQGTKV ELKRATPSHN SHQVPSAGGP

-continued

TANSGTSGEV QLVQSGPGLV QPGGSVRISC

AASGYTFTNY GMNWVKQAPG KGLEWMGWIN

TYTGESTYAD SFKGRFTFSL DTSASAAYLQ

INSLRAEDTA VYYCARFAIK GDYWGQGTLL

TVSS

SEQ ID NO: 9

MEVQLVESGG GVVRPGGSLR LSCAASGFTF

DDYGMSWVRQ APGKGLEWVS GINWNGGSTG

YADSVKGRFT ISRDNAKNSL YLQMNSLRAE

DTAVYYCARG RSLLFDYWGQ GTLVTVSRGG

GGSGGGGSGG GGSSELTQDP AVSVALGQTV

RITCQGDSLR SYYASWYQQK PGQAPVLVIY

GKNNRPSGIP DRFSGSSSGN TASLTITGAQ

AEDEADYYCN SRDSSGNHVV FGGGTKLTVL

PSGQAGAAAS ESLFVSNHAY NWVNVISDLK

KIEDLIQSMH IDATLYTESD VHPSCKVTAM

KCFLLELQVI SLESGDASIH DTVENLIILA

NDSLSSNGNV TESGCKECEE LEEKNIKEFL

QSFVHIVQMF INTSEASGGP EDIQMTQSPS

SLSASVGDRV TITCRSTKSL LHSNGITYLY

WYQQKPGKAP KLLIYQMSNL ASGVPSRFSS

SGSGTDFTLT ISSLQPEDFA TYYCAQNLEI

PRTFGQGTKV ELKRATPSHN SHQVPSAGGP

TANSGTSGEV QLVQSGPGLV QPGGSVRISC

AASGYTFTNY GMNWVKQAPG KGLEWMGWIN

TYTGESTYAD SFKGRFTFSL DTSASAAYLQ

INSLRAEDTA VYYCARFAIK GDYWGQGTLL

TVSSEPKSSD KTHTSPPSPD IVLSQSPAIM

SASPGEKVTI SCSASSSVSY MYWYQQKPGS

SPKPWIYRTS NLASGVPARF SGSGSGTSYS

LTISSMEAED AATYYCQQYH SYPPTFGAGT

KLELKSSGGG GSGGGGGSS RSSLEVKLVE

SGPELKKPGE TVKISCKASG YTFTDYSMHW

VNQAPGKGLK WMGWINTETG EPSYADDFKG

RFAFSLETSA STAYLQINNL KNEDTATYFC

ATDYGDYFDY WGQGTTLTVS SAKTTPPSVT

S

SEQ ID NO: 10

MEVQLVESGG GVVRPGGSLR LSCAASGFTF

DDYGMSWVRQ APGKGLEWVS GINWNGGSTG

YADSVKGRFT ISRDNAKNSL YLQMNSLRAE

-continued

DTAVYYCARG RSLLFDYWGQ GTLVTVSRGG

GGSGGGGSGG GGSSELTQDP AVSVALGQTV

RITCQGDSLR SYYASWYQQK PGQAPVLVIY

GKNNRPSGIP DRFSGSSSGN TASLTITGAQ

AEDEADYYCN SRDSSGNHVV FGGGTKLTVL

PSGQAGAAAS ESLFVSNHAY NWVNVISDLK

KIEDLIQSMH IDATLYTESD VHPSCKVTAM

KCFLLELQVI SLESGDASIH DTVENLIILA

NDSLSSNGNV TESGCKECEE LEEKNIKEFL

QSFVHIVQMF INTSEASGGP EDIVLSQSPA

IMSASPGEKV TISCSASSSV SYMYWYQQKP

GSSPKPWIYR TSNLASGVPA RFSGSGSGTS

YSLTISSMEA EDAATYYCQQ YHSYPPTFGA

GTKLELKSSG GGGSGGGGGG SSRSSLEVKL

VESGPELKKP GETVKISCKA SGYTFTDYSM

HWVNQAPGKG LKWMGWINTE TGEPSYADDF

KGRFAFSLET SASTAYLQIN NLKNEDTATY

FCATDYGDYF DYWGQGTTLT VSS

SEQ ID NO: 11

MEVQLVESGG GVVRPGGSLR LSCAASGFTF

DDYGMSWVRQ APGKGLEWVS GINWNGGSTG

YADSVKGRFT ISRDNAKNSL YLQMNSLRAE

DTAVYYCARG RSLLFDYWGQ GTLVTVSRGG

GGSGGGGSGG GGSSELTQDP AVSVALGQTV

RITCQGDSLR SYYASWYQQK PGQAPVLVIY

GKNNRPSGIP DRFSGSSSGN TASLTITGAQ

AEDEADYYCN SRDSSGNHVV FGGGTKLTVL

PSGQAGAAAS ESLFVSNHAY NWVNVISDLK

KIEDLIQSMH IDATLYTESD VHPSCKVTAM

KCFLLELQVI SLESGDASIH DTVENLIILA

NDSLSSNGNV TESGCKECEE LEEKNIKEFL

QSFVHIVQMF INTSEASGGP EQVQLVQSGA

EVKKPGASVK VSCKASGYSF TGYTMNWVRQ

APGQGLEWMG LITPYNGASS YNQKFRGKAT

MTVDTSTSTV YMELSSLRSE DTAVYYCARG

GYDGRGFDYW GQGTLVTVSS GGGGSGGGGS

GGGGSDIQMT QSPSSLSASV GDRVTITCSA

SSSVSYMHWY QQKSGKAPKL LIYDTSKLAS

GVPSRFSGSG SGTDFTLTIS SLQPEDFATY

YCQQWSKHPL TFGQGTKLEI K

-continued

SEQ ID NO: 12

```
MEVQLVESGG GVVRPGGSLR LSCAASGFTF

DDYGMSWVRQ APGKGLEWVS GINWNGGSTG

YADSVKGRFT ISRDNAKNSL YLQMNSLRAE

DTAVYYCARG RSLLFDYWGQ GTLVTVSRGG

GGSGGGGSGG GGSSELTQDP AVSVALGQTV          10

RITCQGDSLR SYYASWYQQK PGQAPVLVIY

GKNNRPSGIP DRFSGSSSGN TASLTITGAQ

AEDEADYYCN SRDSSGNHVV FGGGTKLTVL

EPKSSDKTHT SPPSPNWVNV ISDLKKIEDL

IQSMHIDATL YTESDVHPSC KVTAMKCFLL

ELQVISLESG DASIHDTVEN LIILANDSLS

SNGNVTESGC KECEELEEKN IKEFLQSFVH

IVQMFINTSP SGQAGAAASE SLFVSNHAYD

IQMTQSPSSL SASVGDRVTI TCRSTKSLLH

SNGITYLYWY QQKPGKAPKL LIYQMSNLAS

GVPSRFSSSG SGTDFTLTIS SLQPEDFATY

YCAQNLEIPR TFGQGTKVEL KRATPSHNSH

QVPSAGGPTA NSGTSGEASG GPEDIQMTQT

TSSLSASLGD RVTISCRASQ DISNYLNWYQ

QKPDGTVKLL IYYTSILHSG VPSRFSGSGS

GTDYSLTISN LEQEDFATYF CQQGNTLPWT

FGGGTKLEIK GSTSGSGKPG SGEGSTKGEV

QLVESGGGLV KPGGSLKLSC AASGFAFSIY

DMSWVRQTPE KRLEWVAYIS SGGGTTYYPD

TVKGRFTISR DNAKNTLYLQ MSSLKSEDTA

MYYCARHSGY GTHWGVLFAY WGQGTLVTVS

AGGGGSDILL TQTPASLAVS LGQRATISCK

ASQSVDYDGD SYLNWYQQIP GQPPKLLIYD

ASNLVSGIPP RFSGSGSGTD FTLNIHPVEK

VDAATYHCQQ STEDPWTFGG GTKLEIKRGS

TSGSGKPGSG EGSTKGQVQL QQSGAELVRP

GSSVKISCKA SGYAFSSYWM NWVKQRPGQG

LEWIGQIWPG DGDTNYNGKF KGKATLTADE

SSSTAYMQLS SLASEDSAVY FCARRETTTV

GRYYYAMDYW GQGTSVTVSS
```

SEQ ID NO: 13

```
MDIQMTQSPS SLSASVGDRV TITCRASQDI

RNYLNWYQQK PDGTVKLLIY YTSRLHSGVP

SKFSGSGSGT DYTLTISNLE QEDIATYFCQ

QGNTLPWTFA GGTKLEIKRG GGGSGGGGSG
```

-continued

```
GGGSGGGREVQ LVQSGAELVK PGATMKISCK

ASGYSFTGYT MNWVKQSHGK NLEWMGLINP

YKGVSTYNQK FKDKATLTVD TSTDTAYMEL

LSLTSEDSAV YYCARSGYYG DSDWYFDVWG

AGTTVTVSSP SGQAGAAASE SLFVSNHAYP

TSSSTKKTQL QLEHLLLDLQ MILNGINNYK

NPKLTRMLTF KFYMPKKATE LKHLQCLEEE

LKPLEEVLNL AQSKNFHLRP RDLISNINVI

VLELKGSETT FMCEYADETA TIVEFLNRWI

TFCQSIISTL TEASGGPEDI QMTQSPSSLS

ASVGDRVTIT CRSTKSLLHS NGITYLYWYQ

QKPGKAPKLL IYQMSNLASG VPSRFSSSGS

GTDFTLTISS LQPEDFATYY CAQNLEIPRT

FGQGTKVELK RATPSHNSHQ VPSAGGPTAN

SGTSGEVQLV QSGPGLVQPG GSVRISCAAS

GYTFTNYGMN WVKQAPGKGL EWMGWINTYT

GESTYADSFK GRFTFSLDTS ASAAYLQINS

LRAEDTAVYY CARFAIKGDY WGQGTLLTVS

S
```

SEQ ID NO: 14

```
MKWVTFISLL FLFSSAYSQV QLVESGGGLV

QPGGSLRLSC AASGLTFSSY NMGWFRQAPG

QGLEAVASIT WSGRDTFYAD SVKGRFTISR

DNSKNTLYLQ MNSLRAEDTA VYYCAANPWP

VAAPRSGTYW GQGTLVTVSS SGGGGSGGGG

SGGGGSGGGG SGNWVNVISD LKKIEDLIQS

MHIDATLYTE SDVHPSCKVT AMKCFLLELQ

VISLESGDAS IHDTVENLII LANNSLSSNG

NVTESGCKEC EELEEKNIKE FLQSFVHIVQ

MFINTSGSTS GSGKPGSGEG STKGQVQLVQ

SGAEVKKPGS SVKVSCKASG YTFTDYNMHW

VRQAPGQGLE WIGYIYPYNG GTGYNQKFKS

KATITADEST NTAYMELSSL RSEDTAVYYC

ARGRPAMDYW GQGTLVTVSS GGGGSGGGGS

GGGGSDIQMT QSPSSLSASV GDRVTITCRA

SESVDNYGIS FMNWFQQKPG KAPKLLIYAA

SNQGSGVPSR FSGSGSGTDF TLTISSLQPD

DFATYYCQQS KEVPWTFGQG TKVEIKVDE
```

SEQ ID NO: 15

```
NWVNVISDLK KIEDLIQSMH IDATLYTESD

VHPSCKVTAM KCFLLELQVI SLESGDASIH
```

-continued

DTVENLIILA NNSLSSNGNV TESGCKECEE

LEEKNIKEFL QSFVHIVQMF INTS

SEQ ID NO: 16

MEVQLVESGG GVVRPGGSLR LSCAASGFTF

DDYGMSWVRQ APGKGLEWVS GINWNGGSTG

YADSVKGRFT ISRDNAKNSL YLQMNSLRAE

DTAVYYCARG RSLLFDYWGQ GTLVTVSRGG

GGSGGGGSGG GGSSELTQDP AVSVALGQTV

RITCQGDSLR SYYASWYQQK PGQAPVLVIY

GKNNRPSGIP DRFSGSSSGN TASLTITGAQ

AEDEADYYCN SRDSSGNHVV FGGGTKLTVL

PSGQAGAAAS ESLFVSNHAY NWVNVISDLK

KIEDLIQSMH IDATLYTESD VHPSCKVTAM

KCFLLELQVI SLESGDASIH DTVENLIILA

NDSLSSNGNV TESGCKECEE LEEKNIKEFL

QSFVHIVQMF INTSEASGGP EAKVQLQESG

PSLVQPSQRL SITCTVSGFS LISYGVHWVR

QSPGKGLEWL GVIWRGGSTD YNAAFMSRLS

ITKDNSKSQV FFKMNSLQAD DTAIYFCAKT

LITTGYAMDY WGQGTTVTVS SGGGGSGGGG

SGGGGSDIEL TQSPSSFSVS LGDRVTITCK

ASEDIYNRLA WYQQKPGNAP RLLISGATSL

ETGVPSRFSG SGSGKDYTLS ITSLQTEDVA

TYYCQQYWST PTFGGGTKLE IKR

SEQ ID NO: 17

MDIVLSQSPA IMSASPGEKV TISCSASSSV

SYMYWYQQKP GSSPKPWIYR TSNLASGVPA

RFSGSGSGTS YSLTISSMEA EDAATYYCQQ

YHSYPPTFGA GTKLELKSSG GGGSGGGGG

SSRSSLEVKL VESGPELKKP GETVKISCKA

SGYTFTDYSM HWVNQAPGKG LKWMGWINTE

TGEPSYADDF KGRFAFSLET SASTAYLQIN

NLKNEDTATY FCATDYGDYF DYWGQGTTLT

VSS

-continued

SEQ ID NO: 18

PTSSSTKKTQ LQLEHLLLDL QMILNGINNY

KNPKLTRMLT FKFYMPKKAT ELKHLQCLEE

ELKPLEEVLN LAQSKNFHLR PRDLISNINV

IVLELKGSET TFMCEYADET ATIVEFLNRW

ITFCQSIIST LT

SEQ ID NO: 19

MEVQLVESGG GVVRPGGSLR LSCAASGFTF

DDYGMSWVRQ APGKGLEWVS GINWNGGSTG

YADSVKGRFT ISRDNAKNSL YLQMNSLRAE

DTAVYYCARG RSLLFDYWGQ GTLVTVSRGG

GGSGGGGSGG GGSSELTQDP AVSVALGQTV

RITCQGDSLR SYYASWYQQK PGQAPVLVIY

GKNNRPSGIP DRFSGSSSGN TASLTITGAQ

AEDEADYYCN SRDSSGNHVV FGGGTKLTVL

PSGQAGAAAS ESLFVSNHAY NWVNVISDLK

KIEDLIQSMH IDATLYTESD VHPSCKVTAM

KCFLLELQVI SLESGDASIH DTVENLIILA

NDSLSSNGNV TESGCKECEE LEEKNIKEFL

QSFVHIVQMF INTSEASGGP EMGWSCIILF

LVATATGVHS QVRLSQSGGQ MKKPGDSMRI

SCRASGYEFI NCPINWIRLA PGKRPEWMGW

MKPRHGAVSY ARQLQGRVTM TRDMYSETAF

LELRSLTSDD TAVYFCTRGK YCTARDYYNW

DFEHWGQGTP VTVSSASTKG PSVFPLAPSS

KSTSGGTAAL GCLVKDYFPE PVTVSWNSGA

LTSGVHTFPA VLQSSGLYSL SSVVTVPSSS

LGTQTYICNV NHKPSNTKVD KKVEPKSCDK

SEQ ID NO: 20

MKWVTFISLL FLFSSAYSQV QLVESGGGLV

QPGGSLRLSC AASGLTFSSY NMGWFRQAPG

QGLEAVASIT WSGRDTFYAD SVKGRFTISR

DNSKNTLYLQ MNSLRAEDTA VYYCAANPWP

VAAPRSGTYW GQGTLVTVSS

What is claimed is:

1. A composition comprising:
   an NK engaging domain comprising an antibody or a binding fragment thereof;
   an NK activating domain comprising:
   the amino acid sequence of SEQ ID NO:15, or
   the amino acid sequence of SEQ ID NO:15 comprising an N72D amino acid substitution or an N72A amino acid substitution;
   a first linker linking the NK engaging domain to the NK activating domain, the first linker is selected from the group consisting of:
   SEQ ID NO:3;
   SEQ ID NO:4;
   amino acids 119-133 of SEQ ID NO:5;
   amino acids 494-518 of SEQ ID NO:8;
   amino acids 241-255 of SEQ ID NO:12;
   amino acids 488-506 of SEQ ID:10;
   amino acids 277-294 of SEQ ID NO:14; and
   amino acids 142-161 of SEQ ID NO:14;
   a targeting domain that selectively binds to a target antigen; and
   a second linker linking the NK activating domain to the targeting domain, the second linker is selected from the group consisting of:
   SEQ ID NO:3;
   SEQ ID NO:4;
   amino acids 119-133 of SEQ ID NO:5;
   amino acids 494-518 of SEQ ID NO:8;
   amino acids 241-255 of SEQ ID NO:12;
   amino acids 488-506 of SEQ ID:10;
   amino acids 277-294 of SEQ ID NO:14; and
   amino acids 142-161 of SEQ ID NO:14.

2. The composition of claim 1, wherein the NK engaging domain activates an NK cell.

3. The composition of claim 1, wherein the NK engaging domain blocks inhibition of an NK cell.

4. The composition of claim 1, wherein the antibody fragment comprises an scFv, a F(ab)2, or a Fab.

5. The composition of claim 1, wherein the targeting domain comprises a moiety that selectively binds to a tumor cell.

6. The composition of claim 5, wherein the targeting domain moiety comprises an antibody or a binding fragment thereof.

7. The composition of claim 6, wherein the antibody fragment comprises an scFv.

8. The composition of claim 1, wherein the NK engaging domain and the IL-15 sequence are linked by a linker as set forth in SEQ ID NO:3.

9. The composition of claim 1, wherein NK activating domain and the targeting domain are linked by a linker as set forth in SEQ ID NO:4.

10. The composition of claim 9, wherein the antibody or the binding fragment thereof is human, humanized, or camelid.

11. The composition of claim 1, wherein:
    the first linker comprises the amino acids of SEQ ID NO:3; and
    the second linker comprises the amino acids of SEQ ID NO:4.

12. The composition of claim 1, wherein:
    the first linker comprises amino acids 142-161 of SEQ ID NO:14; and
    the second linker comprises amino acids 277-294 of SEQ ID NO:14.

13. The composition of claim 1, wherein the targeting domain binds to a target antigen or portion thereof selected from CD133, CD20, HER2, CEA, EpCAM, VEGFA, EGFR, CD33, integrin aVB3, CD51, CD152, CD125, CTAA16.88, MUC1, CD19, CD22, CD38, CD30, CD52, uPAR, LIV-1, CD70, IL-3, IL-4R, mesothelin, ROR1, CSPG4, SS1, IGFRI, HSPG2, IGF-1, epithelial-mesenchymal transition (EMT), TRAIL, CD45, CD74, CD23, HIV, or a cancer antigen.

14. The composition of claim 1, wherein the NK engaging domain is amino acid residues 1-240 of SEQ ID NO:1 or amino acid residues 19-140 of SEQ ID NO:14.

15. A pharmaceutical composition comprising:
    the composition of claim 1; and
    a pharmaceutically acceptable carrier.

16. A composition comprising:
    an NK engaging domain comprising an anti-CD16 antibody;
    an NK activating domain comprising an IL-15, wherein the IL-15 comprises an amino acid sequence of SEQ ID NO:15, or an amino acid sequence of SEQ ID NO:15 comprising an N72D amino acid substitution or an N72A amino acid substitution;
    a first linker linking the NK engaging domain to the NK activating domain, the first linker comprising an amino acid sequence of SEQ ID NO:3 or SEQ ID NO:4;

a targeting domain comprising an anti-CD33 antibody or
    binding fragment thereof; and
a second linker linking the NK activating domain to the
    targeting domain, the second linker comprising an
    amino acid sequence of SEQ ID NO:3 or SEQ ID
    NO:4.

17. The composition of claim 16, wherein the anti-CD16
antibody comprises amino acid residues 1-240 of SEQ ID
NO:1, or amino acid residues 19-140 of SEQ ID NO:14.

18. The composition of claim 16, comprising an amino
acid sequence of SEQ ID NO:1 or SEQ ID NO:14.

*    *    *    *    *